US009980424B2

(12) United States Patent
McCarty, II et al.

(10) Patent No.: US 9,980,424 B2
(45) Date of Patent: May 29, 2018

(54) SYSTEM FOR SEED PREPARATION AND METHOD OF USE

(71) Applicant: Dow AgroSciences LLC, Indianapolis, IN (US)

(72) Inventors: Donald L. McCarty, II, Freeland, MI (US); Sivarama Reddy Chennareddy, West Lafayette, IN (US); Toby Cicak, Indianapolis, IN (US); Rodrigo Sarria, West Lafayette, IN (US); David T. Gillespie, Pearland, TX (US); Thomas J. Parsons, Midland, MI (US); Scott R. Kaleyta, Saginaw, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 465 days.

(21) Appl. No.: 14/704,686

(22) Filed: May 5, 2015

(65) Prior Publication Data
US 2015/0319914 A1   Nov. 12, 2015

Related U.S. Application Data

(60) Provisional application No. 61/989,275, filed on May 6, 2014.

(51) Int. Cl.
*G06K 9/00* (2006.01)
*A01C 1/00* (2006.01)
(Continued)

(52) U.S. Cl.
CPC ............... *A01C 1/00* (2013.01); *A01G 1/001* (2013.01); *B25J 9/1697* (2013.01); *B25J 15/0683* (2013.01); *B26D 1/04* (2013.01); *B26D 3/08* (2013.01); *B26D 3/30* (2013.01); *B26D 5/00* (2013.01); *B26D 5/007* (2013.01); *B26D 7/02* (2013.01); *B26D 7/06* (2013.01); *B64G 1/00* (2013.01); *C12N 15/8201* (2013.01);
(Continued)

(58) Field of Classification Search
None
See application file for complete search history.

(56) References Cited

U.S. PATENT DOCUMENTS 4,726,272 A * 2/1988 Forney ................. A01C 1/005
47/89
5,015,580 A   5/1991 Christou et al.
(Continued)

FOREIGN PATENT DOCUMENTS

CN   101001958 A   7/2007
CN   102741415 A   10/2012
(Continued)

OTHER PUBLICATIONS

Lindeberg, Detecting Salient Blob-Like Image Structures and Their Scales with a Scale-Space Primal Sketch: A Method for Focus-of-Attention, 11(3) International Journal of Computer Vision, 283-318 (1993).
(Continued)

*Primary Examiner* — Soo Park
(74) *Attorney, Agent, or Firm* — Marcos P. Rivas; Barnes & Thornburg LLP

(57) ABSTRACT

A system and method for the automated or semi-automated preparation of seeds for transformation and transgenic engineering.

23 Claims, 40 Drawing Sheets

(51) Int. Cl.

| | | |
|---|---|---|
| *A01G 1/00* | (2006.01) | |
| *B26D 5/00* | (2006.01) | |
| *B26D 7/06* | (2006.01) | |
| *G01N 1/28* | (2006.01) | |
| *B26D 7/02* | (2006.01) | |
| *C12N 15/82* | (2006.01) | |
| *B64G 1/00* | (2006.01) | |
| *B25J 15/06* | (2006.01) | |
| *B25J 9/16* | (2006.01) | |
| *B26D 1/04* | (2006.01) | |
| *B26D 3/08* | (2006.01) | |
| *B26D 3/30* | (2006.01) | |
| *G01N 35/00* | (2006.01) | |

(52) U.S. Cl.
CPC ......... *G01N 1/286* (2013.01); *G01N 35/0099* (2013.01); *G01N 2001/2873* (2013.01); *Y10T 83/536* (2015.04); *Y10T 83/6572* (2015.04)

(56) References Cited

U.S. PATENT DOCUMENTS

| | | | |
|---|---|---|---|
| 5,051,825 A | 9/1991 | Cochran et al. | |
| 5,542,795 A | 8/1996 | Mitchell | |
| 5,563,055 A | 10/1996 | Townsend et al. | |
| 5,655,354 A | 8/1997 | Baker et al. | |
| 6,384,301 B1 | 5/2002 | Martinell et al. | |
| 7,002,058 B2 | 2/2006 | Martinell et al. | |
| 7,433,059 B2* | 10/2008 | van der Knijff | A23N 15/08 356/601 |
| 7,473,822 B1 | 1/2009 | Paz et al. | |
| 7,696,408 B2 | 4/2010 | Olhoft et al. | |
| 8,076,076 B2* | 12/2011 | Osborn | A01C 1/025 435/4 |
| 8,363,905 B2* | 1/2013 | Owens, Jr. | B25J 9/1612 348/135 |
| 8,504,204 B2 | 8/2013 | Owens, Jr. | |
| 8,605,149 B2* | 12/2013 | Conrad | G06K 9/00 348/135 |
| 9,027,278 B2 | 5/2015 | Deppermann et al. | |
| 9,058,518 B2* | 6/2015 | Conrad | G06K 9/00536 |
| 9,165,189 B2* | 10/2015 | Conrad | G06K 9/00536 |
| 9,439,361 B2* | 9/2016 | Teasdale | A01G 9/10 |
| 2004/0187177 A1 | 9/2004 | Olhoft et al. | |
| 2005/0114918 A1 | 5/2005 | Hirahara et al. | |
| 2005/0152760 A1 | 7/2005 | Ranner | |
| 2005/0279228 A1 | 12/2005 | Julian et al. | |
| 2007/0207485 A1 | 9/2007 | Deppermann et al. | |
| 2007/0256530 A1 | 11/2007 | Stein | |
| 2008/0028036 A1 | 1/2008 | Slawson et al. | |
| 2008/0229447 A1 | 9/2008 | Hwang et al. | |
| 2008/0280361 A1 | 11/2008 | Calabotta et al. | |
| 2009/0049567 A1 | 2/2009 | Olhoft et al. | |
| 2010/0089216 A1 | 4/2010 | Nonaka et al. | |
| 2010/0185315 A1* | 7/2010 | Schmidt | B25J 15/0019 700/160 |
| 2010/0204824 A1 | 8/2010 | Luce et al. | |
| 2010/0273264 A1 | 10/2010 | Stout et al. | |
| 2011/0117570 A1 | 5/2011 | Cope et al. | |
| 2012/0156964 A1 | 6/2012 | Anderson et al. | |
| 2012/0214389 A1 | 8/2012 | Sekretta et al. | |
| 2012/0311743 A1 | 12/2012 | Coulombier et al. | |
| 2013/0176553 A1* | 7/2013 | Cope | G01J 3/00 356/51 |
| 2014/0055604 A1 | 2/2014 | Delaney | |
| 2014/0173780 A1* | 6/2014 | Pareddy | C12N 15/8205 800/292 |
| 2015/0319914 A1 | 11/2015 | McCarty, II et al. | |
| 2015/0321353 A1 | 11/2015 | McCarty, II et al. | |
| 2015/0322443 A1 | 11/2015 | McCarty, II et al. | |

FOREIGN PATENT DOCUMENTS

| | | |
|---|---|---|
| WO | 0042207 A2 | 7/2000 |
| WO | 2001094879 A1 | 12/2001 |
| WO | 2008112044 A1 | 9/2008 |
| WO | 2011095460 A1 | 8/2011 |

OTHER PUBLICATIONS

Xue et al., "A multi-needle-assisted transformation of soybean cotyledonary node cells", Biotechnol Lett 28:1551-1557, 2006.

Paz et al., "Improved cotyledonary node method using an alternative explant derived from mature seed for efficient Agrobacterium-mediated soybean transformation", Plant Cell Rep. 25:206-213, 2006.

Hinchee et al., "Production of Transgenic Soybean Plants Using Agrobacterium-Mediated DNA Transfer", Nature Biotechnology 6, 915-922, 1988.

Chee et al., "Transformation of soybean (glycine max) by infecting germinating seeds with agrobacterium tumefaciens", Plant Physiol. 1989, pp. 1212-1218, vol. 91.

Hoa et al., "Transformation efficiencies of the soybean variety PC 19 {glycine mad (L.) Merrill} using agrobacterium tumefaciens and the cotyledonary node method" Omonrice, 2008, pp. 1-8, vol. 16.

Miki et al., "Review, Selectable marker genes in transgenic plants: applications, alternatives and biosafety", Journal of Biotechnology 107: 193-232, 2004.

Olhoft et al., "Efficient soybean transformation using hygromycin B selection in the cotyledonary-node method", Planta, 2003, pp. 723-735, vol. 216.

Paz et al., "Agrobacterium-mediated transformation of soybean and recovery of transgenic soybean plants", Iowa State University, Department of Agronomy, Unknown publication date, 6 pages.

Paz, Margie M., "Assessment of conditions affecting Agrobacterium-mediated soybean transformation using the cotyledonary node explant", Euphytica, 2004, pp. 167-179, vol. 136.

Zheng et al., "Refined glufosinate selection in Agrobacterium-mediated transformation of soybean", Plant cell Rep., 2004, pp. 478-482, vol. 22.

Zia et al., "Agrobacterium mediated transformation of soybean (glycine max I.): some conditions standardization", Pak. J. OB, 2010, pp. 2269-2279, vol. 42, No. 4.

Krishnamurthy et al., "Agrobacterium mediated transformation of chickpea (*Cicer arietinum* L.) embryo axes", Plant Cell Reports, 19:235-240, 2000.

McKently et al., "Agrobacterium-mediated transformation of peanut (*Archis hypogaea* L.) embryo axes and the development of transgenic plants", Plant Cell Rep. 14:699-703, 1995.

Australian Examination Report No. 2 issued in connection with Australian Patent Application No. 2015256251, Oct. 9, 2017, 5 pages.

* cited by examiner

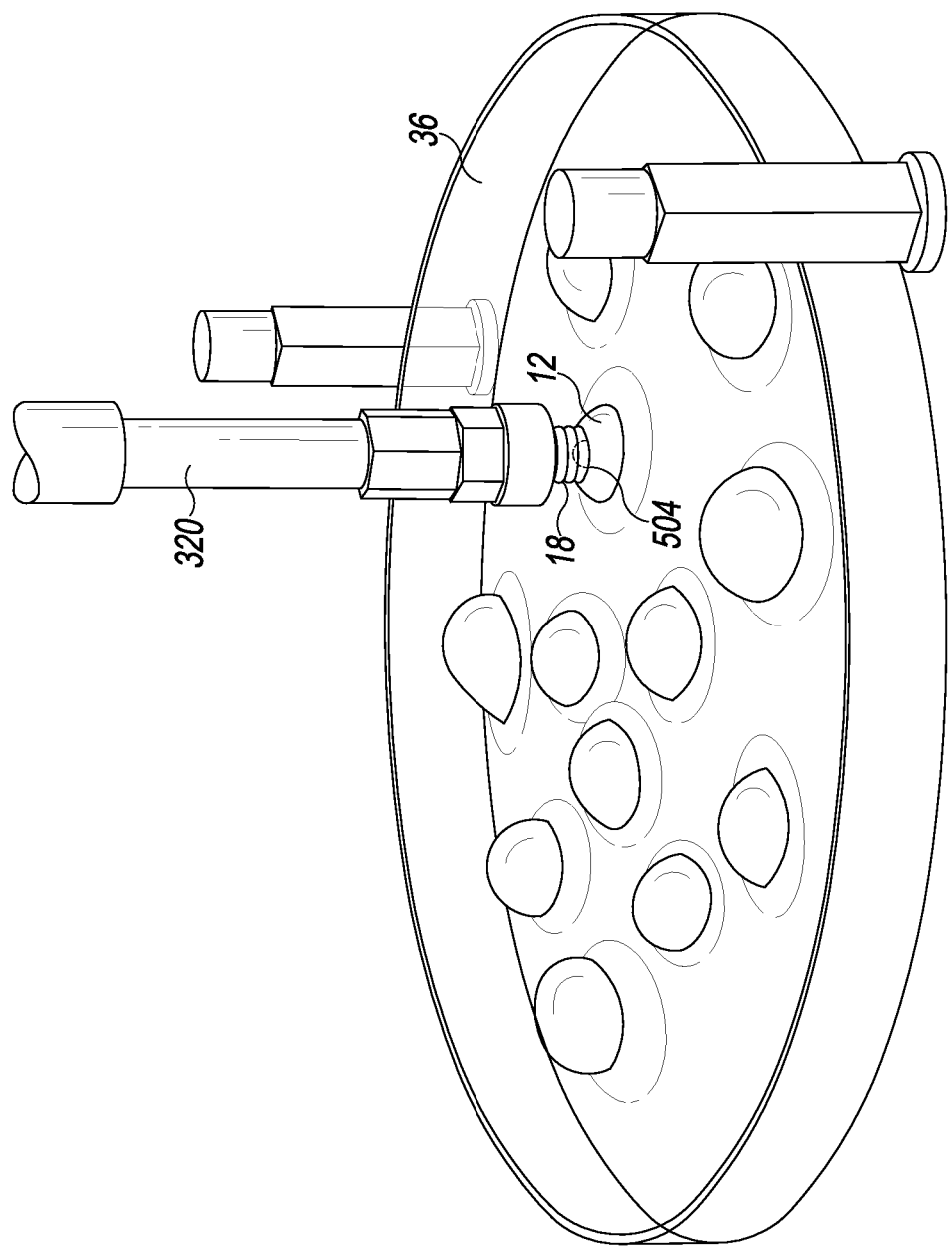

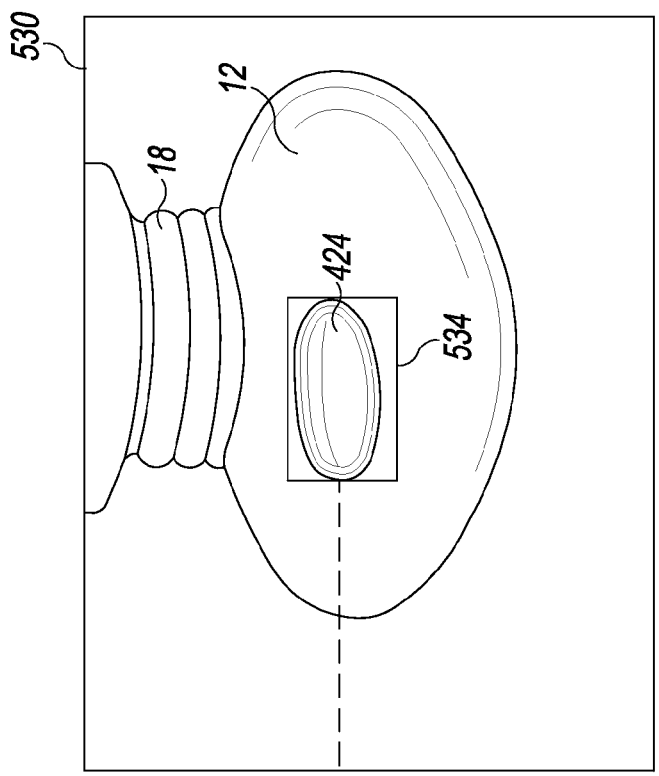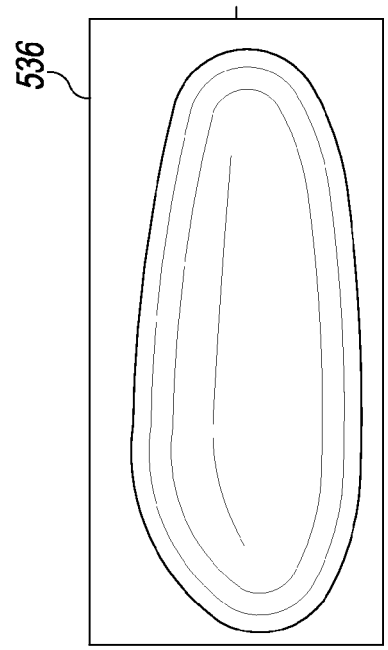
Fig. 32

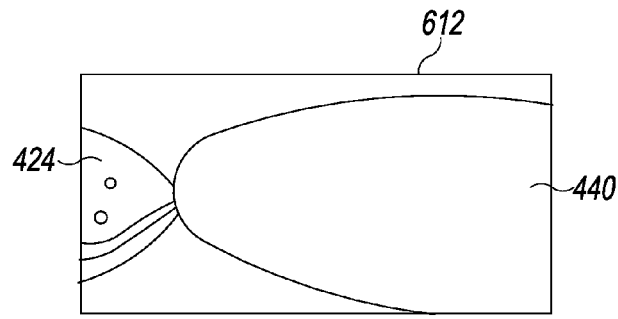
Fig. 42
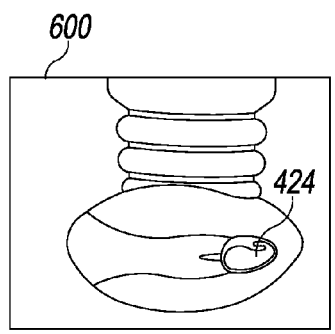 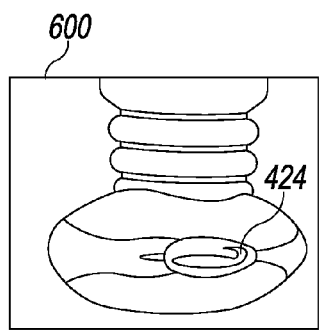 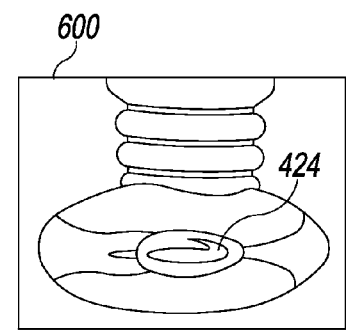
Fig. 43  Fig. 44  Fig. 45
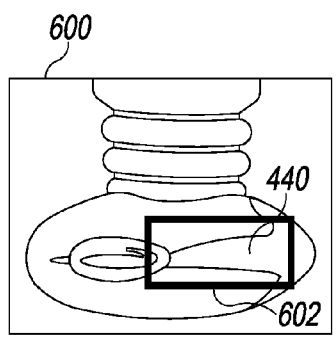 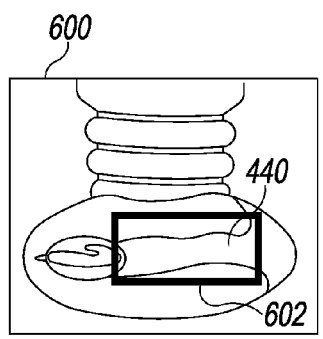 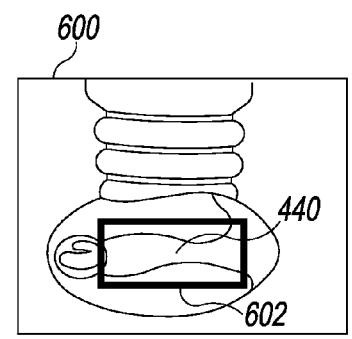
Fig. 46  Fig. 47  Fig. 48

SYSTEM FOR SEED PREPARATION AND METHOD OF USE

This application claims priority to U.S. Provisional Patent Application Ser. No. 61/989,275, which was filed on May 6, 2014 and is expressly incorporated herein by reference.

CROSS-REFERENCE TO RELATED U.S. PATENT APPLICATION

Cross-reference is made to U.S. Provisional Patent Application Ser. No. 61/989,266 entitled "SYSTEM FOR IMAGING AND ORIENTING SEEDS AND METHOD OF USE" by Donald L. McCarty, II et al., which was filed on May 6, 2014; and to U.S. Provisional Patent Application Ser. No. 61/989,276 entitled "SYSTEM FOR CUTTING AND PREPARING SEEDS AND METHOD OF USE" by Donald L. McCarty, II et al., which was filed on May 6, 2014, each of which is expressly incorporated herein by reference.

TECHNICAL FIELD

The present disclosure relates generally to devices for preparing seeds for use in plant breeding, and, more specifically, to a device for preparing seeds and seed explants for gene transformation and transgenic engineering.

BACKGROUND

Soybean (*Glycine max*) is one of the most important agricultural crops, with an annual crop yield of more than 200 million metric tons, and an estimated value exceeding 40 billion U.S. dollars worldwide. Soybean accounts for over 97% of all oilseed production globally. Thus, reliable and efficient methods for improving the quality and yield of this valuable crop are of significant interest.

Traditional breeding methods for improving soybean have been constrained because the majority of soybean cultivars are derived from only a few parental lines, leading to a narrow germplasm base for breeding. Christou et al., TIBTECH 8:145-151 (1990). Modern research efforts have focused on plant genetic engineering techniques to improve soybean production. Transgenic methods are designed to introduce desired genes into the heritable germline of crop plants to generate elite plant lines. The approach has successfully increased the resistance of several other crop plants to disease, insects, and herbicides, while improving nutritional value.

Several methods have been developed for transferring genes into plant tissue, including high velocity microprojection, microinjection, electroporation, and direct DNA uptake. *Agrobacterium*-mediated gene transformation has more recently been used to introduce genes of interest into soybeans. However, soybeans have proven to be a challenging system for transgenic engineering. Efficient transformation and regeneration of soybean explants is difficult to achieve, and frequently hard to repeat.

*Agrobacterium tumefaciens*, a pathogenic, soil-dwelling bacterium, has the inherent ability to transfer its DNA, called T-DNA, into host plant cells and to induce the host cells to produce metabolites useful for bacterial nutrition. Using recombinant techniques, some or all of the T-DNA may be replaced with a gene or genes of interest, creating a bacterial vector useful for transforming the host plant. *Agrobacterium*-mediated gene transfer is typically directed at undifferentiated cells in tissue culture, but may also be directed at differentiated cells taken from the leaf or stem of the plant. A number of procedures have been developed for *Agrobacterium*-mediated transformation of soybean, which may loosely be classified based on the explant tissue subjected to transformation.

U.S. Pat. No. 7,696,408, Olhoft, et al., discloses a cotyledonary node method for transforming both monocotyledonous and dicotyledonous plants. The "cot node" method involves removing the hypocotyl from 5-7 day old soybean seedlings by cutting just below the cotyledonary node, splitting and separating the remaining hypocotyl segment with the cotyledons, and removing the epicotyl from the cotyledon. The cotyledonary explant is wounded in the region of the axillary bud and/or cotyledonary node, and cultivated with *Agrobacterium tumefaciens* for five days in the dark. The method requires in-vitro germination of the seeds, and the wounding step introduces significant variability.

U.S. Pat. No. 6,384,301, Martinelli et al., discloses *Agrobacterium*-mediated gene delivery into living meristem tissue from soybean embryos excised from soybean seeds, followed by culturing of the meristem explant with a selection agent and hormone to induce shoot formation. Like the "cot node" method, the meristem explants are preferably wounded prior to infection.

U.S. Pat. No. 7,473,822, Paz et al., discloses a modified cotyledonary node method called the "half-seed explant" method. Mature soybean seeds are imbibed, surface-sterilized and split along the hilum. Prior to infection, the embryonic axis and shoots are completely removed, but no other wounding occurs. *Agrobacterium*-mediated transformation proceeds, potential transformants are selected, and explants are regenerated on selection medium.

Transformation efficiencies remain relatively low with these methods, on the order of 0.3% to 2.8% for the "cot node" method, 1.2 to 4.7% for the "meristem explant" method, and between 3.2% and 8.7% (overall 4.9%) for the "half-seed explant" method. Transformation efficiencies of approximately 3% are typical in the art.

An improved "split-seed" transgenic protocol may accelerate future production and development of transgenic soybean products. An efficient and high-throughput method for stable integration of a transgene into soybean tissue would facilitate breeding programs and have the potential to increase crop productivity.

SUMMARY

A method and apparatus for automated seed preparation is disclosed. According to one aspect, the method includes locating the seed on a surface or container, engaging the seed with an automated tool, orienting the seed for cutting or wounding, and cutting or wounding the seed when the seed is oriented. The method may also include partially cutting the embryonic axis of the seed. In some embodiments, the cut or wounded seed is transformed with exogenous DNA.

The scope of the disclosure is not limited to the specified structures or the specific terms used. For example, the term "robotic arm" may be substituted with the term "automated tool." Additionally, the terms "surface" or "container" may be substituted for the term "tray," and the term "cutting block" may be substituted with the terms "cutting surface," "support block," or "block."

The automated seed preparation method may include capturing an image of a tray including at least one seed, locating the seed on the surface or container (e.g., the tray) based on a captured image, gripping the seed with an automated tool (e.g., the robotic arm), orienting the seed on a cutting surface (e.g., the cutting block) for bisection of the seed, and bisecting the seed when the seed is oriented on the cutting surface. In some embodiments, the method may also include partially cutting the embryonic axis of the seed. In some embodiments, locating the seed may comprise locating the seed on a tray having a plurality of seeds placed thereon.

In some embodiments, the method may further comprise operating the robotic arm to move the seed from the tray to a separate location, capturing a plurality of images of the seed in the separate location, and determining a proper orientation of the seed for bisection based on the plurality of captured images. In some embodiments, the plurality of images may be captured by one camera that captures an image set from one or more perspectives. In other embodiments, capturing the plurality of images may comprise operating a first camera to capture a first image set of the seed from a first perspective, and operating a second camera to capture a second image set of the seed from a second perspective different from the first perspective. As used herein, an image set may include one image or a plurality of images.

Additionally, in some embodiments, determining the proper orientation of the seed may comprise locating a center of a hilum of the seed and a longitudinal axis of the seed.

In some embodiments, orienting the seed on the cutting surface (e.g., the cutting block) for bisection of the seed may comprise aligning the seed with a cutting blade of a cutting device along an imaginary plane defined by the center of the hilum of the seed and the longitudinal axis of the seed.

In some embodiments, the method may further comprise trimming an embryonic axis of the seed when the seed is located on the cutting surface. In some embodiments, determining the proper orientation of the seed for bisection based on the plurality of captured images may also include determining the proper orientation of the seed for trimming the embryonic axis. Trimming the embryonic axis of the seed may include positioning a cutting blade perpendicular to a longitudinal axis of the seed.

In some embodiments, bisecting the seed on the cutting surface may comprise bisecting the seed after trimming the embryonic axis of the seed. Additionally, in some embodiments, bisecting the seed on the cutting surface may comprise cutting through less than an entirety of the seed. In some embodiments, the method may further comprise moving the bisected seed to an *Agrobacterium tumefaciens* solution.

In some embodiments, the method may comprise sterilizing a grip of the automated tool (e.g., the robotic arm) prior to gripping the seed. The method may comprise operating the automated tool or robotic arm to select a cutting blade, and positioning the cutting blade on a cutting device. The method may further comprise bisecting the seed when the seed is oriented on the cutting block by inserting the cutting blade into the seed. In some embodiments, the method may include gripping the cutting blade with the same or a different automated tool after bisecting the seed and operating the automated tool to replace the cutting blade with a second cutting blade on the cutting device.

According to another aspect, a seed preparation apparatus comprises a first camera configured to capture a first image set of a seed placed on a surface or a tray, a robotic arm operable to grip the seed and to move the seed from the surface or the tray to a lighted chamber, a second camera configured to capture a second image set of the seed within the lighted chamber, and a cutting block configured to receive the seed. The robotic arm is further operable to position the seed on the cutting block in a proper orientation for bisection of the seed.

In some embodiments, the seed preparation apparatus may comprise a light source positioned on a first side of the tray to illuminate the seeds on the tray. In some embodiments, the lighted chamber may be defined in a lighted dome.

In some embodiments, the seed preparation apparatus may comprise a third camera configured to capture a third image set of the seed within the lighted chamber, and an electronic controller configured to analyze the second image set and the third image set to determine the proper orientation of the seed.

In some embodiments, the seed preparation apparatus may comprise a light source configured to light an interior of the lighted chamber. In some embodiments, the electronic controller may be further configured to analyze the first image set to locate the seed on the tray.

According to another aspect, a seed preparation apparatus comprises a chamber, a first camera configured to capture a first image set of a seed on a tray, a second camera configured to capture a second image set of the seed within the chamber, a cutting device configured to bisect the seed, a robotic arm including a gripping device to grip the seed for movement, and an electronic controller. The electronic controller is configured to locate the seed on the tray based on the first image set, operate the robotic arm to grasp the seed on the tray and move the seed to the cutting device in an orientation based on the second image set, and operate the cutting device to bisect the seed.

In some embodiments, the electronic controller may be configured to operate the robotic arm to move the seed from the tray to the chamber, and operate the second camera to capture the second image set.

In some embodiments, the electronic controller may be configured to analyze a plurality of images of the seed to determine a proper orientation of the seed for bisection of the seed and trimming an embryonic axis of the seed.

In some embodiments, the robotic arm may be configured to move the seed to the cutting device to position the seed in the proper orientation, and the cutting device is configured to trim the embryonic axis of the seed while the seed is positioned in the cutting device in the proper orientation.

According to another aspect of the disclosure, a cutting block is disclosed. The cutting block comprises a body including a front wall and a substantially planar upper wall extending away from the front wall. A first opening is defined in the front wall, a second opening is defined in the upper wall, and a plurality of inner walls extend inwardly from the first opening and the second opening to define a slot in the front wall and the upper wall. The slot is sized to receive a cutting tool. The cutting block is sized to support a seed such as a soybean seed or any seed of that size that cutting tool may be advanced along the slot into contact with the seed.

In some embodiments, the upper wall may extend from the front wall to a rear edge. The body may further include a substantially planar side wall extending upwardly from the rear edge. In some embodiments, the side wall may be a first side wall extending from the rear edge of the upper wall to an upper edge The body may further include a second side wall extending from the upper edge of the first side wall. The second side wall may extend obliquely relative to the first side wall and the upper wall of the body.

In some embodiments, the second side wall may extend from the upper edge of the first side wall to a top edge, and the body may further include a top wall extending from the top edge of the second side wall. The top wall may extend obliquely relative to the second side wall.

In some embodiments, the top wall may extend parallel to the upper wall of the cutting block.

In some embodiments, the slot may extend from the first opening in the front wall to a back edge positioned between the front wall and the rear edge of the upper wall.

In some embodiments, the first opening may be positioned in a center of the front wall. In some embodiments, the body may be formed as a single monolithic metallic body. In some embodiments, the body may be secured to a surface with an automated cutting system.

In further embodiments, a combination is disclosed. The combination includes each cutting block herein with a seed such as a soybean seed o any seed of that size. The soybean seed may be cut, bisected, trimmed, or otherwise wounded for transformation. In some embodiments, the embryonic axis of the seed may be trimmed for transformation.

According to another aspect, a cutting system is disclosed. The cutting system includes an automated cutting system including a cutting tool, and a cutting block including an upper wall and a slot defined in the upper wall that is sized to receive the cutting tool of the automated cutting system. The automated cutting system is operable to move the cutting tool linearly along a first axis relative to the cutting block, and rotate the cutting tool about the first axis to position the cutting tool for insertion into the slot.

In some embodiments, the automated cutting system may further include an electric motor operable to move the cutting tool linearly along the first axis, and a pneumatic device operable to rotate the cutting tool about the first axis.

In some embodiments, the automated cutting system further may include a pair of movable jaws configured to receive the cutting tool. The pair of movable jaws may be operable to move between an unlocked position in which the cutting tool is removable from the jaws, and a locked position in which the cutting tool is retained on the jaws.

In some embodiments, the automated cutting system further may include a second pneumatic device operable to move the pair of jaws between the unlocked position and the locked position.

In some embodiments, the automated cutting system further may include an electronic controller including a processor, a memory device, and a plurality of instructions stored in the memory device, which, when executed by the processor, cause the processor to operate a first compressed air source to move the pair of jaws from the unlocked position to the locked position, operate a second compressed air source to rotate the cutting tool about the first axis to an orientation in which the cutting tool extends vertically, and operate the first electric motor to advance the cutting tool into the slot defined in the cutting block. In some embodiments, the electronic controller may further include a plurality of instruction, which, when executed by the processor, cause the processor to operate the first electric motor to remove the cutting tool from the slot defined in the cutting block, operate the second compressed air source to rotate the cutting tool about the first axis to a second orientation in which the cutting tool extends horizontally, and operate the first electric motor to advance the cutting tool over the upper wall of the cutting block.

In some embodiments, the cutting block may include a front wall and the substantially planar upper wall extends away from the front wall, and a first opening is defined in the front wall, a second opening is defined in the upper wall, and a plurality of inner walls extend inwardly from the first opening and the second opening to define the slot in the front wall and the upper wall.

In some embodiments, the cutting tool may be removably coupled to the automated cutting system.

According to another aspect, a method of cutting a seed is disclosed. The method includes advancing a cutting tool along a first axis into a slot defined in a cutting block and to make a first cut in the seed, rotating the cutting tool about the first axis, and advancing the cutting tool into the seed to make a second cut. In some embodiments, the cutting tool may be rotated by operating a compressed air source or an electric motor. In some embodiments, the cutting tool may be advanced into the seed by operating one or more electric motors.

In some embodiments, the method may comprise positioning the cutting tool on a pair of jaws, and moving the pair of jaws to secure the cutting tool to the pair of jaws. In some embodiments, the pair of jaws may be moved apart to engage the cutting tool. Additionally, in some embodiments, the pair of jaws may be moved by operating a compressed air source.

In some embodiments, positioning the cutting tool on the pair of jaws may include attaching the cutting tool to an automated tool such as a robotic arm.

In some embodiments, the method may further comprise operating a negative pressure source to attach the cutting tool to the robotic arm via suction.

According to another aspect, a method for imaging a seed is disclosed. The method includes using an automated tool such as a robotic arm to position a seed including a hilum within a lighted structure such as a dome, projecting the seed onto a first plane extending perpendicular to a center axis of the lighted dome, rotating the seed to orient the seed parallel to a first imaginary horizontal line positioned in the first plane, projecting the seed onto a second plane extending perpendicular to the first plane, orienting the seed parallel to a second imaginary horizontal line positioned in the second plane, identifying a distance between the hilum of the seed and the second imaginary horizontal line, and orienting the seed to position the hilum on the second imaginary horizontal line based on the identified distance.

As described above, the scope of the disclosure is not limited to the disclosed structures or terms used. Thus, the term "lighted dome" may be substituted with, for example, the term "lighted structure."

In some embodiments, orienting the seed to position the hilum on the second imaging horizontal line may comprise orienting the seed to position a center of the hilum on the second imaginary horizontal line. In some embodiments, orienting the seed to position the center of the hilum on the second imaginary horizontal line may comprise orienting the seed such that a center of mass of the hilum is coincident with a center of mass of the seed.

Additionally, in some embodiments, the method may further comprise identifying a location of the embryo of the seed, identifying an edge of the hilum nearest the identified location and an outer edge of the seed along the second imaginary horizontal line, and identifying a point between the edge of the hilum and the outer edge of the seed at which to trim an embryonic axis of the seed. In some embodiments, identifying the location of the embryo may comprise analyzing one or more projections of the seed onto the second plane using feature matching.

In some embodiments, projecting the seed onto the first plane may comprise capturing a first image set with a first camera, and projecting the seed on to a second plane may comprise capturing a second image set with a second camera.

In some embodiments, the first camera may have an optical axis parallel to an optical axis of the second camera, and capturing the first image set with the first camera may comprise capturing light reflected off a mirror extending at a forty-five degree angle relative to the optical axis of the first camera.

In some embodiments, rotating the seed to orient the seed parallel to the first imaginary horizontal line may comprise rotating the seed in response to determining the seed is not oriented parallel to the first imaginary horizontal line. In some embodiments, orienting the seed parallel to the second imaginary horizontal line may comprise orienting the seed in response to determining the seed is not oriented parallel to the second imaginary horizontal line, and orienting the seed to position the hilum on the secondary imaginary horizontal line may comprise orienting the seed in response to determining the hilum is not positioned on the second imaginary horizontal line.

In some embodiments, the method may further comprise analyzing a first image set corresponding with the projection of the seed onto the first plane to determine an orientation of the seed relative to the first imaginary horizontal line, and analyzing a second image set corresponding with the projection of the seed onto the second plane to determine an orientation of the seed relative to the second imaginary horizontal line.

In some embodiments, analyzing the second image set may comprise identifying a first longitudinal end and a second longitudinal end of the seed, identifying a left rectangular vertical cross section of the seed at the first longitudinal end, identifying a right rectangular vertical cross section of the seed at the second longitudinal end, determining a center of mass of each of the left rectangular vertical cross section and the right rectangular cross section, and interconnecting the centers of mass of the left rectangular vertical cross section and the right rectangular cross section with an imaginary line segment. In some embodiments, orienting the seed parallel to the second imaginary horizontal line may comprise orienting the seed such that the line segment is parallel to the second imaginary horizontal line.

In some embodiments, each of the left rectangular vertical cross section and the right rectangular vertical cross section may have a horizontal width equal to at least ten image pixels.

In some embodiments, analyzing the second image set may further comprise determining an angle of the line segment relative to the second imaginary horizontal line, and an amount of rotation of the seed to orient the line segment parallel to the second imaginary horizontal line is based on the determined angle.

In some embodiments, the method may further comprise projecting the seed onto the second plane in response to orienting the seed parallel to the second imaginary horizontal line, and analyzing a third image set corresponding with the projection of the seed onto the second plane in response to orienting the seed parallel to the second imaginary horizontal line to identify the distance between the hilum and the second imaginary horizontal line.

In some embodiments, analyzing the third image set may comprise identifying a longitudinal end of the seed, determining a center of mass of each of the longitudinal end and the hilum, and interconnecting the centers of mass of the longitudinal end and the hilum with an imaginary line segment. Additionally, in some embodiments, orienting the seed to position the hilum on the second imaginary horizontal line may comprise orienting the seed such that the line segment is coincident with the second imaginary horizontal line.

In some embodiments, analyzing the third image set may further comprise determining an angle of the line segment relative to the second imaginary horizontal line, and an amount of movement of the seed to orient the line segment coincident with the second imaginary horizontal line is based on the determined angle.

In some embodiments, the method may further comprise determining a height of the seed for positioning a cutting blade based on the projection of the seed onto the second plane. The height may be a width of the seed in a direction perpendicular to the second imaginary horizontal line. In some embodiments, the method may further include attaching the seed to the robotic arm via a suction force.

According to another aspect, a method for imaging a seed includes capturing a plurality of images of a seed, determining an orientation of the seed and a location of the hilum of the seed based on the plurality of captured images, and moving the seed with a robotic arm to orient the seed in a position based on the determined orientation of the seed and the location of the hilum.

In some embodiments, capturing the plurality of images may comprise capturing a first image set of the seed with a first camera from a first perspective, and capturing a second image set of the seed with a second camera from a second perspective perpendicular to the first perspective.

In some embodiments, determining the orientation of the seed may comprise determining an orientation of the seed relative to a first border line of the first captured image set, and determining an orientation of the seed relative to a second border line of the second captured image set.

According to another aspect, a seed imaging apparatus includes a robotic arm, one or more light sources, a hollow body having a center axis and configured to be lighted by the one or more light sources, a first camera configured to capture a first image set of a seed positioned within the hollow body. The first image set is captured from a first perspective along the center axis. The seed imagining apparatus includes a second camera configured to capture a second image set of the seed from a second perspective along a second axis perpendicular to the center axis, and an electronic controller configured to analyze the first image set and the second image set to determine a proper orientation of the seed for bisection and to instruct the robotic arm to move the seed into the proper orientation.

In some embodiments, an optical axis of the first camera may be parallel to an optical axis of the second camera, and the first camera may be configured to capture light reflected off a mirror that extends at a forty-five degree angle relative to the optical axis of the first camera.

In some embodiments, the robotic arm may be configured to secure the seed by applying a suction force to a side of the seed.

BRIEF DESCRIPTION OF THE DRAWINGS

The detailed description particularly refers to the following figures, in which:

FIGS. 30-31 are illustrations of the system of FIG. 1 moving a seed to an imaging station of the system;

FIGS. 32-55 are illustrations of images created during the procedure of FIGS. 17-19;

DETAILED DESCRIPTION OF THE DRAWINGS

Figure 1:
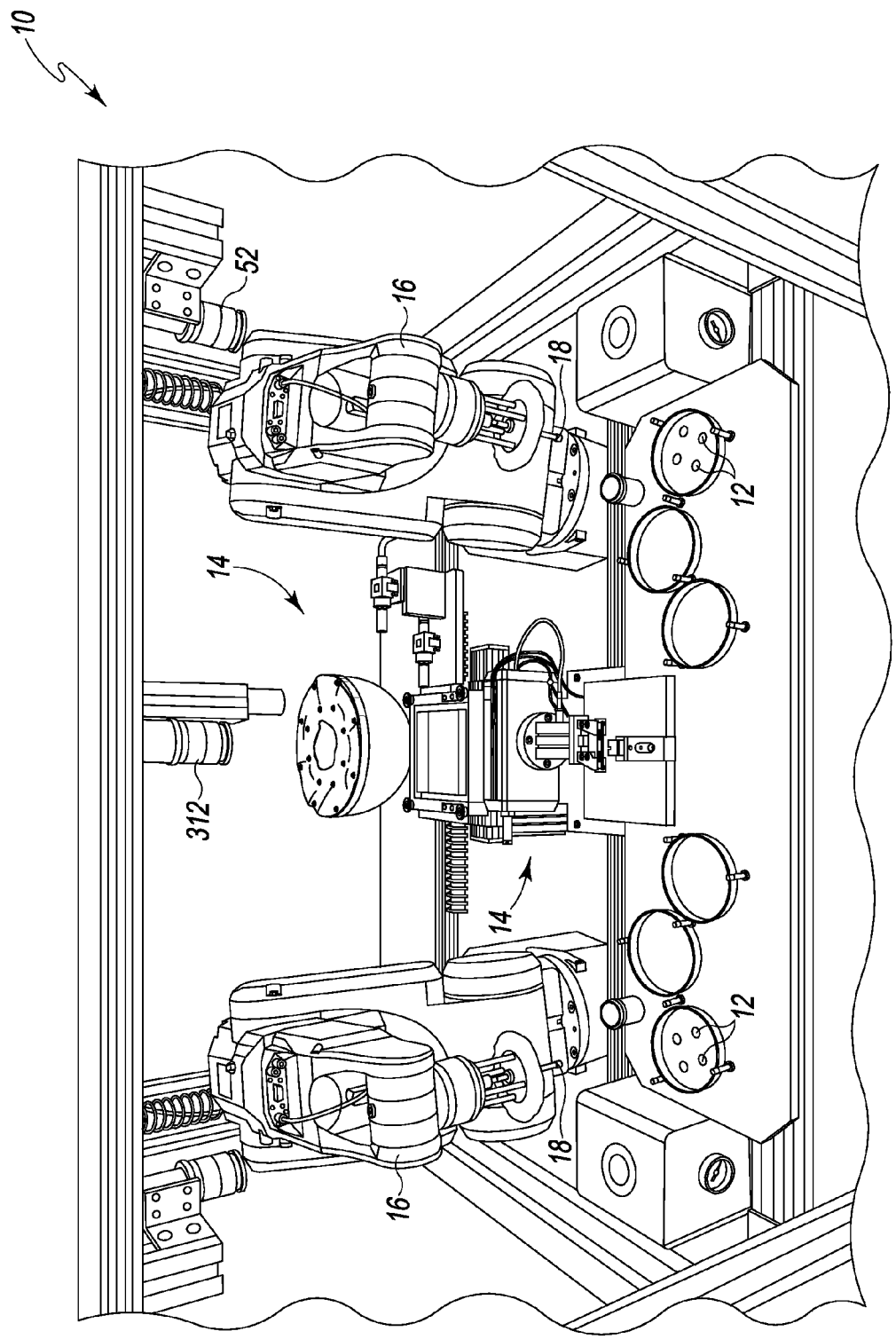
FIG. 1 is a perspective view of a system for preparing seeds for gene transformation.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

As used herein, a "cotyledon" may generally refer to an embryonic leaf or "primary leaf" of the embryo of a seed plant. A cotyledon is also referred to in the art as a "seed leaf." Dicotyledonous species, such as soybean, have two cotyledons. A cotyledon segment refers to any portion of a cotyledon, whether it be an entire or whole cotyledon or a fragment or partial portion of a cotyledon. The "cotyledonary node" refers to the point of attachment of the cotyledons to the embyro in the seed or seedling, and may generally refer to the tissue associated with that point of attachment.

As used herein, the term "grasping" refers to holding or seizing the soybean seed with a tool. Any subsequent mechanism or action that allows the soybean seed to be firmly clasped is considered within the scope of the term grasping.

As used herein, the term "cutting blade" refers to any cutting tool such as a razor, knife, water knife, scalpel, chisel, cutter, lance and the like suitable for cutting or wounding a seed for transformation. In the embodiments disclosed herein, each reference to a cutting blade may be substituted with a laser or microlaser emission for cutting or wounding a seed for transformation.

As used herein, the term "seed coat" refers to an integument of the ovule that serves as a seed's protective coat. Seed coat may be described by the alternative descriptive terms of "testa" or "husk", in addition to other similar terms known in the art. Seed coats may contain hydrophobic substances such as suberin, cutin, lignin, callose, pectin, waxes, and insoluble products of phenolic oxidation. In legumes, like soybean, the testa contains a palisade layer of thick-walled macrosclereid cells, whose caps extend into a suberized sub-cuticle, with a waxy cuticle external to the thicker suberin layer.

As used herein, the terms "embryonic axis" or "embryo axis" refer to the major portion of the embryo of the plant, and generally includes the epicotyl and hypocotyl.

As used herein, the term "genetically modified" or "transgenic" plant refers to a plant cell, plant tissue, plant part, plant germplasm, or plant which comprises a preselected DNA sequence which is introduced into the genome of a plant cell, plant tissue, plant part, plant germplasm, or plant by transformation.

As used herein, the term "transgenic," "heterologous," "introduced," or "foreign" DNA or gene refer to a recombinant DNA sequence or gene that does not naturally occur in the genome of the plant that is the recipient of the recombinant DNA or gene, or that occurs in the recipient plant at a different location or association in the genome than in the untransformed plant.

As used herein, the term "explant" refers to a piece of soybean tissue that is removed or isolated from a donor plant (e.g., from a donor seed), cultured in vitro, and is capable of growth in a suitable media.

As used herein, the term "plant" refers to either a whole plant, plant tissue, plant part, including pollen, seeds, or an embryo, plant germplasm, plant cell, or group of plants. The class of plants that can be used in the method of the invention is not limited to soybeans, but may generally include any plants that are amenable to transformation techniques, including both monocotyledonous and dicotyledonous plants.

As used herein the term "transformation" refers to the transfer and integration of a nucleic acid or fragment into a host organism, resulting in genetically stable inheritance. Host organisms containing the transformed nucleic acid fragments are referred to as "transgenic" or "recombinant" or "transformed" organisms. Known methods of transformation include *Agrobacterium tumefaciens* or *Agrobacterium rhizogenes* mediated transformation, calcium phosphate transformation, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS™ mediated transformation, aerosol beaming, or PEG transformation as well as other possible methods. Referring to FIG. 1, a system 10 for preparing seeds or seed explants for gene transformation by any known method is shown.

The system 10 is illustratively configured to prepare soybean seeds (hereinafter seeds 12) as part of a transgenic protocol and the development of transgenic soybean products. Exemplary transgenic protocols are described in U.S. patent application Ser. No. 14/133,370 entitled "IMPROVED SOYBEAN TRANSFORMATION FOR EFFICIENT AND HIGH-THROUGHPUT TRANSGENIC EVENT PRODUCTION" and U.S. patent application Ser. No. 14/134,883 entitled "IMPROVED SOYBEAN TRANSFORMATION FOR EFFICIENT AND HIGH-THROUGHPUT TRANSGENIC EVENT PRODUCTION," which are expressly incorporated herein by reference. It should be appreciated that any of the devices and methods described herein can be used in connection with the transformation methods disclosed in those applications. It should also be appreciated that in other embodiments any of the devices and methods described herein may be configured for use with other classes of plants that are amenable to transformation techniques, including both monocotyledonous and dicotyledonous plants.

The system 10 includes a number of processing stations 14 and a pair of robotic arms 16 that move seeds 12 between the processing stations 14. In the illustrative embodiment, each robotic arm 16 is an Epson model C3 six-axis articulated arm that is configured to operate independently of the other robotic arm. In other embodiments, the robotic arms 16 may have a different number of degrees of freedom than those described herein. For example, the robotic arms 16 may be embodied as robotic arms having at least independent axes. Each arm 16 includes a grip 18 configured to grasp and hold a seed 12. The system 10 may be operated with one of the arms 16 out-of-service. It should be appreciated that in other embodiments the system may include only a single robotic arm 16 to move the seeds 12 between the processing stations 14. Additionally, in the illustrative embodiment, each robotic arm 16 is capable of rotating the corresponding grip 18 about its axis by at least 180 degrees.

Figure 2:
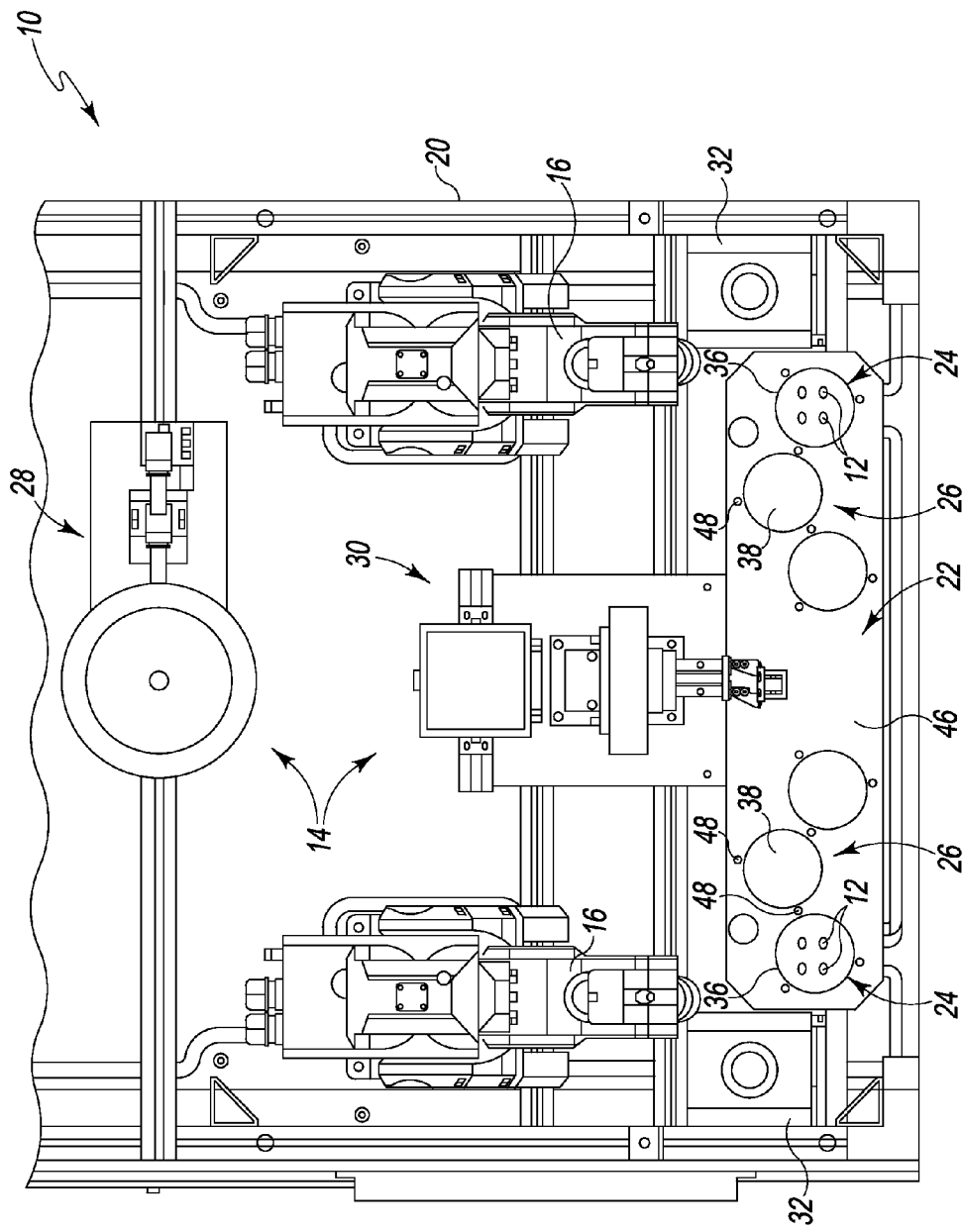
FIG. 2 is a top plan view of the system of FIG. 1.

As shown in FIG. 2, the processing stations 14 and the robotic arms 16 are arranged on a table 20. The processing stations 14 include a dock 22 positioned at the front of the table 20. The dock 22 includes a pair of delivery areas 24 where seeds 12 may be positioned for processing by the system 10 and a pair of receiving areas 26 where seeds 12 may be positioned after processing by the system 10. The stations 14 also include an imaging station 28 that is operable to capture a number of images of the seeds 12. The system 10 also includes a cutting station 30 that is operable to cut each seed 12 based on the images captured by the station 28. The system 10 also includes a sterilization device 32 that is configured to sterilize each grip 18 of the robotic arms 16 and a bin or tray 34 that receives cutting blades for use the cutting station 30.

In use, the system 10 may be operated to cut automatically a number of soybean seeds 12 for transformation. To do so, the system 10 may locate one of the seeds 12 on a plate 36 positioned on one of the delivery areas 24 of the dock 22. The system 10 may then operate the robotic arm 16 closest to the plate 36 to grasp the selected seed 12 with the grip 18 and move the seed 12 to the imaging station 28. After a series of images of the seed 12 are taken, the arm 16 may advance the seed 12 to the cutting station 30 such that one or more cuts may be made to the seed 12 to prepare it for transformation. After the seed 12 is cut, the arm 16 may move the seed 12 to another plate 38 positioned on one of the receiving areas 26 of the dock 22. A user may then remove the plate 38 including the cut seed to further process the seed in accordance with the transgenic protocol. Each of these processing steps and the various components of the system 10 are described in greater detail below in reference to FIGS. 3-59.

Figure 3:
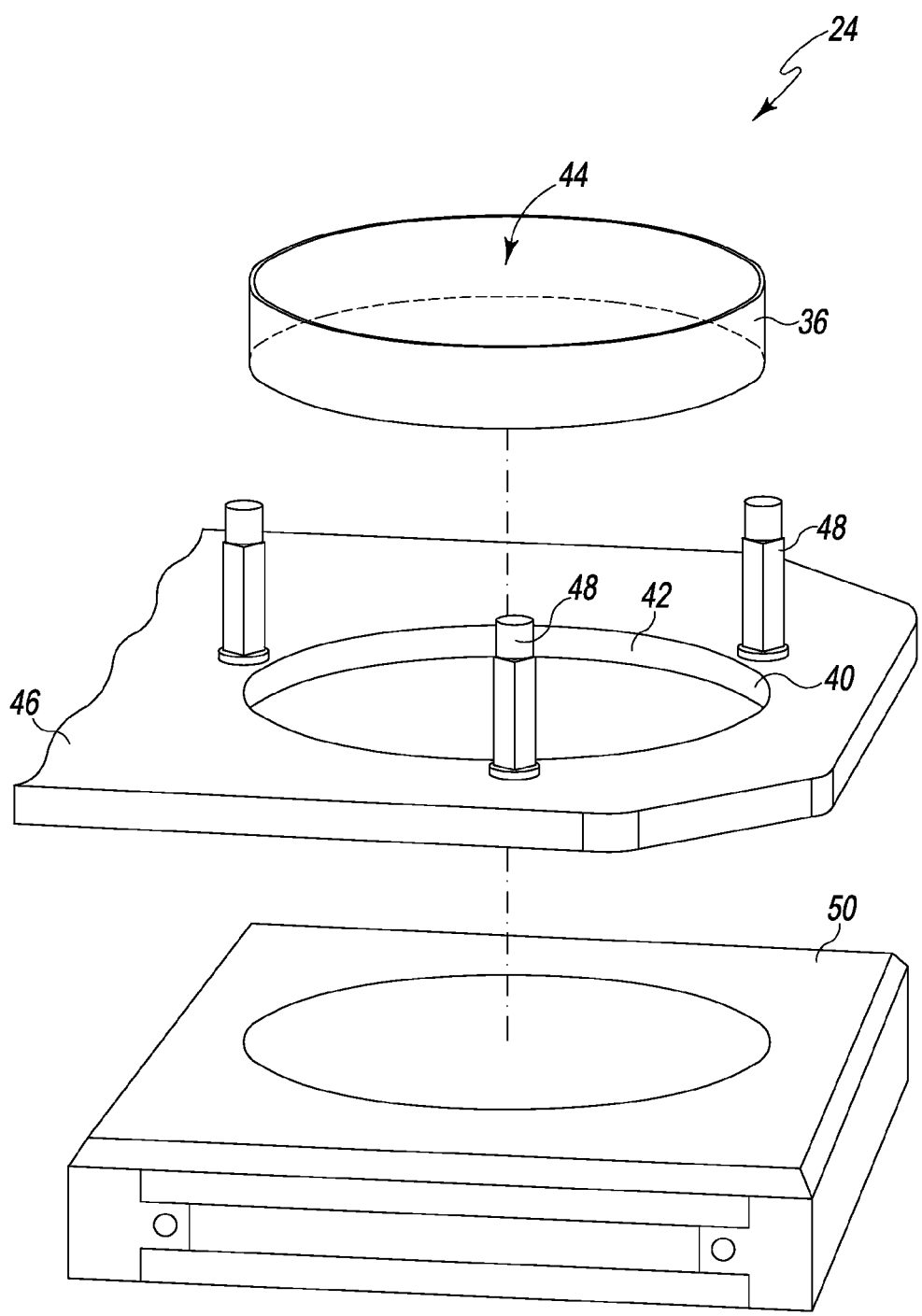
FIG. 3 is an exploded perspective view of a portion of a dock of the system of FIG. 2.

Referring now to FIG. 3, a portion of the dock 22 and one of the delivery areas 24 is shown in greater detail. In the illustrative embodiment, the other delivery area 24 is identical to the delivery area shown in FIG. 3. The delivery area 24 includes a circular base 40 that is positioned in an opening defined in a plate 46 of the dock 22. The base 40 is sized to receive one of the plates 36, and is constructed of a transparent material such as, for example, glass, Plexiglas, or acrylic. The base 40 extends from a top surface 42 to a bottom surface (not shown) positioned below the plate 46. Because the base 40 is transparent, objects resting on the top surface 42 of the base 40 are visible through the bottom surface (i.e., from under the plate 46). A light-emitting diode (LED) panel 50 is coupled to the bottom of the plate 46 and configured to illuminate the objects resting on the top surface 42 of the base through the transparent base 40. In the illustrative embodiment, the LED panel emits red light that is sufficiently diffuse to minimize reflectance and has variable intensity that may be controlled by an electronic controller 400 (see FIG. 14), as described in greater detail below.

Each seed carrying plate 36 has a bin 44 defined therein that receives the seeds 12. The dock 22 includes a plurality of posts or guide pins 48 that surround the circular base 40. As shown in FIG. 3, the pins 48 extend upwardly from the plate 46 and are designed to support and/or secure the plate 36 on the base 40. In other embodiments, the dock 22 may include other supporting structure to guide, support, and/or secure the plate 36 on the base 40.

As indicated above, the system 10 is configured to locate the seeds 12 on a plate 36 when the plate 36 is positioned on the delivery area 24 or, more specifically, when the plate 36 is positioned on the base 40. In the illustrative embodiment, a camera 52 is positioned above the delivery area 24, as shown in FIG. 1. The camera 52 is electrically coupled to the electronic controller 400 (see FIG. 14) and is operable to capture images of the plate 36 and seeds 12. As described in greater detail below, the images are sent to the controller 400 to determine the relative locations and orientations of the seeds 12 on the plate 36 such that the system 10 can direct the robotic arm 16 to the seeds for processing. The camera 52 may be embodied as any device suitable for capturing images, such as a still camera, a video camera, or other device capable of capturing video and/or images. Further, it will be appreciated that an image captured by a camera may be described as a projection of the scene in the field of view of the camera (e.g., the foreground objects and background) onto a plane perpendicular to the optical axis of the camera.

Returning to FIG. 2, the dock 22 also includes a pair of receiving areas 26 where seeds 12 may be positioned after processing by the system 10. Like the delivery areas 24, each receiving area 26 includes a plurality of posts or guide pins 48 that define an area sized to receive one of the plates 38.

Each pin 48 extends upwardly from the plate 46, and the pins 48 cooperate to support and/or secure the plate 38 in the receiving area 26.

Figure 4:
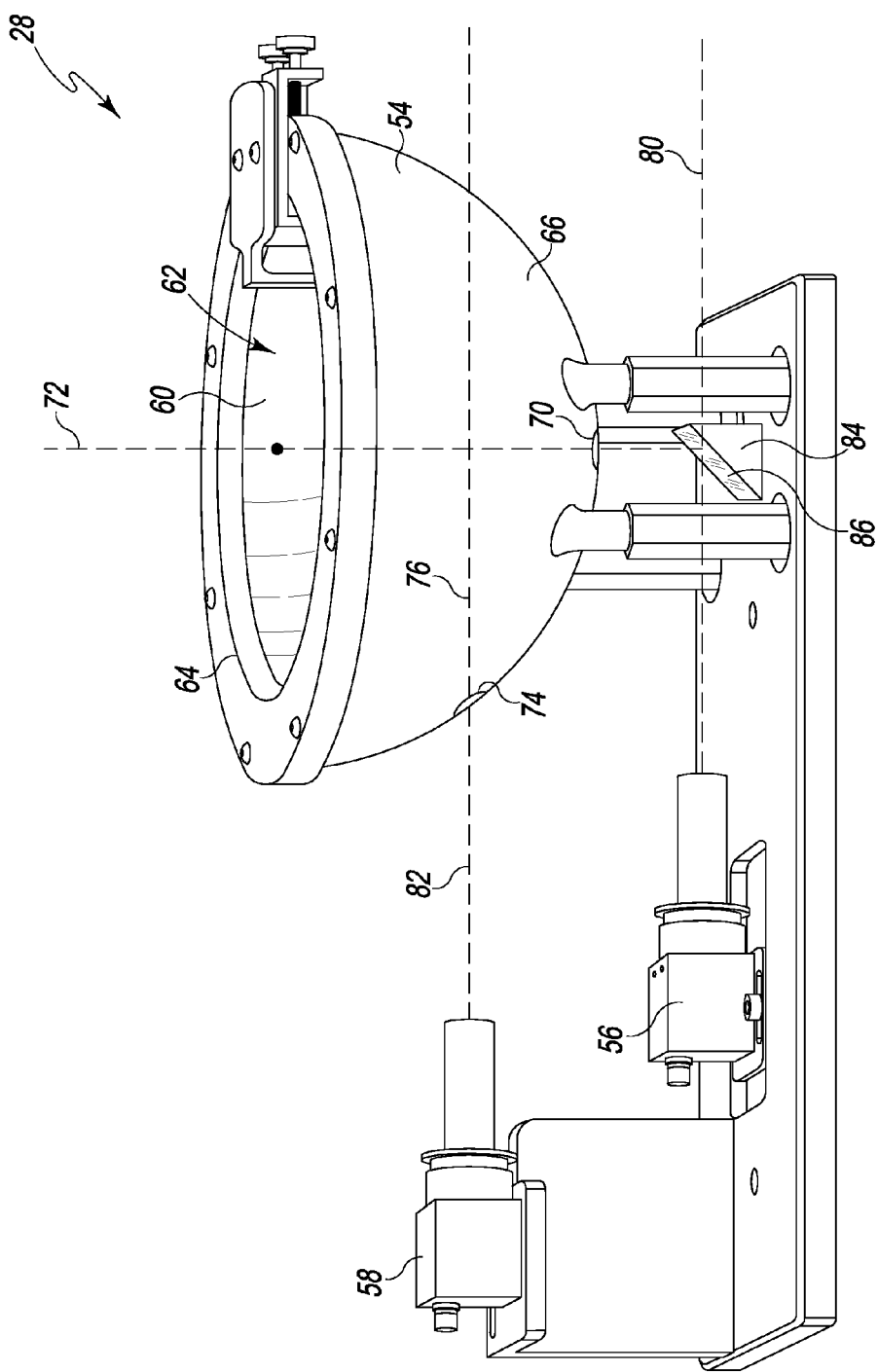
FIG. 4 is a perspective view of an imaging station of the system of FIG. 2.
Figure 5:
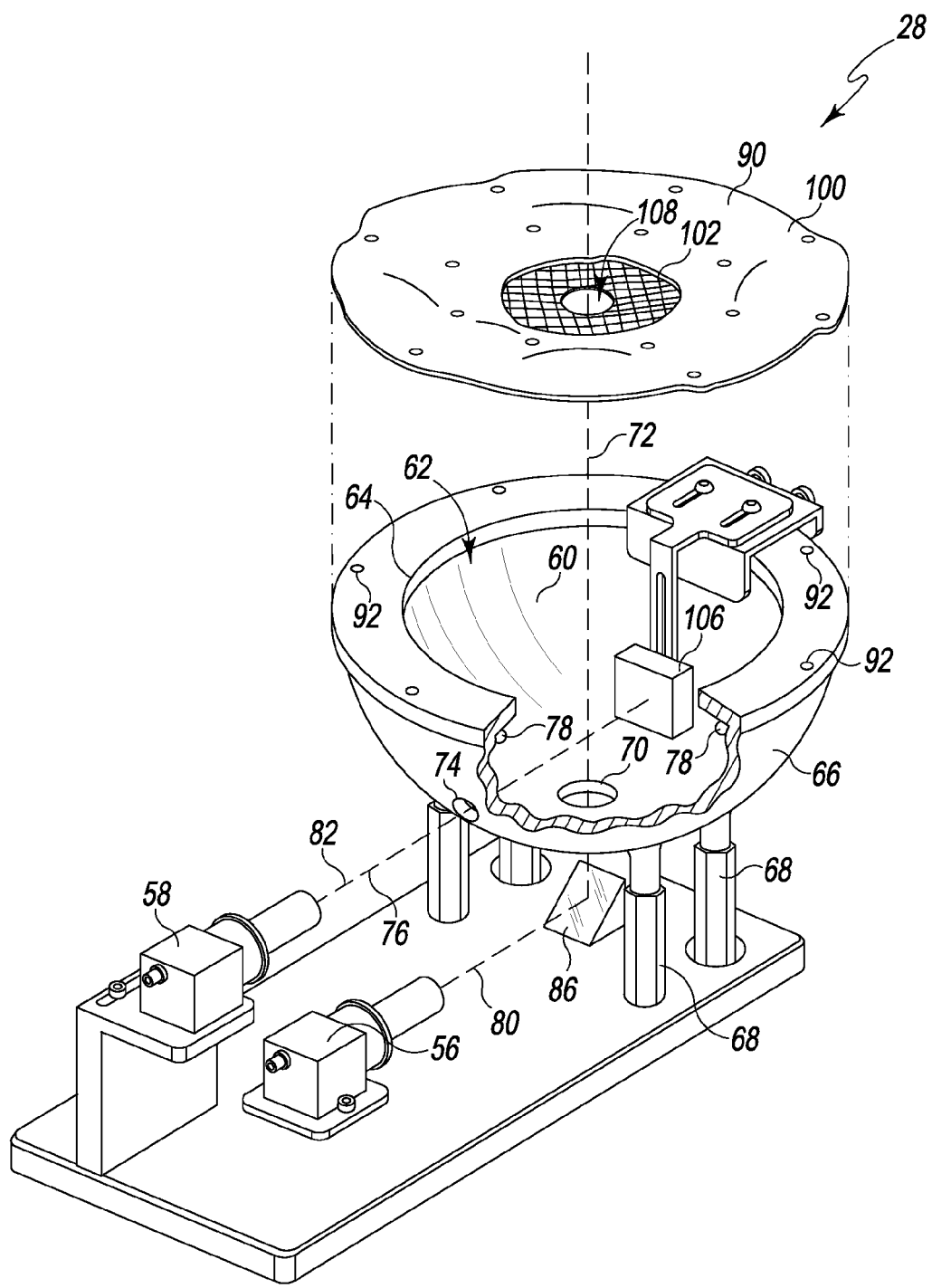
FIG. 5 is an exploded perspective view of the imaging station of FIG. 4.

As described above, the system 10 also includes an imaging station 28 that is operable to capture a number of images of the seeds 12, which used to determine the cutting planes for each seed 12. Referring now to FIGS. 4-5, the imaging station 28 includes a lighted dome 54 and two cameras 56, 58 that are secured to the table 20. The camera 56, 58 are electrically coupled to the electronic controller 400 (see FIG. 14) and are operable to capture images of the inner chamber 62 of the dome 54. In the illustrative embodiment, the lighted dome 54 is an eight-inch diameter white LED dome light manufactured by Advanced Illumination of Rochester, Vt. The lighted dome 54 includes a concave interior wall 60 that defines the bowl-shaped chamber 62 and a circular opening 64 that permits access to the chamber 62.

As shown in FIG. 5, the dome 54 also includes a plurality of LEDs 78 coupled to the wall 60 to light the chamber 62 during operation. In the illustrative embodiment, the LEDs 78 are formed as a ring of approximately 20 LEDs, which are sufficiently diffused to prevent reflections onto objects within the dome 54 and may be controlled by the controller 400 to vary the intensity of light emitted from the LEDs 78. The ring is mounted around the upper inside edge of the dome 54. It should be appreciated that in other embodiments other lighting sources may be used.

The dome 54 includes a convex exterior wall 66 and a plurality of legs 68 that extend downwardly from the wall 66 to the table 20. The dome 54 has a lower opening 70 extending through the walls 60, 66 at the apex of the convex exterior wall 66. In the illustrative embodiment, a central axis 72 extends through the centers of the upper opening 64 and the lower opening 70. Another opening 74 extends through the walls 60, 66 on the side of the dome 54 facing the cameras 56, 58. The opening 74 has a longitudinal axis 76 that extends orthogonal to the central axis 72.

Each of the cameras 56, 58 may be embodied as any device suitable for capturing images, such as a still camera, a video camera, or other device capable of capturing video and/or images. The cameras 56, 58 include optical axes 80, 82, respectively, which are aligned with the openings 70, 74 of the dome 54. In the illustrative embodiment, the optical axes 80, 82 are parallel to one another and perpendicular to the central axis 72 of the dome 54. As shown in FIGS. 4-5, the longitudinal axis 76 of the opening 74 is coincident with the axis 82 of the camera 58. Additionally, in some embodiments, each of the cameras 56, 58 may include a lens and be positioned such that, in a captured image of a seed 12 positioned within the lighted dome 54, the seed 12 is within at least half of the field of view of the corresponding camera 56, 58.

The imaging station 28 includes an angled mirror 84 that is positioned below the lower opening 70 of the dome 54. The angled mirror 84 is configured to reflect light from the chamber 62 toward the camera 56. In the illustrative embodiment, the surface 86 of the mirror 84 is angled at a forty-five degree angle relative to each of the central axis 72 and an optical axis 80 of the camera 56. As a result, light from the chamber 62 is reflected along the optical axis 80 toward the camera 56. It should be appreciated that in other embodiments the mirror may be omitted and the camera 56 positioned directly below the dome 54. Additionally, in other embodiments, the camera 58 may be positioned adjacent to another side of the dome 54. In still other embodiments, one of the cameras 56, 58 may be omitted.

In the illustrative embodiment, the imaging station 28 includes additional components to reduce the incidence of stray light entering the dome 54 and improve the quality of imaging performed at the imaging station 28. For example, a cover 90 positioned over the circular opening 64 of the dome 54 to reduce the chance that stray light (e.g., from the environment of the imaging station 28) enters the dome 54. As shown in FIG. 5, the dome 54 includes a plurality of threaded bores 92 defined in the rim 94 of the dome 54. Each bore 92 is sized to receive a corresponding fastener 96 to secure the cover 90 to the dome 54.

The cover 90 includes a fabric sheet 100 that is secured to a pad 102. The pad 102 is formed from a high-temperature flexible silicon pad. In the illustrative embodiment, the pad 102 is black such that it functions as a contrasting background to improve the quality of images captured by the camera 56. It should be appreciated that in other embodiments the pad may be made in another contrasting color. In still other embodiments, the pad and/or cover may be omitted from the imaging station 28. As shown in FIG. 5, the cover 90 has a central opening 108 that permits the robotic arm 16 to advance a seed 12 into the dome 54.

Another component to improve the quality of imaging is a backstop 106 secured to the dome 54. As shown in FIG. 5, the backstop 106 is positioned within the chamber 62 of the dome 54. The backstop 106, like the pad 102, is configured to serve as a contrasting background for images of the seed 12 captured by the camera 58. It should be appreciated that in other embodiments the backstop may be made in another contrasting color. In still other embodiments, the backstop may be omitted from the imaging station 28. In yet other embodiments, the imaging station 28 may include an environment for capturing images of the seeds 12 in addition or alternatively to the lighted dome 54 such as, for example, another lighted hollow-bodied structure, a planar monochromatic backdrop, or some other suitable imaging environment.

Figure 6:
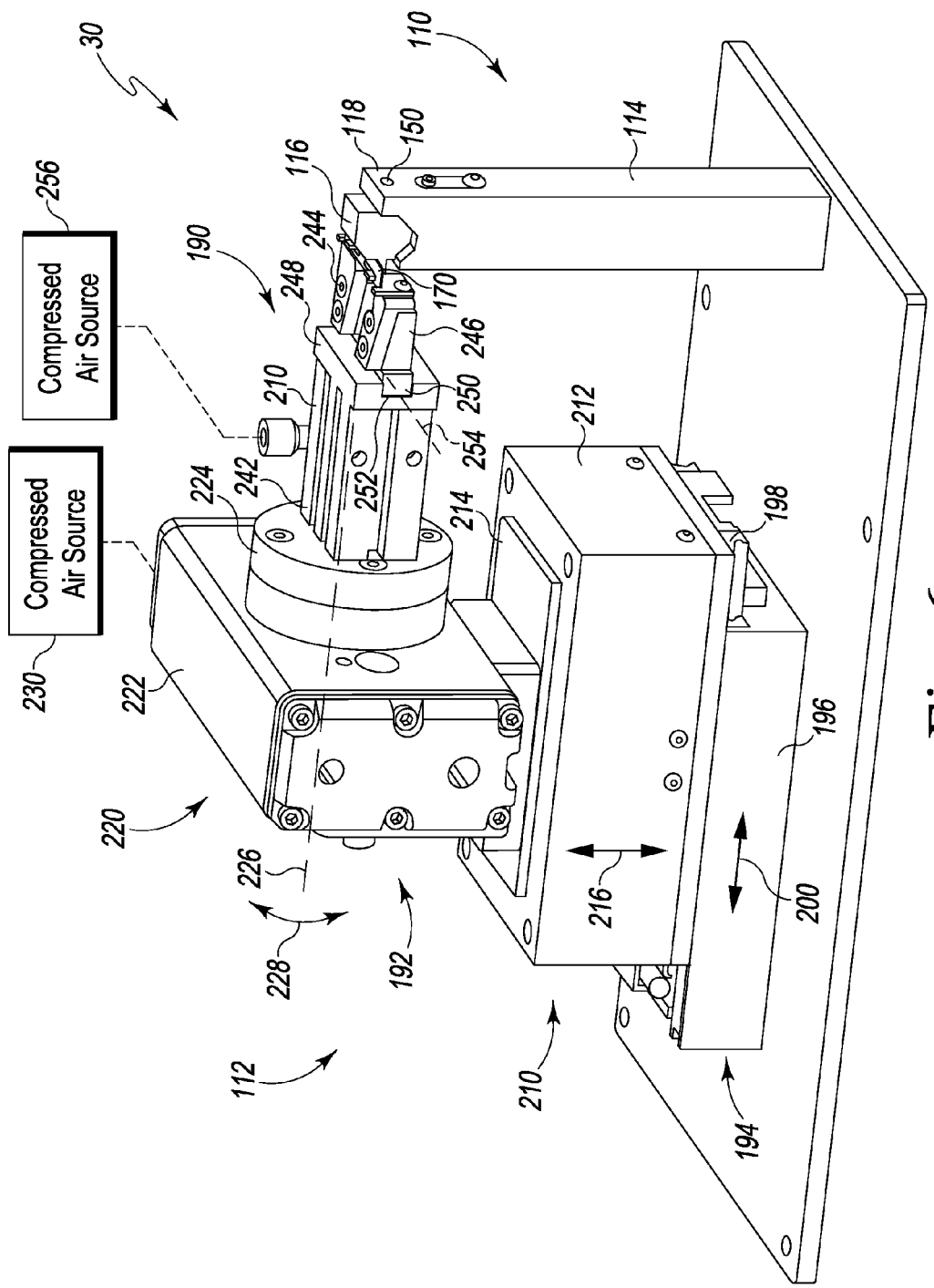
FIG. 6 is a perspective view of a cutting device of the system of FIG. 2.

As described above, the system 10 also includes a cutting station 30 that is operable to cut each seed 12 based on the images captured by the station 28. Referring now to FIG. 6, the cutting station 30 includes a platform 110 and a cutting device 112 operable to cut the seed 12 on the platform 110. The platform 110 includes a pedestal 114 that extends upwardly from the table 20 and a seed cutting block 116 secured to the upper end 118 of the pedestal 114. The pedestal 114 is formed from a metallic material such as, for example, stainless steel or aluminum. In the illustrative embodiment, the cutting block 116 is formed from a magnetic metallic material such as, for example, stainless steel. It should be appreciated that in other embodiments the pedestal and/or cutting block may be formed from other rigid materials such as plastics, Teflon, or ceramics.

Figure 7:
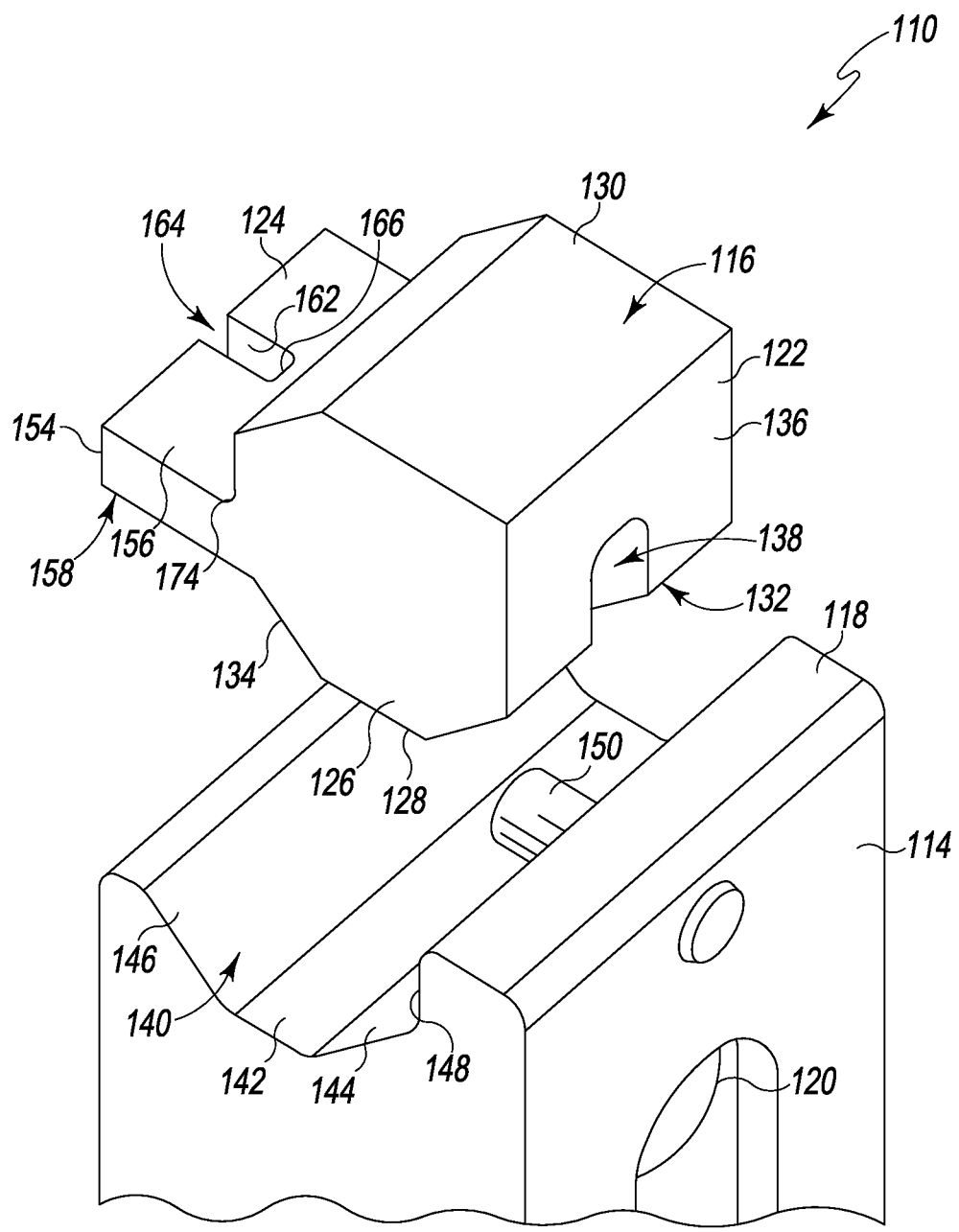
FIG. 7 is an exploded perspective view of a cutting block of the cutting device of FIG. 6.

As shown in FIG. 7, the cutting block 116 is configured to be removed from the pedestal 114 for sterilization or repair. In the illustrative embodiment, the pedestal 114 includes a permanent magnet 120 that is positioned adjacent to the upper end 118. When the cutting block 116 is positioned on the pedestal 114, the magnet 120 exerts a force to retain the cutting block 116 on the pedestal 114. It should be appreciated that the magnet is not required to retain the block 116 on the pedestal 114. In the illustrative embodiment, the design of the pedestal 114 is sufficient to retain the block 116 thereon.

In the illustrative embodiment, the cutting block 116 has a body 122 and a flange 124 that extends outwardly from the body 122. The lower end 126 of the body 122 has a substantially planar bottom surface 128, and the body 122 has a substantially planar top surface 130. A pair of angled surfaces 132, 134 extend upwardly from the bottom surface 128. The angled surface 132 is connected to a back surface 136, which extends vertically to the top surface 130. As shown in FIG. 7, the angled surface 132 and the back surface 136 have a slot 138 defined therein.

As shown in FIG. 7, a groove 140 is defined in the upper end 118 of the pedestal 114, and the groove 140 is configured to receive the lower end 126 of the block body 122. In the illustrative embodiment, the groove 140 is defined by a substantially planar surface 142 and a pair of angled surfaces 144, 146 that extend upwardly from the surface 142. In that way, the configuration of the groove 140 substantially matches the configuration of the lower end 126 of the block body 122.

The pedestal 114 also includes a rear wall 148 that faces the back surface 136 of the cutting block 116 when the block 116 is positioned in the groove 140. An alignment pin 150 extends outwardly from the rear wall 148. The alignment pin 150 is sized to be received in the slot 138 defined in the block 116 to ensure the cutting block 116 is properly positioned on the pedestal 114.

Figure 8:
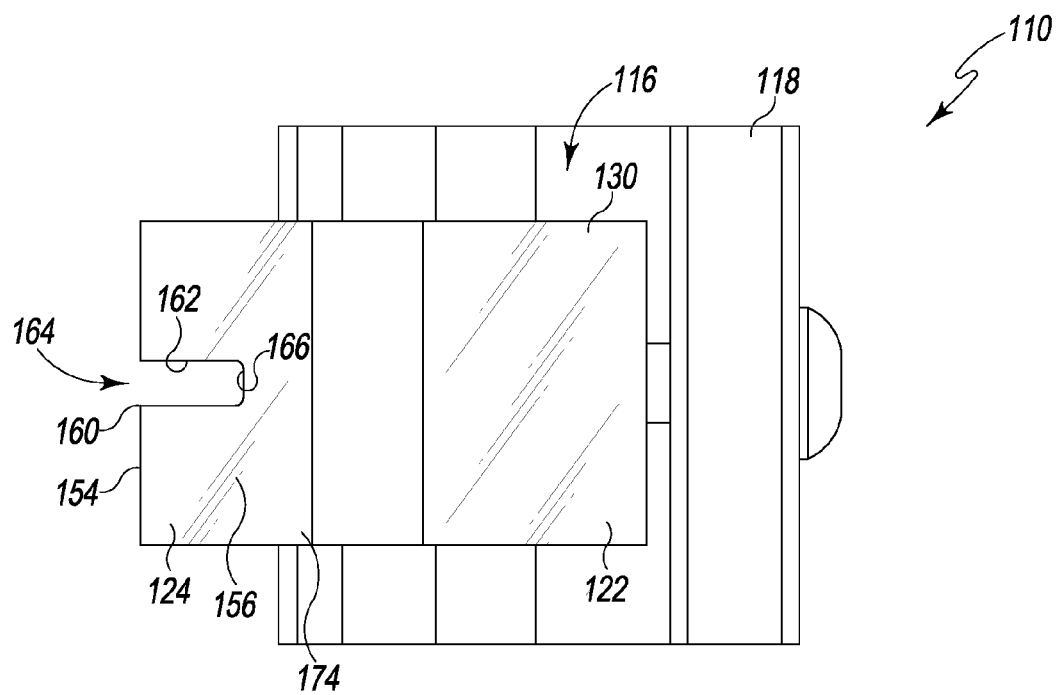
FIG. 8 is a top plan view of the cutting block of FIG. 7.

As shown in FIGS. 7-8, the flange 124 of the cutting block 116 extends outwardly from the body 122 to a front wall 154. The flange 124 includes a substantially planar upper wall 156 and a substantially planar lower wall 158 that is positioned opposite the upper wall 156. The upper wall 156 is sized to receive a soybean seed 12. It should be appreciated that in other embodiments the upper wall 156 may be resized according to the size of the seed to be cut.

An opening 160 is defined in the front wall 154. A plurality of inner walls 162 extend inwardly from the front wall 154 of the flange 124 to define a slot 164 through each of the wall 156, 158. As shown in FIG. 8, the slot 164 is centered in the flange 124, and extends to a back edge 166 positioned between a rear edge 174 of the flange 124 and the front wall 154. As described in greater detail below, the slot 164 is sized to receive a cutting blade 170 when the blade is rotated vertically.

Figure 9:
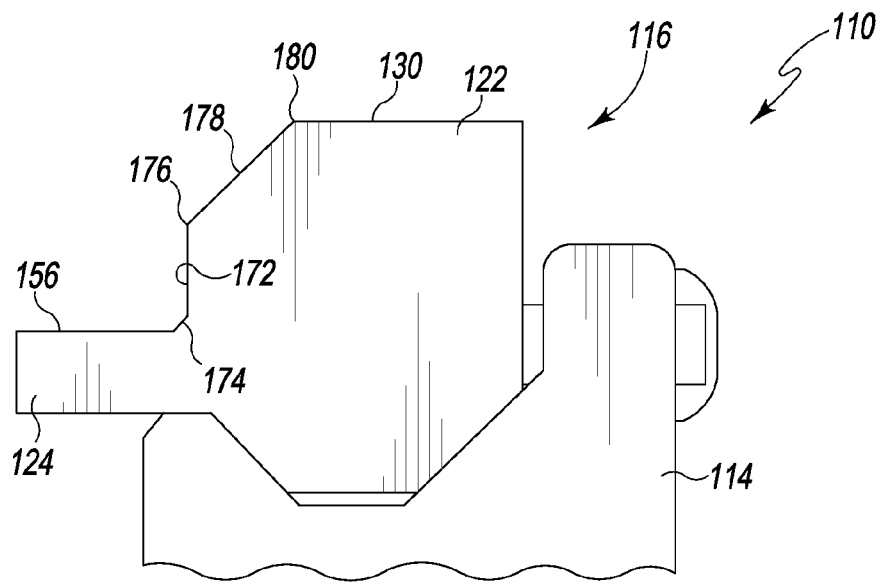
FIG. 9 is a side elevation view of the cutting block of FIGS. 7-8.

As shown in FIG. 9, the block body 122 has a substantially planar side wall 172 that extends upwardly from the rear edge 174 of the flange 124 to an upper edge 176. In the illustrative embodiment, the side wall 172 extends orthogonal to the upper wall 156. Another side wall 178 is connected to the upper edge 176 of the side wall 172. The side wall 178 extends obliquely relative to the walls 156, 172 to a top edge 180 connected to the top surface 130 of the block 116.

Returning to FIG. 6, the cutting station 30 also includes a cutting device 112 that is operable to cut the seed 12 on the platform 110. The cutting device 112 includes a support arm 190 configured to receive a cutting blade 170 and a drive assembly 192 configured to move the cutting blade 170 during the cutting operation. The drive assembly 192 includes a drive stage 194 that is secured to the table 20. The drive stage 194 includes a lower body 196 and an upper body 198 configured to slide relative to the lower body 196 in the direction indicated by arrows 200 in FIG. 6. The drive stage 194 includes a linear drive electric motor (not shown) that is electrically connected to the controller 400 and is operable to move the upper body 198 relative to the lower body 196. In the illustrative embodiment, the drive stage 194 is an Aerotech model ANT95-50-L that has approximately 50 millimeters of travel.

The drive assembly 192 of the cutting device 112 includes an intermediate drive stage 210 that travels with the drive stage 194. The intermediate drive stage 210 includes a base 212 that is connected to the upper body 198 of the drive stage 194. The drive stage 210 also includes a platform 214 that is moveably coupled to the base 212. In the illustrative embodiment, the platform 214 is configured to move vertically in the direction indicated by arrows 216 in FIG. 6. The drive stage 210 also includes a linear drive electric motor (not shown) that is electrically connected to the controller 400 and is operable to move the platform 214 relative to the base 212. The drive stage 210 is illustratively embodied as Aerotech model ANT95-3-V, which has approximately 3 millimeters of travel.

As shown in FIG. 6, the drive assembly 192 includes a rotational stage 220 that travels with the other stages 194, 210. The rotational stage 220 includes a main body 222 that is connected to the platform 214 of the drive stage 210. The rotational stage 220 also includes a mounting shaft 224 that is pivotally coupled to the main body 222. An axis 226 is defined by the mounting shaft 224, and the shaft 224 is configured to rotate about the axis 226 in the directions indicated by arrows 228. In the illustrative embodiment, the rotational stage 220 is connected to a source 230 of compressed air such as, for example, a compressor. The source 230 is electrically connected to the controller 400. When operated by the controller 400, the source 230 may advance compressed air to the stage 220 such that the shaft 224 is driven pneumatically about the axis 226. The rotational stage 220 is illustratively embodied as an EMI Plastics Equipment Swiveling Rotary, type RT25.

The support arm 190 of the cutting device 112 is secured to the rotational stage 220. As shown in FIG. 6, the support arm 190 includes an elongated body 240 that has an end 242 secured to the mounting shaft 224 of the stage 220. The support arm 190 also includes a pair of jaws 244, 246 that are secured to the opposite end 248 of the body 240. In the illustrative embodiment, each of the jaws 244, 246 has an end 250 that is received in a channel 252 defined in the elongated body 240. The channel 252 defines a longitudinal axis 254, and the jaws 244, 246 are configured to move along the channel 252 toward and away from each other. In that way, the jaws 244, 246 may be opened or closed. In the illustrative embodiment, the support arm 190 is connected to a source 256 of compressed air. The source 256 is electrically connected to the controller 400. When operated by the controller 400, the source 256 may advance compressed air to the support arm 190 such that the jaws 244, 246 are driven pneumatically along the channel 252. The support arm 190 is illustratively embodied as an SMC MHZ2-20C1-M9PZ gripper.

Figure 10A:
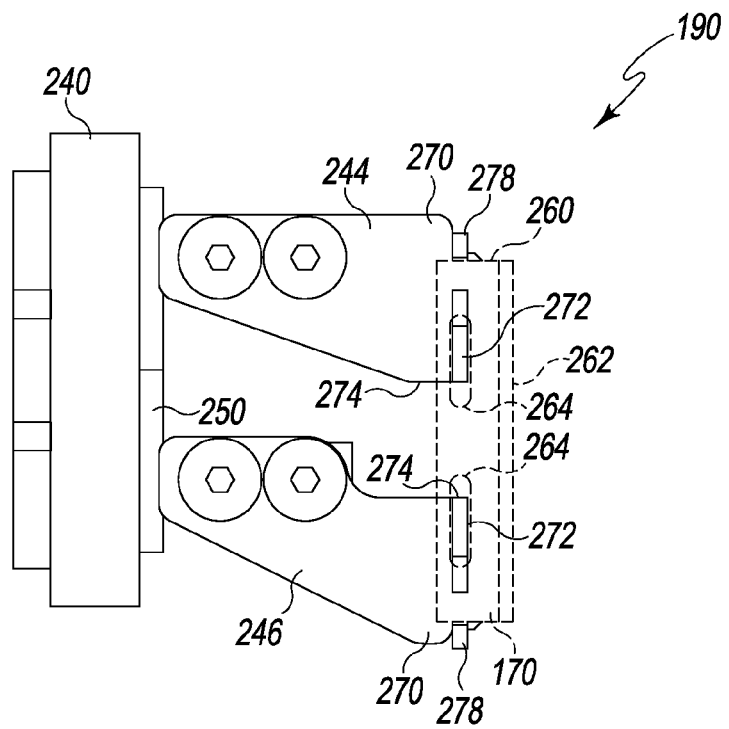
FIG. 10A is a top plan view of the cutting device of FIG. 6 showing the jaws in a disengaged position.
Figure 11A:
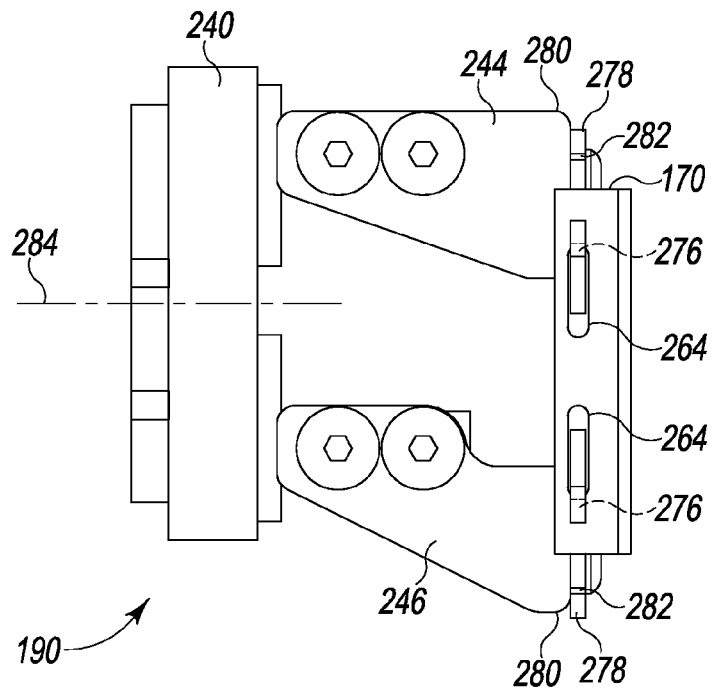
FIG. 11A is a view similar to FIG. 10A showing the jaws in an engaged position.
Figure 10B:
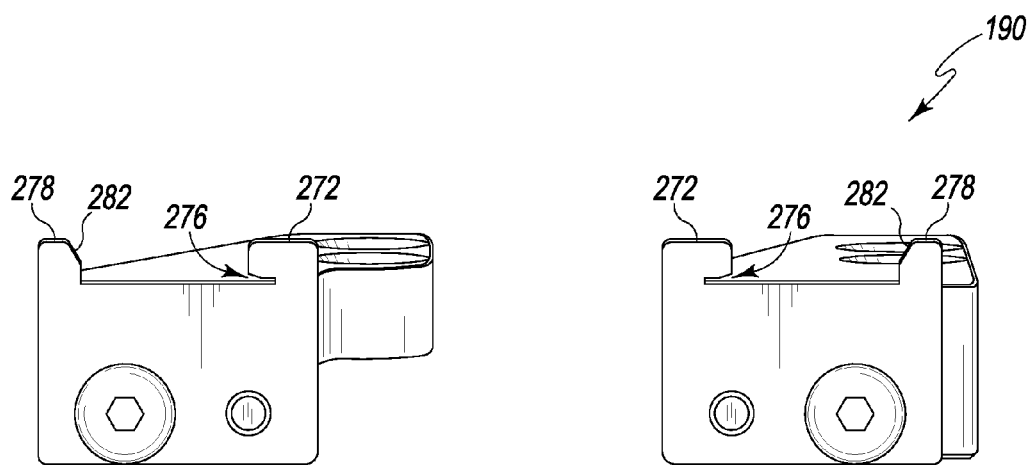
FIG. 10B is a front perspective view of the cutting device of FIG. 6 showing the jaws in a disengaged position.
Figure 11B:
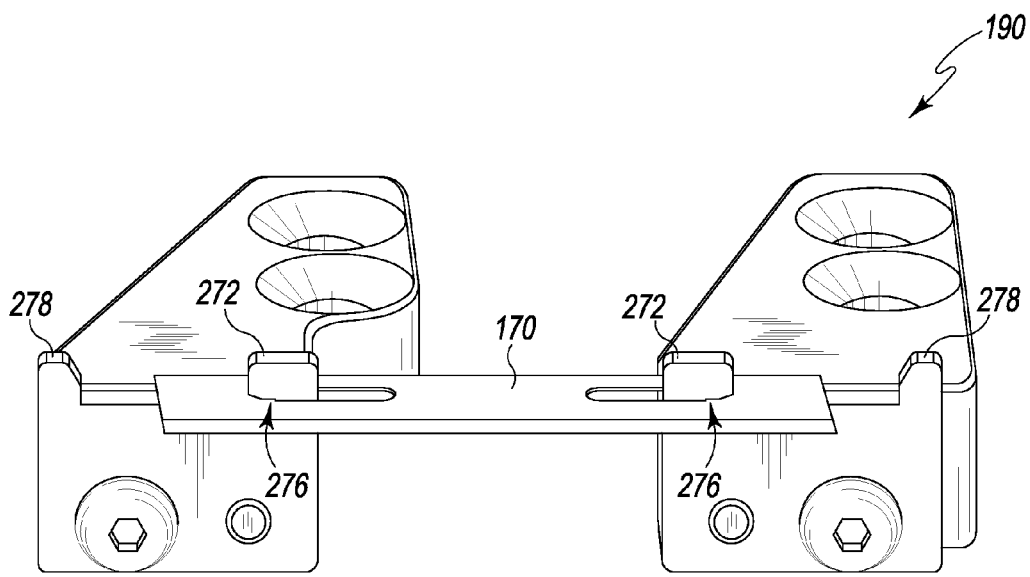
FIG. 11B is a view similar to FIG. 10B showing the jaws in an engaged position.

The jaws 244, 246 are configured to receive a cutting blade 170. Referring now to FIGS. 10-11, each cutting blade includes a body 260 and a cutting edge 262 extending the length of the body 260. The cutting edge 262 is offset from the axis of rotation 226 when the cutting blade 170 is secured to the jaws 244, 246. The body 260 also includes a pair of oblong mounting holes 264, which are engaged by the jaws 244, 246 to secure the cutting blade 170 to the device 112. The cutting blade 170 is illustratively formed from a metallic material such as steel.

Each of the jaws 244, 246 extends from the end 250 to a tip 270. Each of the jaws 244, 246 includes an inner tab 272 positioned along an inner edge 274 of the tip 270. Each tab 272 is sized to be positioned in one of the holes 264 of a cutting blade 170. In the illustrative embodiment, each of the jaws 244, 246 also includes a slot 276 (see FIG. 10B) that is formed at the base of each tab 272. In the illustrative embodiment, each slot is configured to capture the blade and hold it level. As shown in FIGS. 11A and B, the blade 170 is advanced into the slots 276 when the jaws 244, 246 are moved apart, thereby securing the blade to the jaws 244, 246. Each of the jaws 244, 246 also includes an outer tab 278 that is positioned along an outer edge 280 of the tip 270. The outer tab 278 includes a beveled edge 282 to assist with alignment of the blade 170 as it is inserted onto the jaws 244, 246.

As shown in FIG. 11A, the elongated body 240 of the support arm 190 has a longitudinal axis 284. In the illustrative embodiment, the cutting blade 170 is offset from the axis 284 when secured to the jaws 244, 246. During operation, the offset of the cutting blade 170 from the axis 284 lowers the cutting blade 170 to reduce the risk that the cutting blade will contact the robotic arm when cutting the soybean seed.

Figure 12:
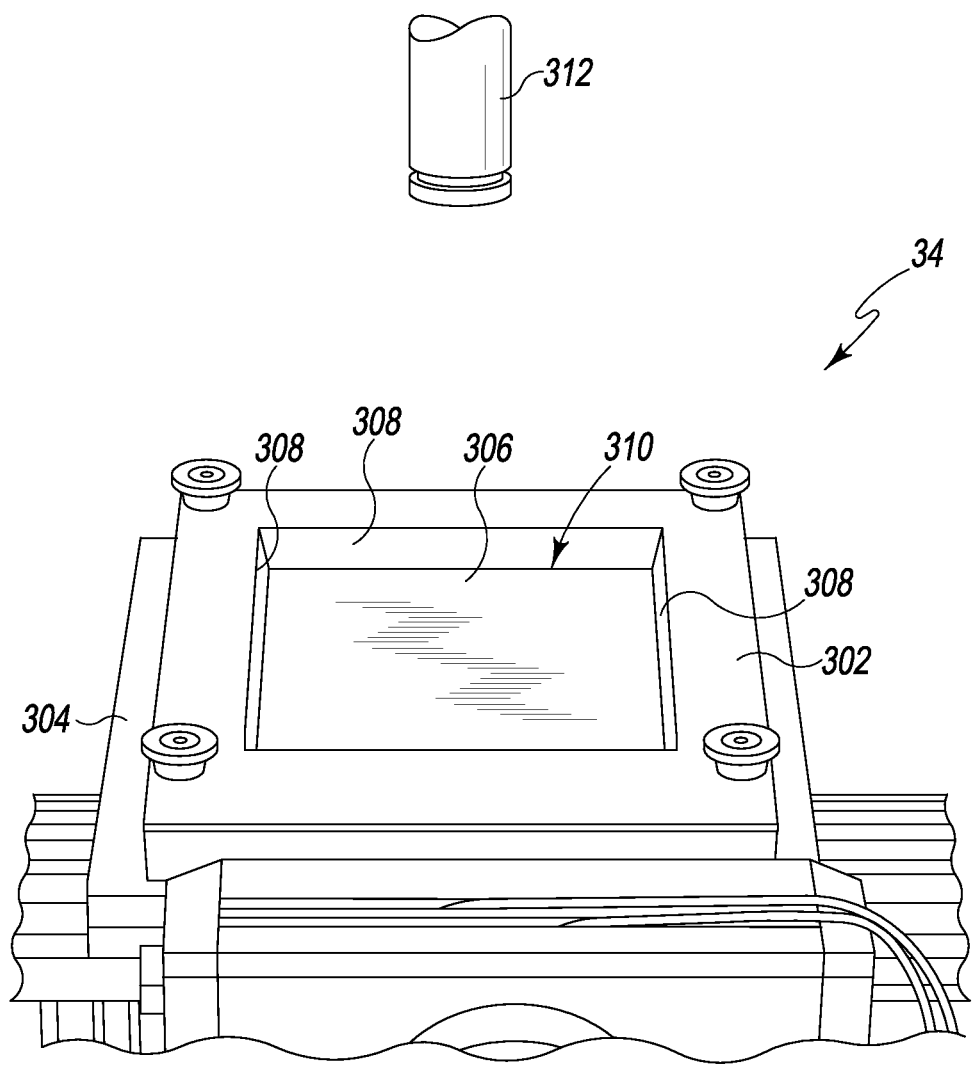
FIG. 12 is a perspective view of a cutting tool tray of the system of FIG. 1.

Referring now to FIG. 12, a tray 34 for holding unused cutting blades 170 is positioned between the robotic arms 16. The tray 34 includes a container 302 positioned above a light source 304. The container 302 is illustratively formed from a transparent material such as, for example, Plexiglas. The container 302 includes a bottom wall 306 and a plurality of side walls 308 that extend upwardly from the bottom wall 306. The walls 306, 308 cooperate to define a chamber 310 sized to receive unused cutting blades 170.

In the illustrative embodiment, the light source 304 of the tray 34 is positioned below the bottom wall 306. The light source 304 is operable to project light through the bottom wall 306 into the chamber 310. The light source 304 is illustratively embodied as a red light-emitting diode (LED). It should be appreciated that in other embodiments other colored LEDs may be used. In still other embodiments, other lighting sources may be used.

The system 10 includes a tray camera 312, which is mounted above the tray 34. The camera 312 is operable to capture images of the contents of the chamber 310. The camera 312 is electrically coupled to an electronic controller 400 (see FIG. 14). As described in greater detail below, the images may be sent to the controller 400 to determine the relative locations and orientations of the blades 170 in the tray 34 such that the system 10 can direct the robotic arm 16 to the blades 170 for retrieval.

Figure 13:
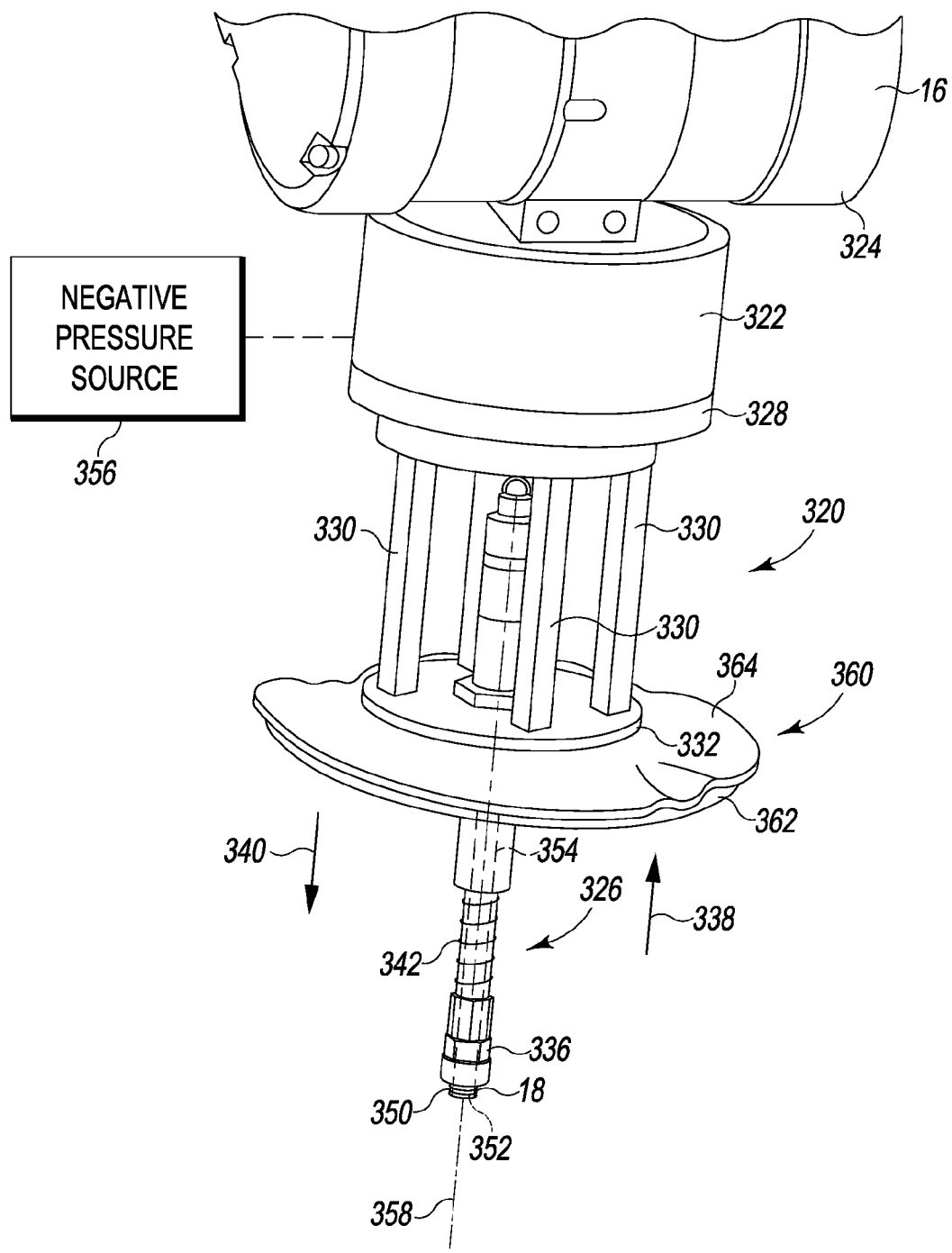
FIG. 13 is a perspective view of a grip assembly of a robotic arm of the system of FIG. 1.

Referring now to FIG. 13, each robotic arm 16 of the system 10 includes a grip assembly 320 configured to grasp and hold a soybean seed 12. In the illustrative embodiment, the grip assembly 320 includes a body 322 that is attached to a distal section 324 of each arm 16. The grip assembly 320 also includes a suspension mechanism 326 that connects the body 322 to a grip 18. The body 322 has a proximal disk 328 that is secured to the distal arm section 324 and a plurality of posts 330 that extend from the disk 328 to a distal disk 332.

The suspension mechanism 326 extends from a proximal end 334 that is secured to the disk 332 to a distal end 336. As shown in FIG. 13, the grip 18 is secured to the distal end 336 of the suspension mechanism 326. The suspension mechanism 326 is configured to permit some axial movement of the grip 18, as indicated by arrows 338, 340, such that the grip 18 may be advanced into contact with a soybean seed 12 without crushing the seed. In the illustrative embodiment, the suspension mechanism 326 includes a biasing element such as, for example, a helical spring 342, that biases the grip 18 outward, in the direction indicated by arrow 340.

The grip 18 of the assembly 320 is configured to grasp and hold a seed 12. In the illustrative embodiment, the grip 18 includes a cylindrical body 350 that is secured to the distal end 336 of the suspension mechanism 326. The body 350 is formed from an elastomeric material such as, for example, Viton, which is commercially available from DuPont Corporation. It should be appreciated that in other embodiments other elastomeric materials may be used. The body 350 includes a bellows, which provides the body 350 with limited flexibility. The body 350 also has a high temperature rating to permit sterilization of the grip 18. In the illustrative embodiment, the temperature rating is 446 degrees Fahrenheit. It should be appreciated that in other embodiments other elastomeric materials may be used.

The grip assembly 320 is configured to grasp and hold the seed 12 via vacuum. To do so, the grip 18 includes a hollow passageway 352 that extends longitudinally through the body 350 along an axis 358. The passageway 352 is connected to passageways 354 defined in the suspension mechanism 326 and the body 322 of the grip assembly 320 and a negative pressure source 356. The negative pressure source 356 is illustratively embodied as a pump and is electrically coupled to the controller 400. The controller 400 may operate the source 356 to draw a vacuum through the passageways 352, 354 and secure a seed 12 to the grip 18. In the illustrative embodiment, the grip 18 has a radius of less than fifty percent of the average length of a seed 12, which may vary depending on, for example, the particular species of the seed 12.

As shown in FIG. 13, the grip assembly 320 also includes a secondary cover 360 that is secured to the body 350. The secondary cover 360 is designed to prevent stray light from entering the lighted dome 54 during imaging of the seed 12. The cover 360 includes a bottom pad 362 formed from a black foam material and a top pad 364 that is formed from black felt. In the illustrative embodiment, the cover 360 is secured to the distal disk 332 via adhesive. It should be appreciated that in other embodiments the cover 360 may be secured with fasteners such as screws or bolts. The cover 360 has a diameter of approximately 3.5 inches, which is sufficient to enclose central opening 108 of the cover 90 of the dome 54.

Figure 14:
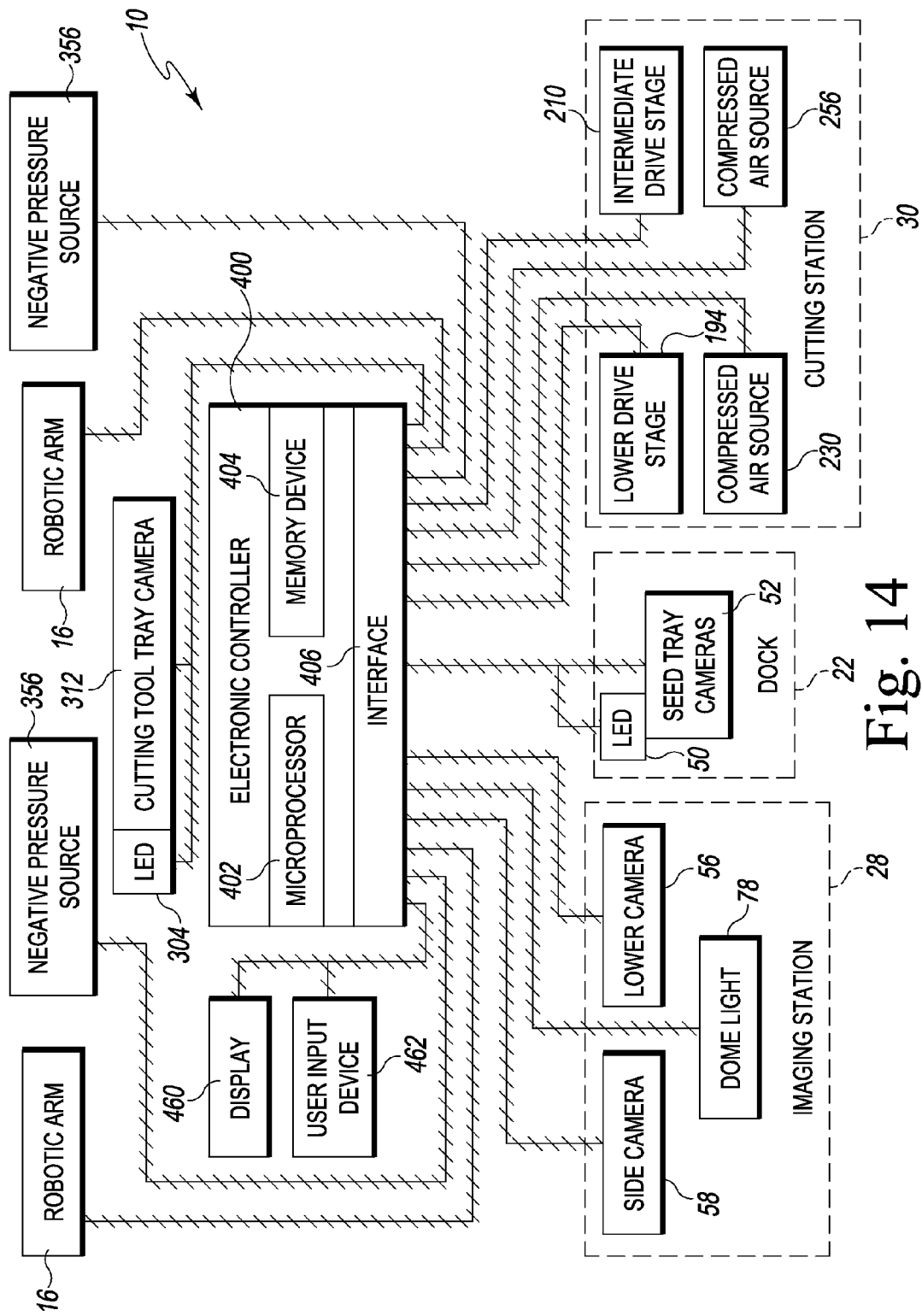
FIG. 14 is a simplified block diagram of the system of FIG. 1.

Referring now to FIG. 14, the system 10 includes an electronic controller 400. The controller 400 is, in essence, the master computer responsible for interpreting electrical signals sent by sensors associated with the system 10 and for activating or energizing electronically-controlled components associated with the system 10. For example, the electronic controller 400 is configured to control the operation of the cameras 52, 56, 58, 312, dome light 78, robotic arms 16, drive stages 194, 210, and so forth. While the electronic controller 400 is shown as a single unit in FIG. 14, the controller 400 may include a number of individual controllers for the various components as well as a central computer that sends and receives signals from the various individual controllers. The electronic controller 400 also determines when various operations of the system 10 should be performed. As will be described in more detail below, the electronic controller 400 is operable to control the components of the system 10 such that the system 10 selects and processes soybean seeds 12 for use in transgenic protocols.

To do so, the electronic controller 400 includes a number of electronic components commonly associated with electronic units utilized in the control of electromechanical systems. For example, the electronic controller 400 may include, amongst other components customarily included in such devices, a processor such as a microprocessor 402 and a memory device 404 such as a programmable read-only memory device ("PROM") including erasable PROM's (EPROM's or EEPROM's). The memory device 404 is provided to store, amongst other things, instructions in the form of, for example, a software routine (or routines) which, when executed by the microprocessor 402, allows the electronic controller 400 to control operation of the system 10.

The electronic controller 400 also includes an analog interface circuit 406. The analog interface circuit 406 converts the output signals from the various components into signals that are suitable for presentation to an input of the microprocessor 402. In particular, the analog interface circuit 406, by use of an analog-to-digital (A/D) converter (not shown) or the like, converts the analog signals generated by the sensors into digital signals for use by the microprocessor 402. It should be appreciated that the A/D converter may be embodied as a discrete device or number of devices, or may be integrated into the microprocessor 402. It should also be appreciated that if any one or more of the sensors associated with the system 10 generate a digital output signal, the analog interface circuit 406 may be bypassed.

Similarly, the analog interface circuit 406 converts signals from the microprocessor 402 into output signals which are suitable for presentation to the electrically-controlled components associated with the system 10 (e.g., the robotic arms 16). In particular, the analog interface circuit 406, by use of a digital-to-analog (D/A) converter (not shown) or the like, converts the digital signals generated by the microprocessor 402 into analog signals for use by the electronically-controlled components associated with the system 10. It should be appreciated that, similar to the A/D converter described above, the D/A converter may be embodied as a discrete device or number of devices, or may be integrated into the microprocessor 402. It should also be appreciated that if any one or more of the electronically-controlled components associated with the system 10 operate on a digital input signal, the analog interface circuit 406 may be bypassed.

Thus, the electronic controller 400 may operate to control the operation of the system 10. In particular, the electronic controller 400 executes a routine including, amongst other things, a control scheme in which the electronic controller 400 monitors the outputs of the sensors associated with the system 10 and controls the inputs to the electronically-controlled components of the system 10. To do so, the electronic controller 400 performs numerous calculations, either continuously or intermittently, including looking up values in preprogrammed tables, in order to execute algorithms to perform such functions as energizing the robotic arms 16, activating the cameras 52, 56, 58, 312, energizing the drive stages 194, 210, varying the light intensity of the LEDs 78 and LED panel 50 to improve image contrast, and so on.

In operation, the system 10 may be operated in accordance with the exemplary procedure outlined in FIGS. 15-19 to automatically select and process soybean seeds 12 for use in a transgenic protocol. For example, the soybean may be prepared by splitting the cotyledons of a seed 12 along the hilum to separate the cotyledons. Removal of a portion of the embryonic axis leaves part of the axis attached to the cotyledons prior to transformation. The removal of the embryonic axis may be made by trimming of the embryonic axis with the cutting device 112. Typically, between ⅓ and ½ of the embryo axis is left attached at the nodal end of the cotyledon As shown in FIGS. 20-29, the system 10 engages in preliminary steps to sterilize the grips 18 of the robotic arms 16, select a cutting blade 170 for the cutting station 30, and capture images of the seeds 12 located in the delivery areas 24. Thereafter, the system 10 operates one of the robotic arms 16 to pick-up a seed 12 from one of the delivery areas 24 and advance the seed 12 to the imaging station 28, as shown in FIGS. 27-31. A number of images may be captured by the imaging station 28, as shown in FIGS. 32-55, before the seed 12 is advanced to the cutting station 30. As shown in FIGS. 56-59, the cutting station 30 may be operated to make one or more cuts to the seed 12 to prepare it for transformation. The cut seed may then be advanced to one of the receiving areas 26. A user may then remove the seed from the system 10 for further processing. The system 10 may then engage in a number of cleaning and maintenance tasks before picking up and processing another seed 12.

Figure 60:
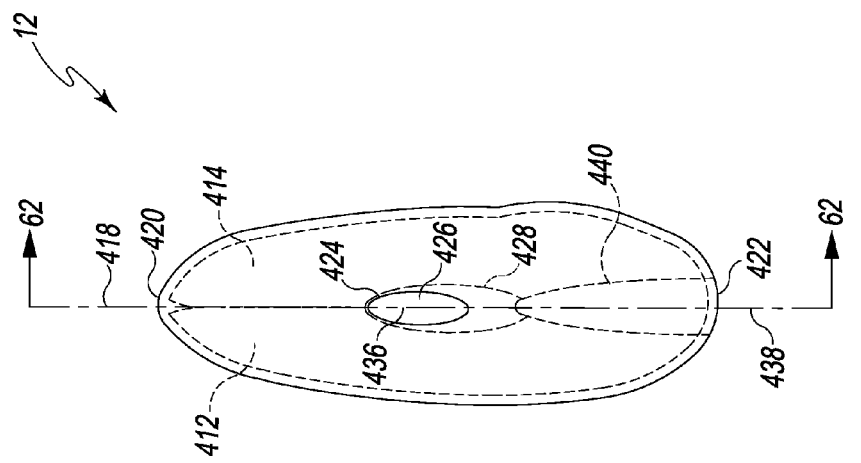
FIG. 60 is a plan view of a soybean seed.
Figure 61:
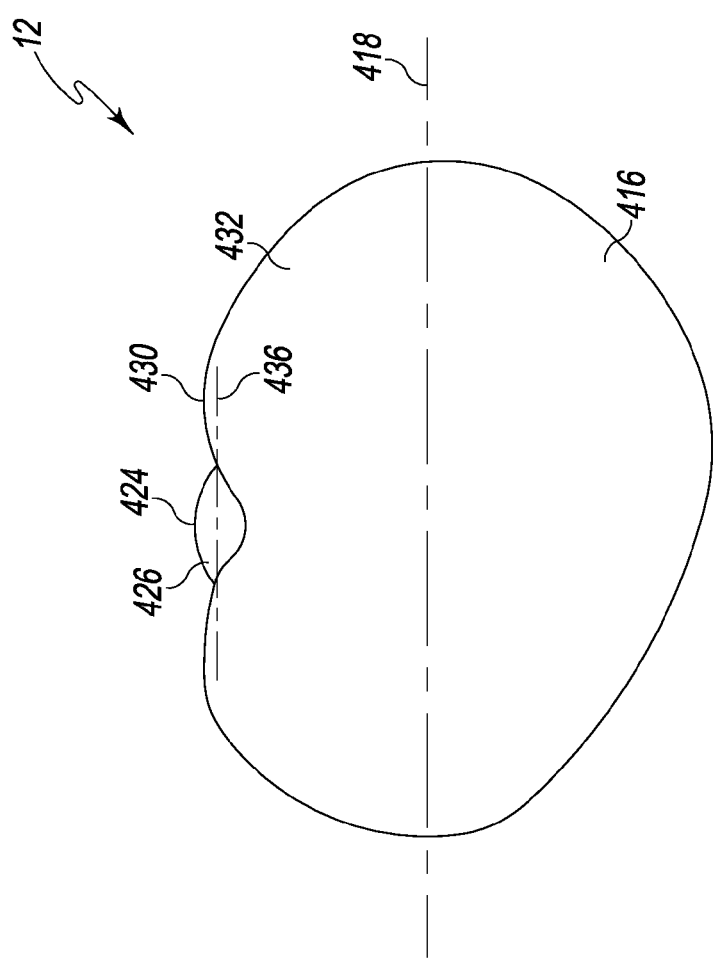
FIG. 61 is a side elevation view of the soybean seed of FIG. 60.
Figure 62:
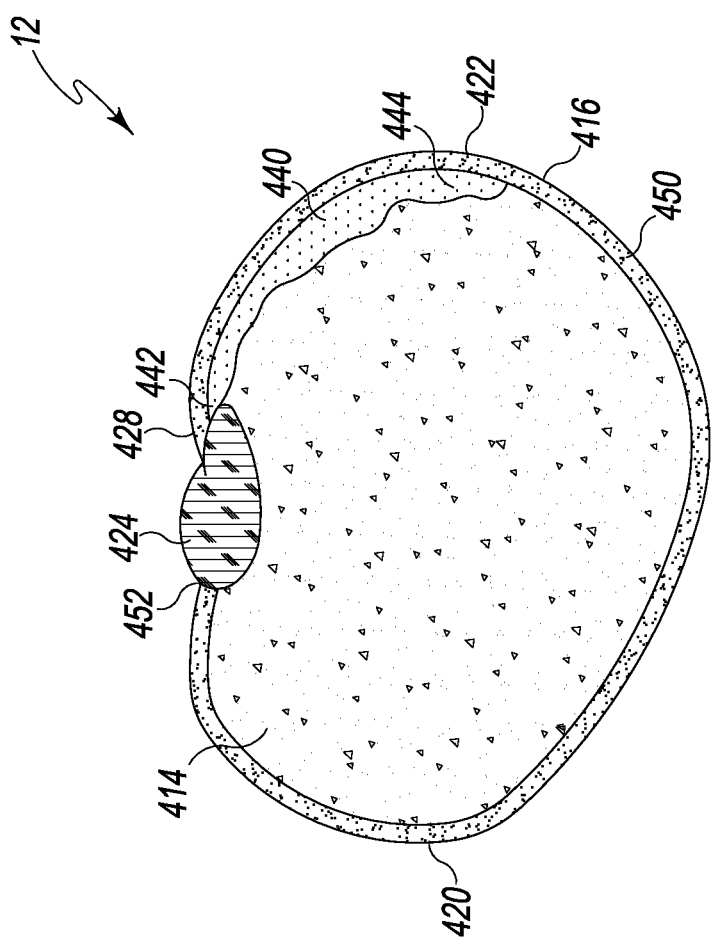
FIG. 62 is a cross-sectional elevation view of the soybean seed taken along the line 62-62 in FIG. 60.

As shown in FIG. 60-62, a soybean seed 12 includes a pair of cotyledons 412, 414, which are encased in a seed coat 416. The soybean seed 12 has a longitudinal axis 418, which is defined along its maximum dimension, and extends through opposite longitudinal ends 420, 422 of the soybean seed 12. As shown in FIG. 60, the axis 418 extends between the cotyledons 412, 414.

The soybean seed 12 also includes a hilum 424 positioned between the ends 420, 422 of the soybean seed 12. In the illustrative embodiment, the hilum 424 includes an outer section 426 that is positioned outside of the seed coat 416 and an inner section 428 that is positioned under the seed coat 416.

As shown in FIGS. 60-61, the hilum 424 is dorsally located above the cotyledons 412, 414. The outer section 426 of the hilum 424 is positioned on a dorsal side 430 of the soybean seed 12. The hilum 424 may also be viewed from the lateral side 432 (see FIG. 61) or the medial side 434 (see FIG. 5) of the soybean seed 12. As shown in FIG. 61, the hilum 424 has a longitudinal axis 436 that extends parallel to the overall longitudinal axis 418 of the seed 12. As shown in FIG. 60, the longitudinal axis 436 lies in a common plane 438 with the axis 418 of the seed 12.

An embryonic axis 440 of the soybean seed 12 connects the cotyledon 412 to the cotyledon 414. The embryonic axis 440 is encased with the cotyledons 412, 414 in the seed coat 416. As shown in FIG. 60, the embryonic axis 440, like the hilum 424, is centered on the longitudinal axis 418 of the soybean seed 12. As shown in FIG. 62, the embryonic axis 440 extends from a tip 442 positioned above the inner section 428 of the hilum 424 to a base 444 positioned adjacent to the longitudinal end 420 of the seed 12. It should be appreciated that in other embodiments the embryonic axis 440 may not overlap with the hilum 424 such that the axis tip 442 is spaced apart from the inner section 428 of the hilum.

Referring to FIG. 62, the internal structure of the soybean seed 12 is shown in greater detail. The seed coat 416 includes a thin outer layer 450 that surrounds the cotyledons 412, 414 and the embryonic axis 440. The inner section 428 of the hilum 424 is attached to the underside of the layer 450, while the outer section 426 of the hilum 424 is connected to an edge 452 of the outer layer 450. The embryonic axis 440 extends around a portion of the outer circumference of the seed 12 from its tip 442 to its base 444 positioned adjacent to the seed end 420

Figure 15:
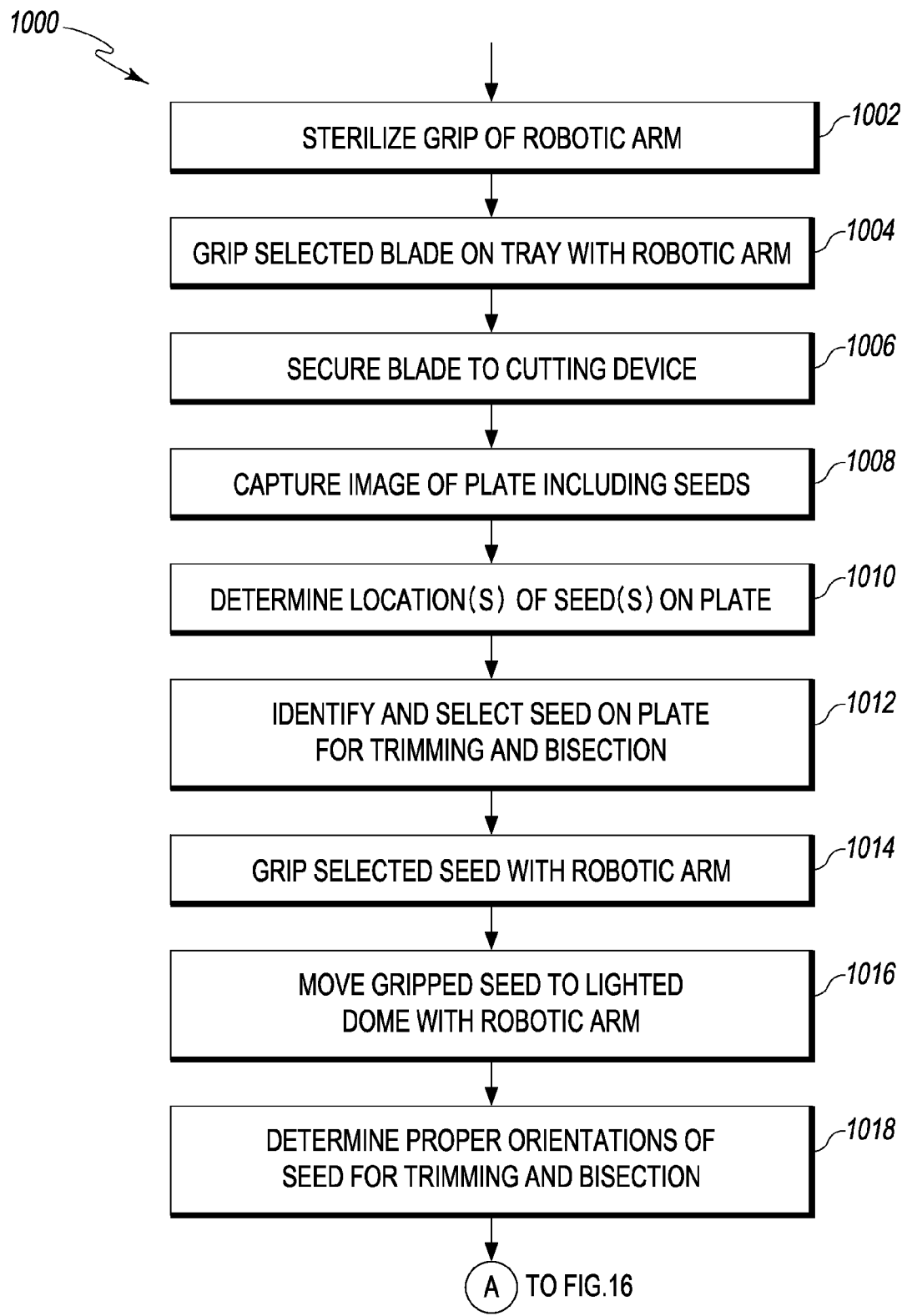
FIGS. 15-16 are block diagrams showing an illustrative operating procedure for the system of FIG. 1.
Figure 16:
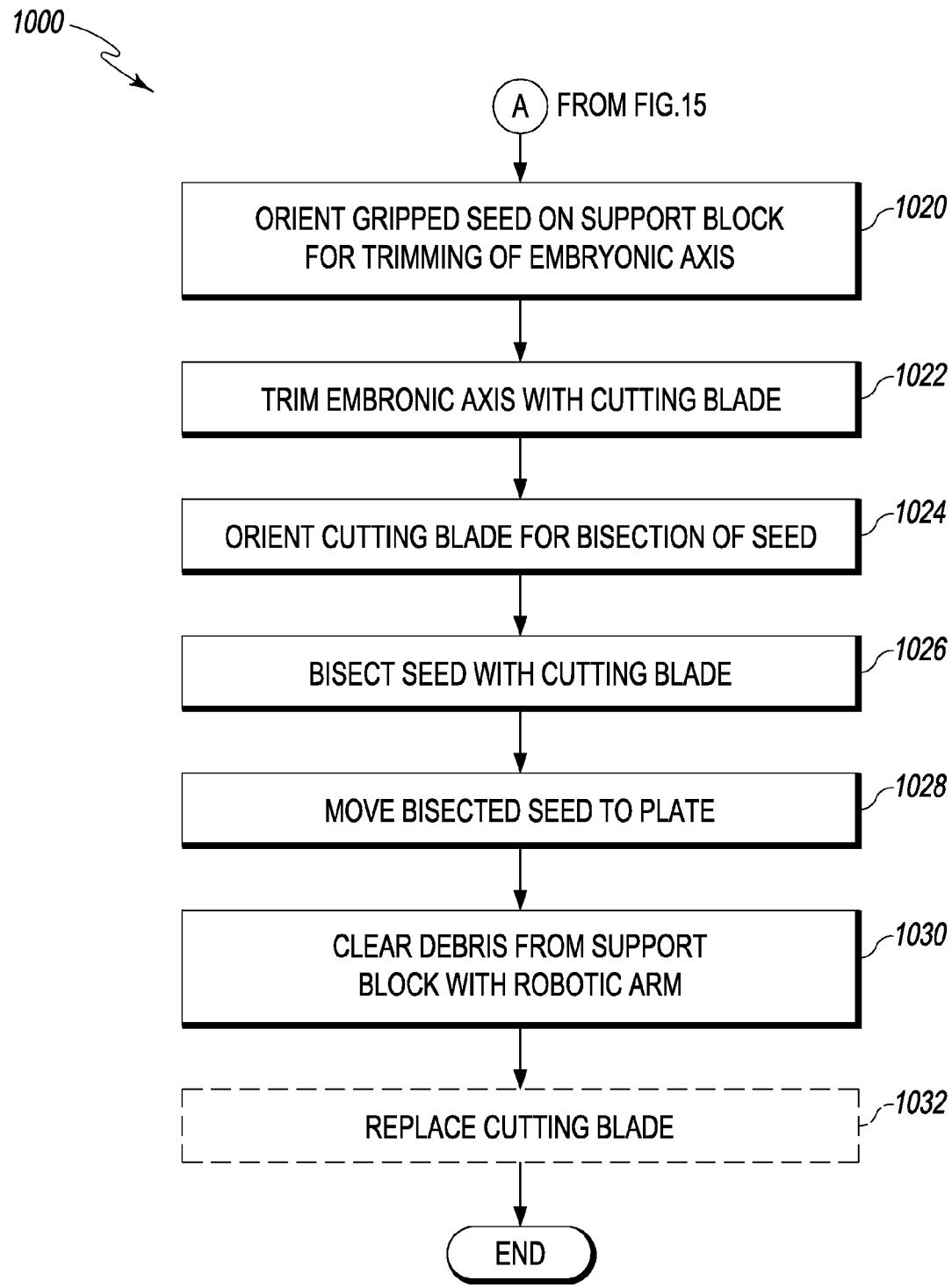

Referring now to FIGS. 15-16, an illustrative operating procedure 1000 for preparing the soybean seed 12 for transformation with the system 10 is shown. It will be appreciated that prior to commencement of the procedure 1000, the controller 400 may calibrate the system 10, provide messages to the user, retrieve user input, initialize safety mechanisms (e.g., a light curtain), and perform other setup functions. For example, if not done already, the controller 400 may calibrate the system 10 using any suitable protocol to map or otherwise correlate the coordinate system of the robotic arms 16 to the coordinate systems of the various cameras 52, 56, 58, 312 such that locations of objects captured in images may be translated to a location of that object relative to the arms 16. Further, the controller 400 may provide setup instructions to the user on a display 460 (e.g., to place the plate 36 on the delivery areas 24), retrieve input from the user via a user input device 462 (e.g., a desired trim depth of the embryonic node of the seeds 12, a bisecting depth of the seeds 12, etc.). The user input device 462 may be embodied as any integrated or peripheral device such as a keyboard, mouse, touchscreen, and/or other input devices configured to perform the functions described herein.

Figure 20:
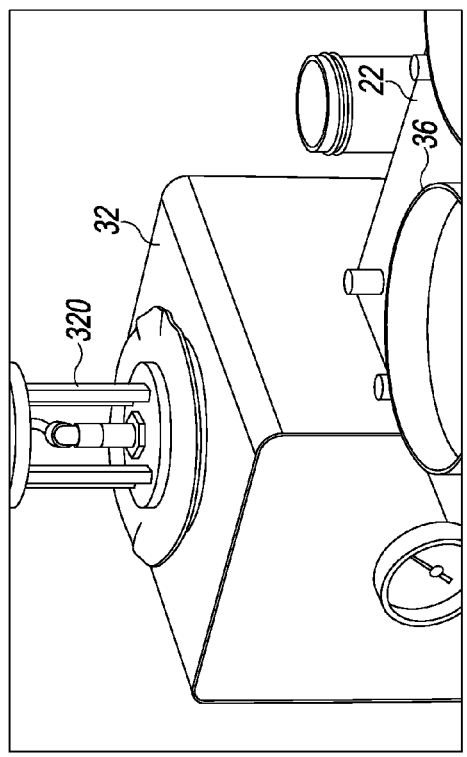
FIGS. 20-26 are illustrations of various preliminary actions in the operating procedure of FIGS. 15-16, including sterilizing the grips of the system of FIG. 1 and selecting a cutting tool.

In block 1002, the system 10 sterilizes the grips 18 of the robotic arms 16. To do so, the controller 400 operates each robotic arm 16 to insert its corresponding grip 18 into a container filled with ethanol or another suitable sterilizing solution. The solution illustratively contains 70% alcohol. The robotic arm 16 may be operated to move the grip 18 up and down and side to side within the ethanol for some period of time before advancing the grip 18 into a sterilizer 32, as shown in FIG. 20. In the illustrative embodiment, each sterilizer 32 is a dry glass bead sterilizer such as, for example, an InoTech BioScience Steri 250. The robotic arm 16 may again be operated to move the grip 18 up and down within the sterilizer 32 for a few seconds in the illustrative embodiment. The arm 16 may then withdraw the grip 18 from the sterilizer 32 such that the grip 18 is permitted to cool.

Figure 23:
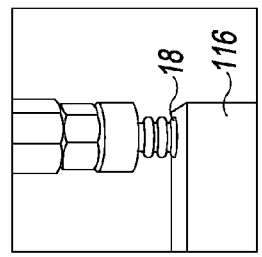
Figure 22:
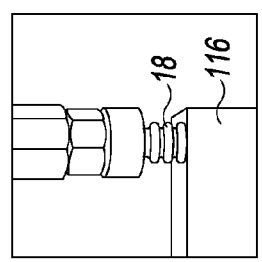
Figure 21:
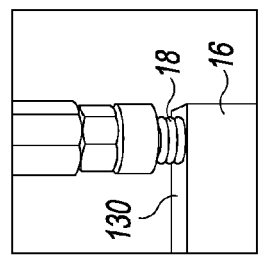

Due to the heat generated by the sterilizer 32, the bellows of the grip 18 may become stuck together such that performance of the grip 18 may be impaired. To separate the bellows, the robotic arm 16 may then move the grip 18 into contact with a flat sterile surface, such as, for example, the top surface 130 of the cutting block 116, as shown in FIG. 21. The controller 400 may then activate the negative pressure source 356 to seal the grip 18 to the cutting block 116. As shown in FIGS. 22-23, the grip 18 is moved away from the cutting block 116 in 1 mm increments until the suction is broken.

Figure 24:
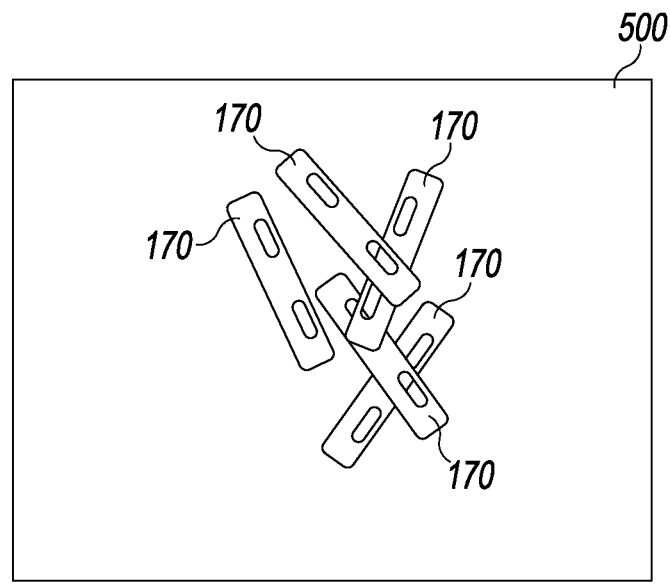
Figure 25:
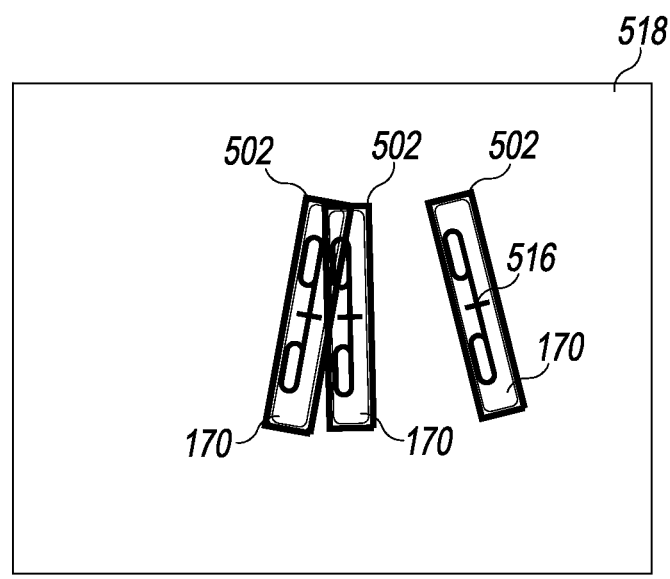

Returning to FIG. 15, the procedure 1000 may then advance to block 1004. In block 1004, a cutting blade 170 is selected and retrieved from the tray 34. To do so, the controller 400 operates the camera 312 to capture images of the blades 170 in the tray 34. One such image 500 is shown in FIG. 24. As shown in FIGS. 24-25, the blades 170 may be positioned in arbitrary locations and orientations relative to one another within the tray 34. The controller 400 may process the captured image 500 to identify the location 516 of one of the blades 170 in the tray 34, which may be reflected by an analyzed image 518 as shown in FIG. 25.

For example, in the illustrative embodiment, the controller 400 utilizes a geometric object-identifying function of the software package included with the Epson model C3 six-axis articulated arms. In particular, a blade reference image (not shown) loaded by the user and stored in the memory device 404 of the controller 400 is compared to the captured image 500 of the blades 170 to identify a match 502. The geometric object-identifying function employs an algorithmic approach that identifies matches to a reference image (i.e., an object model) by using edge-based geometric features. Further, the geometric object-identifying function includes various parameters such as a reference image to be used for comparison to another image and an acceptance or tolerance level required for the match 502. The acceptance level corresponds with a likelihood of a match 502 and may, without loss of generality, be considered herein as a normalized value between 0 and 1. Accordingly, if the acceptance level is set to 0.5, only those objects in the analyzed image having at least a fifty percent likelihood of a match 502 with the reference image based on a suitable imaging algorithm will be identified by the controller 400. In a specific embodiment, the acceptance level may correspond with a percentage of a reference image that must be identified in a continuous region of an analyzed image to constitute a match 502.

In the illustrative embodiment, the controller 400 analyzes the captured image 500 using the matching algorithm, the blade reference image, and a normalized acceptance level of 0.4 (i.e., 400 out of 1000) to determine whether there are any blades 170 on the tray 34. An assumption is made that if any blades 170 are on the tray 34, even if the blades 170 are overlapping, such an acceptance level should return the identified locations of those blades 170 on the tray 34. As such, in another embodiment, a different acceptance level may be used. If no blades 170 are identified, the controller 400 determines that no blades 170 are located on the tray 34 and processes the error. For example, the controller 400 may instruct the user of the system 10 via a display 460 to place additional blades 170 on the tray 34 or otherwise remedy the error.

If the controller 400 determines that at least one blade 170 is located on the tray 34, the controller 400 analyzes the captured image 500 again with the acceptance level set to a higher threshold value such as 0.95 (i.e., 950 out of 1000) to identify a blade 170 that does not overlap with another blade 170 on the tray 34. If at least one non-overlapping blade 170 is identified, the controller 400 selects that blade 170 for use. However, if non-overlapping blades 170 are identified, the controller 400 executes a protocol to separate the overlapping blades 170.

In doing so, the controller 400 identifies the location of a blade 170 that overlaps with another blade 170 on the tray 34. For example, the controller 400 may use the image locations identified with the normalized acceptance level set at 0.4, if saved, or similarly analyze the image 500. When the group of blades 170 has been identified, the controller 400 determines the geometric center of the group using a suitable imaging algorithm (e.g., by detecting a center of mass of the group) and instructs the corresponding robotic arm 16 to move the grip assembly 320 into position for grasping the group of blades 170 at the identified center of mass.

To grasp an object from the tray 34 or plate 36, the grip assembly 320 is positioned above a grip location or point 504 of the object such that the hollow passageway 352 of the grip assembly is approximately collinear with the point 504. The grip assembly 320 is then advanced downward toward the object until the grip 18 is in full contact with the outer surface of the object. As described above, the suspension mechanism 326 operates to prevent the object from being crushed while ensuring that the grip 18 is in full contact with the object's surface to provide limited loss of suction. The negative pressure source 356 may then be activated to secure the object to the grip 18.

Similarly, if there are no non-overlapping blades, the grip assembly 320 may grasp a group of blades 170 at the identified center of mass. The controller 400 may then operate the arm 16 to move the grip assembly 320 vertically a short distance (e.g., one inch) above the surface of the tray 34 and horizontally a short distance but still within a perimeter of the tray 34. The controller 400 may then deactivate the negative pressure source 356 to drop the group of blades 170 back onto the tray 34. It will be appreciated that one or more of the blades 170 within the group may fall during transport. The controller 400 operates the camera 312 to capture another image of the blades 170 in the tray 34 and analyzes the new image similarly to that described above to identify a non-overlapping blade 170. If no non-overlapping blade 170 is identified, the controller 400 may again instruct the grip assembly 320 to grasp a group of blades 170 and drop the blades 170 on another location within the tray 34. The controller 400 may continue to repeat the routine until a non-overlapping blade 170 is identified selected for use.

In another embodiment, the controller 400 may implement other procedures for separating overlapping blades 170 and identifying a particular blade 170 for selection. Further, the controller 400 may utilize any suitable image processing algorithms and techniques to identify the locations of the blades 170 in the tray 34. For example, the controller 400 may utilize feature detection algorithms, techniques, and filters such as Speeded Up Robust Features (SURF), Scale-Invariant Feature Transform (SIFT), Multi-Scale Oriented Patches (MOPS), Canny, image gradient operators, and Sobel filters to identify features (e.g., interest points such as corners, edges, blobs, etc.) of the image 500 and the blade reference image. In some embodiments, the controller 400 may utilize feature matching algorithms such as the Random Sample Consensus (RANSAC) algorithm to determine whether any features identified in the image 500 and the blade reference image correspond with one another and, if so, the corresponding locations of those features. Additionally or alternatively, the controller 400 may utilize image segmentation algorithms (e.g., pyramid segmentation, watershed algorithms, etc.) for identifying objects in an image. It will be appreciated that, depending on the particular embodiment, the controller 400 may utilize any one or more of the algorithms described above during the analyses of captured images.

After the controller 400 has identified a blade 170, the controller 400 uses blade features such as, for example, the mounting holes 264 of the blade 170 to locate the cutting edge 262 of the blade. The controller 400 may then calculate the rotation angle of the blade 170 with respect to the grip assembly 320 and calculate the correct position point 504 on the blade for attachment of the grip 18. The grip assembly 320 grasps the blade at the point 504 in a similar manner to that described above.

Figure 26:
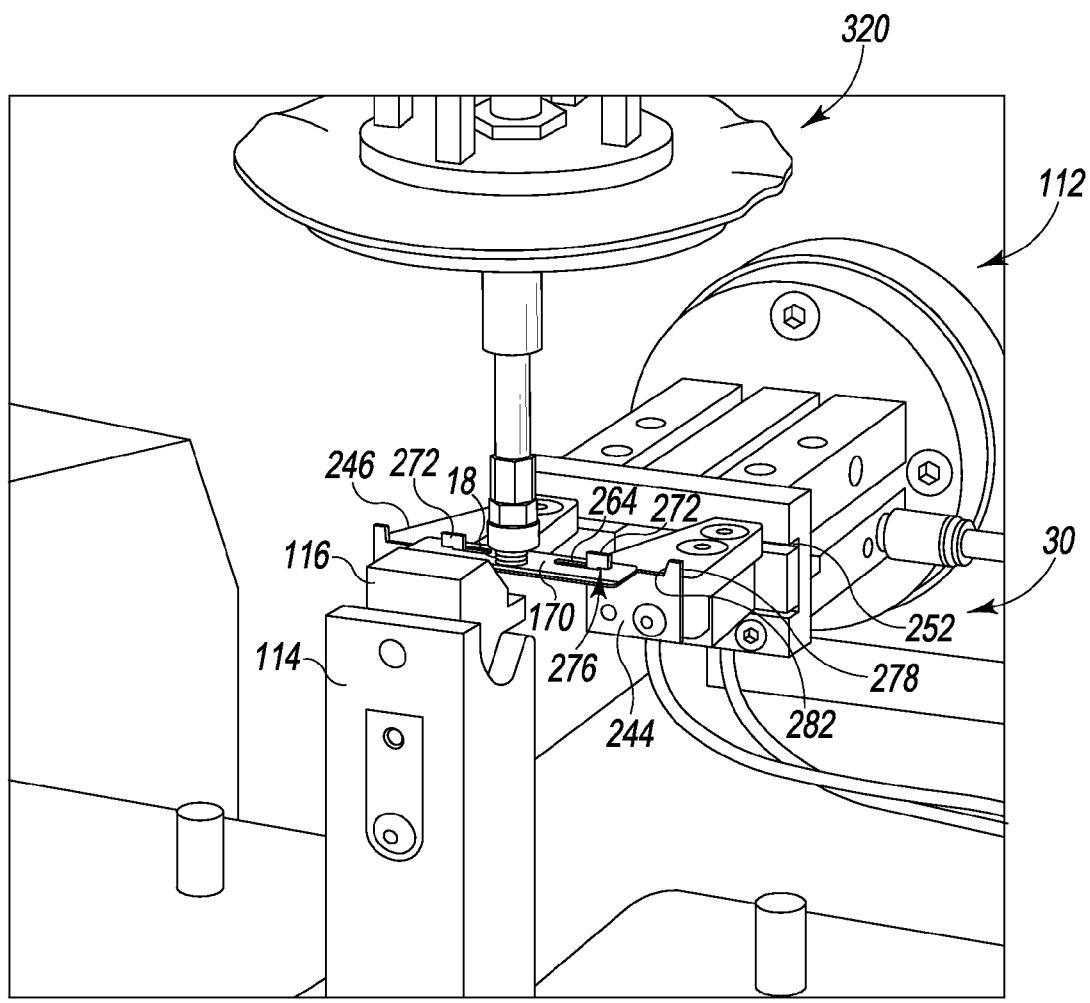

Returning to FIG. 15, the procedure 1000 advances to block 1006 once the grip 18 has picked up a blade 170. In block 1006, the controller 400 operates the robotic arm 16 and the cutting device 112 to secure the cutting blade 170 to the cutting device 112. To do so, the controller 400 activates the robotic arm 16 to move the cutting blade 170 to the cutting station 30 and position the cutting blade 170 above the jaws 244, 246 of the cutting device 112. To position the cutting blade 170 on the jaws 244, 246, the robotic arm 16 may be moved in a circular motion to align the oblong mounting holes 264 of the blade 170 with the tabs 272 of the jaws 244, 246. The beveled edges 282 of the outer tabs 278 assist in guiding the blade 170 onto the tabs 272. When the blade 170 is positioned on the tabs 272, the grip 18 is moved downward, causing the blade 170 to deflect slightly. As shown in FIG. 26, the controller 400 may then operate the jaws 244, 246 to secure the blade 170 to the cutting device 112. A camera (not shown) may be used to capture images of the blade 170 positioned on the cutting device 112, and the controller 400 may use image processing techniques similar to those described above confirm the blade 170 is properly positioned on the jaws 244, 246.

With the blade 170 positioned on the jaws 244, 246, the controller 400 may operate the compressed air source 256 to move the jaws 244, 246 outward along the channel 252 of the elongated body 240. As the jaws 244, 246 are advanced outwardly, portions of the cutting blade 170 are advanced into the slots 276 formed at the base of the tabs 272, thereby securing the cutting blade 170 to the jaws 244, 246. The controller 400 may deactivate the vacuum source 356 to release the cutting blade 170 from the grip 18 and operate the robotic arm 16 to move the grip 18 out of the cutting station 30.

Figure 27:
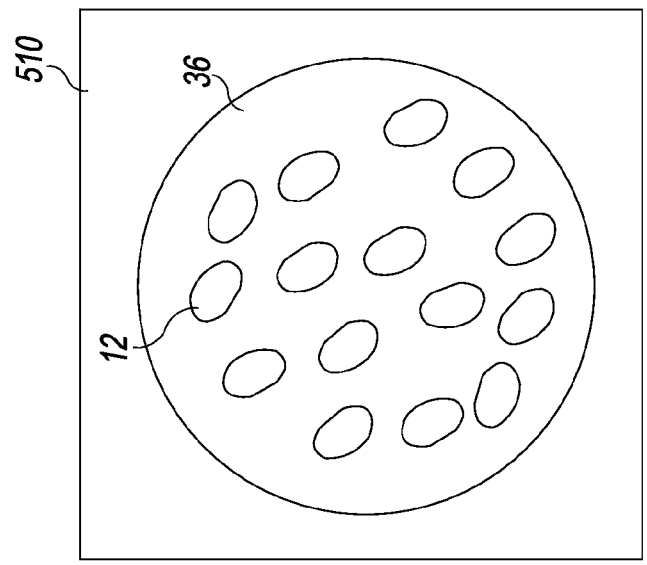

Returning to FIG. 15, the procedure 1000 advances to block 1008 in which the controller 400 operates the camera 52 to capture images of the seeds 12 on a plate 36 positioned in the corresponding delivery area 24. One such image 510 is shown in FIG. 27. As shown in FIG. 27 and similar to that described above with regard to the blades 170 in the tray 34, the seeds 12 may be arbitrarily positioned relative to one another within the plate 36.

Figure 28:
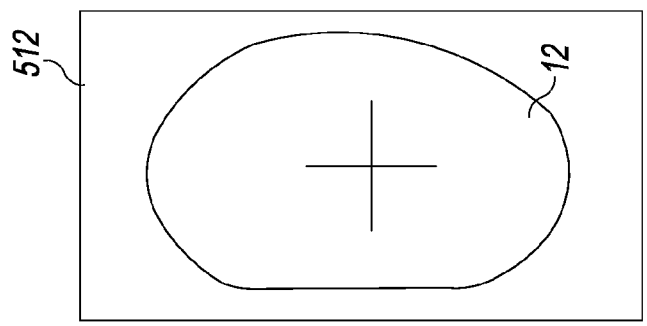

In block 1010, the controller 400 may process the captured image 510 to determine the location of one of the seeds 12 on the plate 36 for selection. To do so, the controller 400 may analyze the captured image 510 using a matching algorithm (e.g., the geometric object-identifying function described above) to compare a reference image 512 of a seed 12 lying on its side, as shown in FIG. 28, to the captured image 510. In the illustrative embodiment, the controller 400 assumes that the user of the system 10 has placed each of the seeds 12 on its side within the plate 36 in a single layer. Accordingly, there is a high likelihood of detecting a match 522. However, in other embodiments, the controller 400 may not make such an assumption; rather, the controller 400 may, for example, determine which seeds 12, if any, are not appropriately oriented and ignore those seeds 12. The system 10 may generate a warning or instruct the user to remedy the situation (e.g., via the display 460), or otherwise handle the error. In other embodiments, the controller 400 may use blob detection or other image analysis algorithms to determine the location of the seeds 12 on the plate 36.

Figure 29:
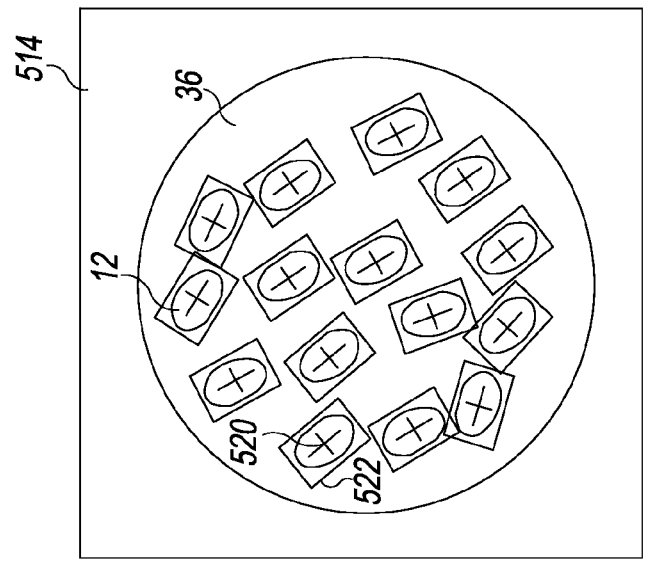
FIGS. 27-29 are illustrations of an image capture process of the operating procedure of FIGS. 15-16 to identify a seed to be picked up by the system of FIG. 1.

In any case, the controller 400 determines the locations 520 of one or more seeds 12 on the plate 36, which may be reflected by an analyzed image 514 as shown in FIG. 29. Further, in some embodiments, the controller 400 determines an angle of rotation of the identified seed(s) 12 on the plate 36 relative to the seed 12 depicted in the reference image 512. Based on that information, the controller 400 may determine an amount by which to rotate the grip 18 to place the secured seed 12 in a predefined orientation (e.g., zero degree angle relative to the coordinate system of the robotic arm 16) on the grip 18. By doing so, the controller 400 may be able to identify the hilum and embryo axis (i.e., the embryonic axis) of the seed 12 as described below and save processing time.

Figure 31:
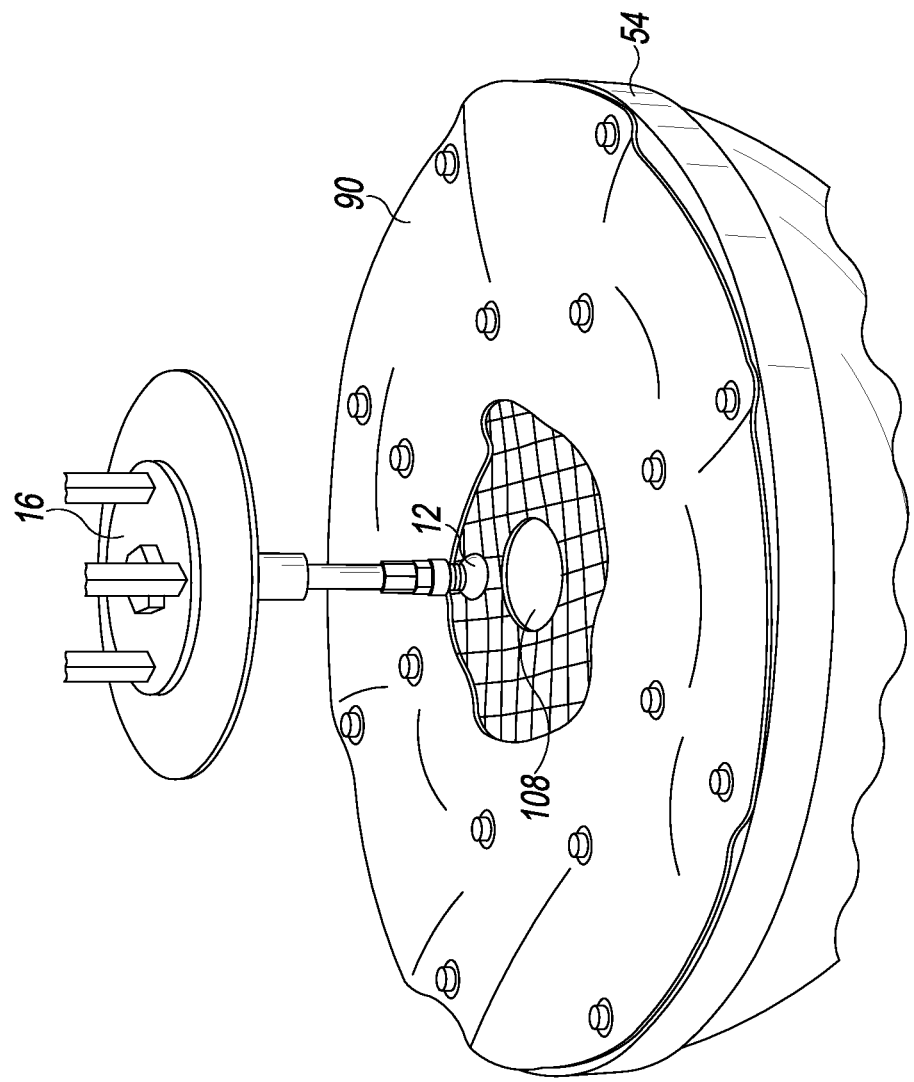

Returning to FIG. 15, the procedure 1000 advances to block 1012. In block 1012, the controller 400 identifies and selects (e.g., arbitrary or algorithmically) one of the seeds for trimming and bisection by the system 10. In the illustrative embodiment, the controller 400 identifies the center of mass of the selected seed 12 and uses that as the point 504 to attach the grip 18 as shown in FIG. 30. In block 1014, the grip assembly 320 grasps the selected seed 12 at its center of mass. To do so, the grip assembly 320 is positioned above the center of mass (i.e., the point 504) such that the hollow passageway 352 of the grip assembly is approximately collinear with the point 504. The grip assembly 320 is then advanced downward toward the selected seed until the grip 18 is in full contact with the outer surface of the seed. As described above, the suspension mechanism 326 operates to prevent the seed from being crushed while ensuring that the grip 18 is in full contact with the seed's surface to provide limited loss of suction. The negative pressure source 356 may then be activated to secure the seed to the grip 18. The procedure 1000 may then advance to block 1016 in which the robotic arm 16 moves the gripped seed 12 through the central opening 108 in the cover 90 and into the chamber 62 of the lighted dome 54, as shown in FIG. 31. In the illustrative embodiment, the gripped seed 12 is positioned within the chamber 62 at a location that is within the fields of view of each of the cameras 56, 58 (e.g., an intersection point of the optical axes 80, 82). For example, in some embodiments, the gripped seed 12 is positioned, at least in part, within the focal plane of each of the cameras 56, 58.

Figure 17:
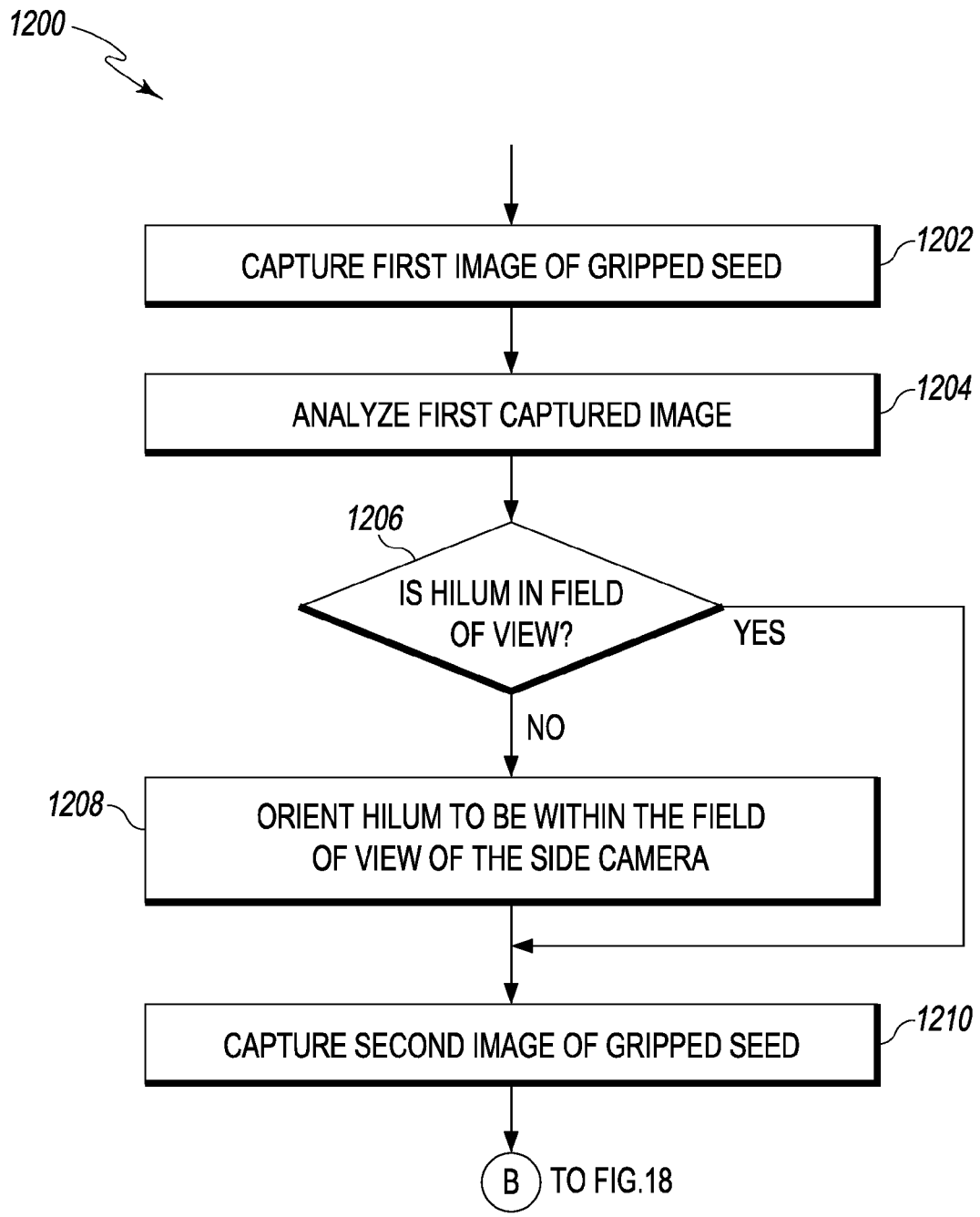
FIGS. 17-19 are block diagrams showing an illustrative procedure for determining a desired cutting position and cutting depth for a soybean seed.
Figure 18:
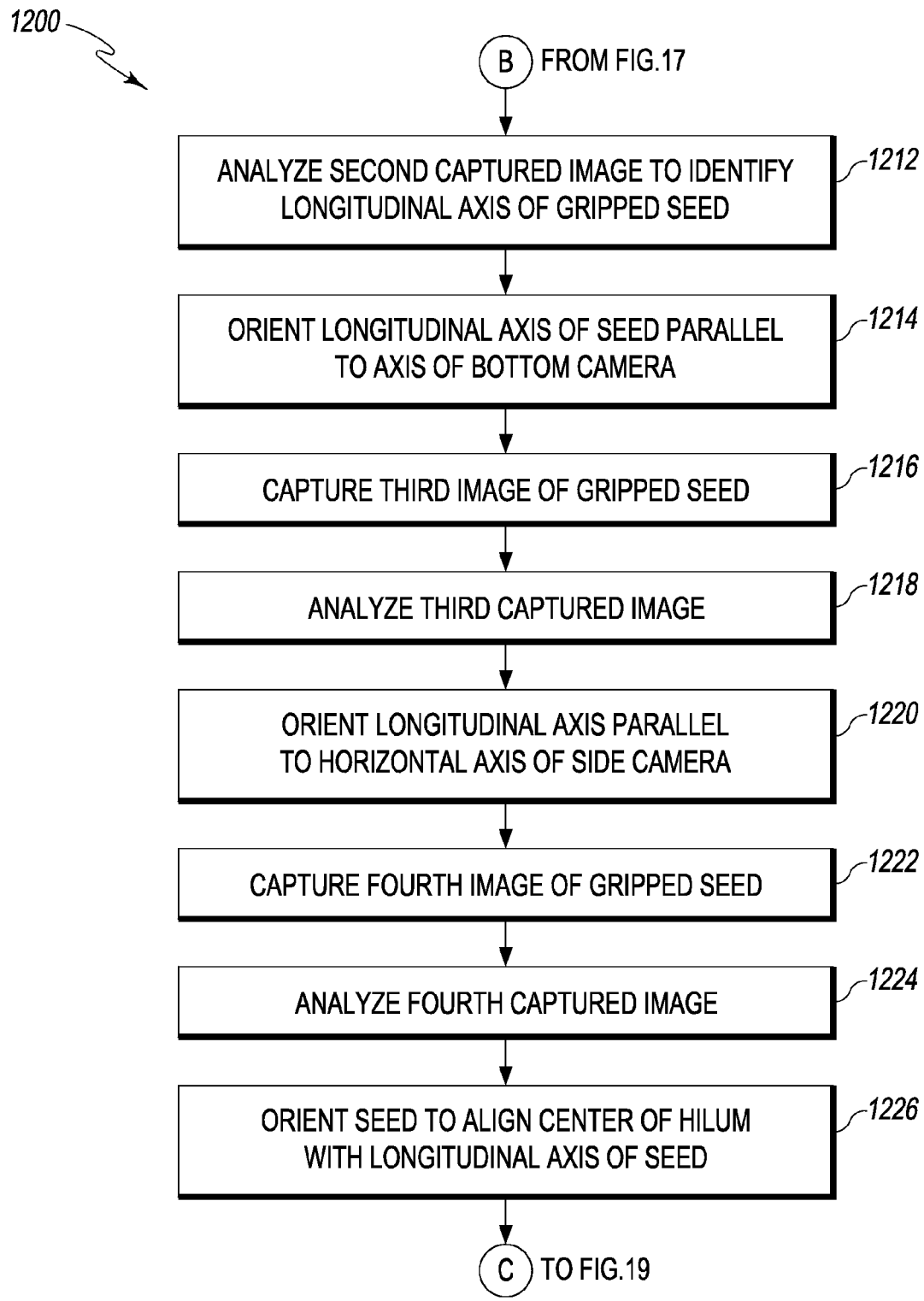

When the seed 12 is positioned in the chamber 62 of the lighted dome 54, the procedure advances to block 1018, as shown in FIG. 15. In block 1018, the controller 400 determines the proper orientations of the gripped seed 12 for trimming and bisecting the seed 12 with the cutting device 112. That is, the controller 400 determines how the seed 12 is positioned relative to the grip 18 so that the robotic arm 16 can properly position the seed 12 on the cutting block 116 for trimming and bisecting the embryo of the seed 12. To do so, an illustrative operating procedure 1200, as shown in FIG. 17, may be used. Although the procedure 1200 is described herein with regard to analyzing several still images in a linear manner, it will be appreciated that, in some embodiments, the controller 400 may perform multiple image analyses in parallel or continuously analyze video, for example.

The procedure 1200 may begin with block 1202 in which the controller 400 operates the camera 58 to capture an image 530 of the gripped seed 12 from a side perspective. In block 1204, the controller 400 analyzes the image 530 to determine whether a hilum 424 of the seed 12 is visible on the seed 12. That is, the controller 400 determines whether the hilum 424 (see FIG. 32) is within a field of view of the camera 58. To do so, the controller 400 may utilize any suitable image processing algorithms such as those described herein. For example, in the illustrative embodiment, the controller 400 utilizes a correlation model that uses shadows (e.g., grayscale pixel intensity) to model the seed 12 and identify a match 534, if any, between the seed 12 and a reference image 536 of a seed hilum as shown in FIG. 32. In particular, the correlation model performs a pixel-to-pixel match of the reference image 536 to the captured image 530.

In block 1206, the controller 400 determines whether the hilum 424 of the seed 12 is within the field of view of the camera 58. If so, the procedure 1200 advances to block 1210. However, if the controller 400 determines that the hilum 424 is not within the field of view of the camera 58, the procedure advances to block 1208.

In block 1208, the controller 400 may reorient the seed 12 such that the hilum is within the field of view of the camera 58. In particular, the controller 400 operates the robotic arm 16 to rotate the seed 12 about the axis 358 of the grip 18 until the hilum 424 is within the field of view of the camera 58. In some embodiments, the robotic arm 16 rotates the seed 12 by an incremental angle, the camera 58 captures a new image of the gripped seed 12, and the controller 400 analyzes the new image to determine whether the hilum 424 is now within the field of view of the camera 58. If not, the routine may be repeated until the hilum 424 is within the field of view of the camera 58. In an embodiment, the robotic arm 16 may first rotate the seed 12 by an angle of 180 degrees to expedite the process of locating the hilum 424.

Once the hilum 424 is determined to be within the field of view of the camera 58, the procedure 1200 may advance to block 1210.

Figure 33:
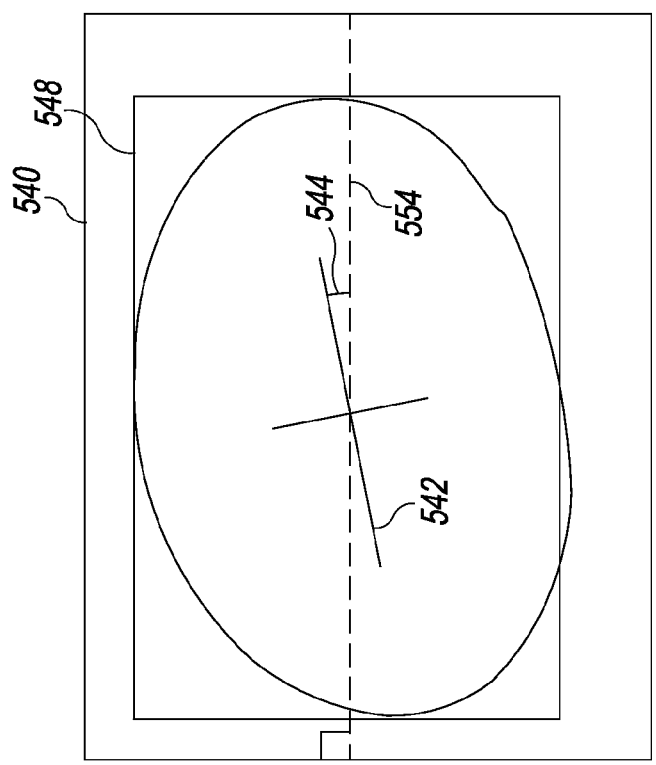

In block 1210, the controller 400 operates the camera 56 to capture an image 540 of the gripped seed 12 from a bottom perspective as shown in FIG. 33. The procedure 1200 then advances to block 1212 of FIG. 18. In block 1212, the controller 400 analyzes the captured image 540 to identify a longitudinal axis 542 (i.e., a major axis) of the seed 12 in the image 540. In the illustrative embodiment, the controller 400 utilizes a blob detection algorithm to locate the seed 12 in the captured image 540 and determine the principal axes (i.e., the major axis and the minor axes) of the seed 12. For example, the blob detection algorithm may identify the seed 12 in the captured image 540 as a blob, determine the center of mass and edges of that blob, and approximate the major and minor axes based on that information.

It will be appreciated that the particular blob detection algorithm utilized may vary depending on the particular embodiment. For example, in the illustrative embodiment, the controller 400 uses blob detection algorithms of the software package included with the Epson model C3 six-axis articulated arms. In some embodiments, the blob detection algorithms may be based on Difference of Gaussian (DoG), Laplacian of Gaussian (LoG), Hessian determinants, and/or other operators. In an embodiment, the controller 400 may utilize one or more of the blob detection algorithms described in, for example, Lindeberg, *Detecting Salient Blob-Like Image Structures and Their Scales with a Scale-Space Primal Sketch: A Method for Focus-of-Attention,* 11(3) International Journal of Computer Vision, 283-318 (1993). Further, in some embodiments, the controller 400 may draw a rectangular border 548 around the seed 12 (or other objects) in a processed version of the captured image 540 to indicate the location of the identified seed 12 (or other objects). In other embodiments, the controller 400 may utilize other image analysis algorithms (e.g., image segmentation) to identify the seed 12 and/or the longitudinal axis 542.

The controller 400 further determines an angle 544 of rotation of the major or longitudinal axis 542 of the seed 12 relative to a horizontal axis 546 or other horizontal line 554 of the captured image 540. In other words, the angle 544 defined between the longitudinal axis 542 and the horizontal axis 546 or other horizontal line 554 is determined. In the illustrative embodiment, the camera 56 is configured to capture rectilinear images; as such, the horizontal axis 546 of the captured image 540 may be considered parallel to an edge of the camera 56.

Figure 35:
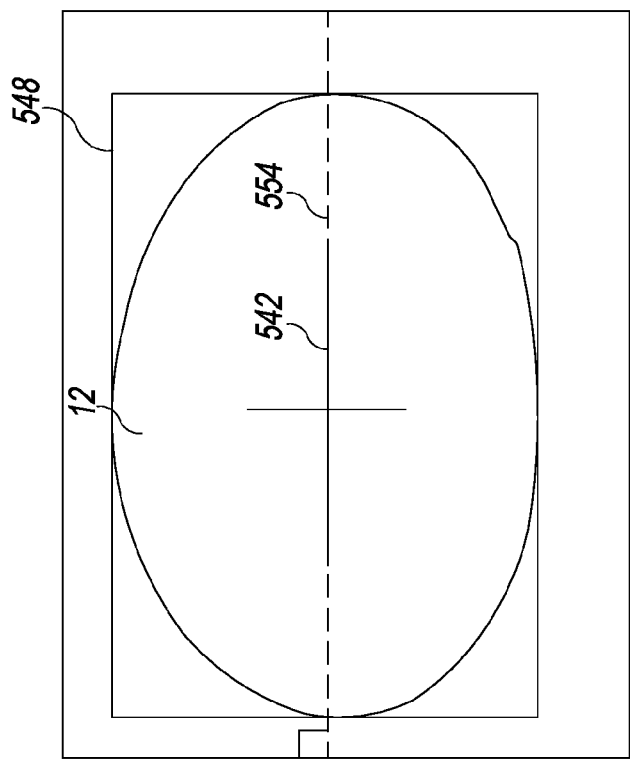
Figure 34:
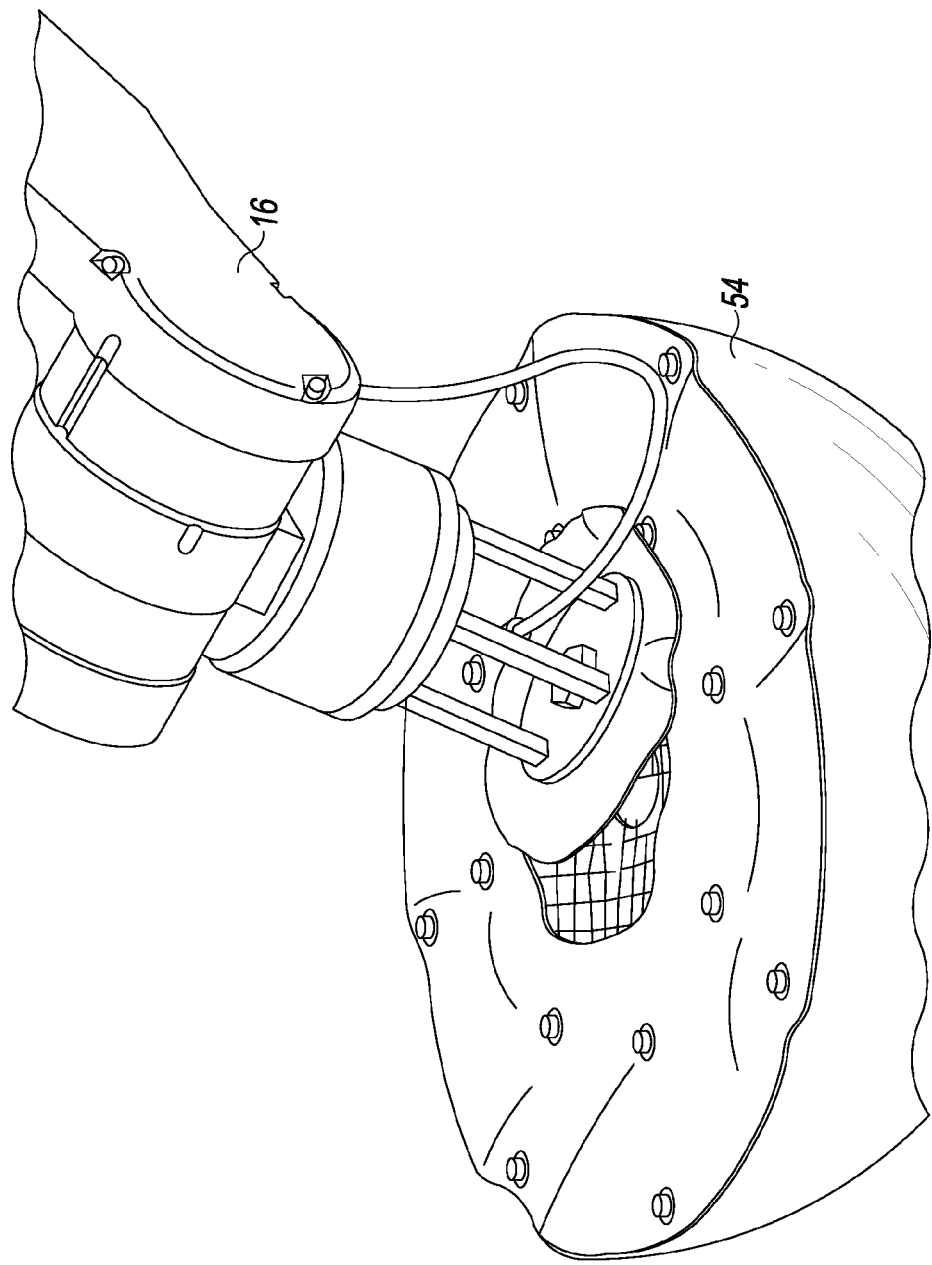

As shown in FIG. 34, the robotic arm 16 is capable of reorienting the gripped seed 12 within the lighted dome 54. For example, depending on the reorientation necessary, the robotic arm 16 may change the orientation of the seed 12 by rotating and/or translating the seed 12. Accordingly, in block 1214 of FIG. 18, the controller 400 operates the robotic arm 16 to orient the seed 12 such that the longitudinal axis 542 is parallel to the horizontal axis 546 as shown in FIG. 35. In particular, the robotic arm 16 rotates the seed 12 about the axis 358. In some embodiments, the controller 400 may not require precise parallelism but may establish a tolerance for the angle 544. In some embodiments, the tolerance may be less than or equal to 1.0 degree. In other embodiments, the tolerance may be less than or equal to 0.5 degrees. In still other embodiments, the tolerance may be less than or equal to 0.3 degrees for the angle 544. It should be appreciated that similar tolerances may be established for any of the measurements described herein. As indicated above, the camera 56 and the robotic arm 16 are calibrated such that their coordinate systems are mapped to one another, so orienting the seed 12 in such a way effectively aligns the longitudinal axis 542 of the seed 12 with an axis of the robotic arm's coordinate system.

Figure 36:
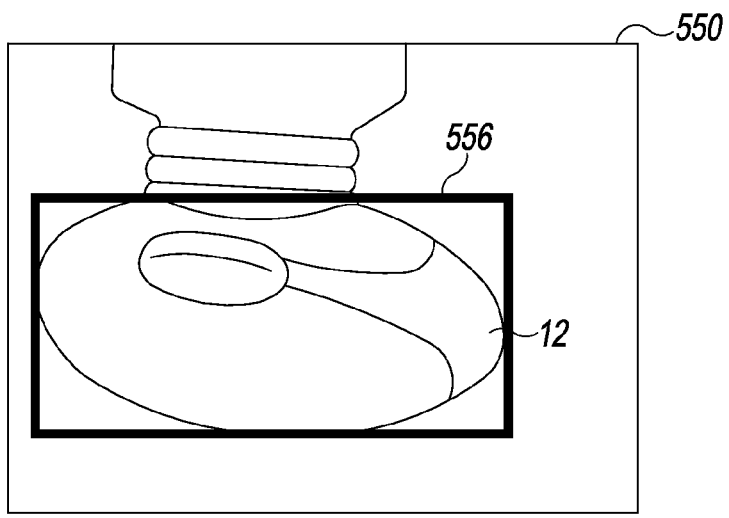

Returning to FIG. 18, the procedure 1200 may advance to block 1216 in which the controller 400 operates the camera 58 to capture an image 550 of the gripped seed 12. As shown in FIG. 36, the image 550 is a side elevation view of the seed from the perspective of the camera 58. The image 550 may be analyzed in block 1218 to identify the gripped seed 12 and a longitudinal axis 552 of the seed 12. It will be appreciated that the longitudinal axes 552, 578 may or may not be coincident with one another due to the irregular shape of the seed 12. The controller 400 may utilize a blob detection algorithm to identify a location 556 of the seed 12 and/or locate the longitudinal axis 552 in the captured image 550 in a similar manner to that described above with regard to the analysis of the captured image 540.

Figure 37:
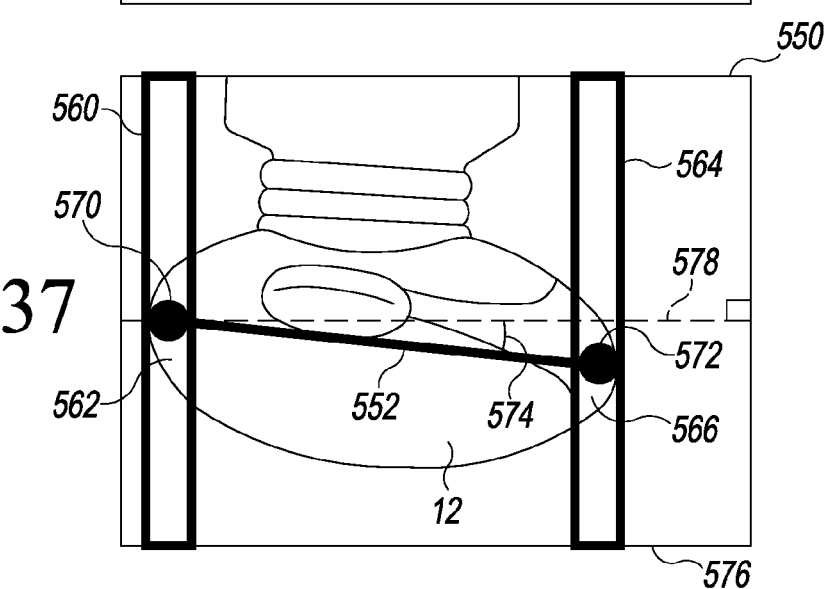

In the illustrative embodiment, the controller 400 identifies a left vertical slice 560 or cross section of the seed 12 at a left longitudinal end 562 of the seed 12 and a right vertical slice 564 or cross section of the seed 12 at a right longitudinal end 566 of the seed 12 in the captured image 550. As shown in FIG. 37, each of the vertical slices 560, 564 is at least one pixel in width. In the illustrative embodiment, the width of the slices is 25 pixels, but the width may vary in other embodiments. The controller 400 determines a center of mass 570 of the left vertical slice 560 of the seed 12 and a center of mass 572 of the right vertical slice 564 of the seed 12. The longitudinal axis 552 of the seed 12 in the captured image 550 is defined as the line intersecting both centers of mass 570, 572. In other words, the longitudinal axis 552 runs through the centers of mass of the longitudinal ends 562, 566 of the seed 12. The controller 400 further determines an angle 574 of the longitudinal axis 552 relative to a horizontal axis 576 or other horizontal line 578 of the captured image 550.

Figure 38:
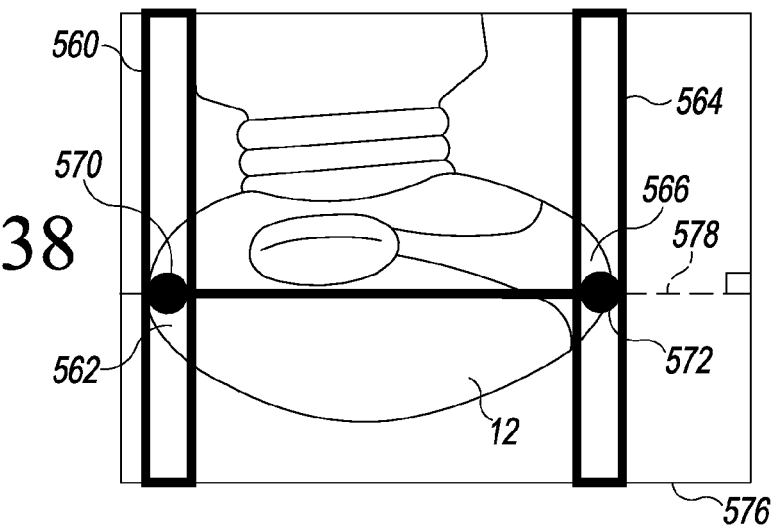

The procedure 1200 may advance to block 1220 in which the seed 12 is reoriented. In particular, the controller 400 operates the robotic arm 16 to orient the seed 12 such that the longitudinal axis 552 is parallel to the horizontal axis 576 as shown in FIG. 38. Specifically, the robotic arm 16 rotates the seed 12 with respect to the captured image 550 until the longitudinal axis 552 is parallel to the horizontal axis 576 (e.g., subject to a tolerance level such as within one degree of parallelism). When the seed 12 is properly oriented, the procedure 1200 continues to block 1222.

Figure 39:
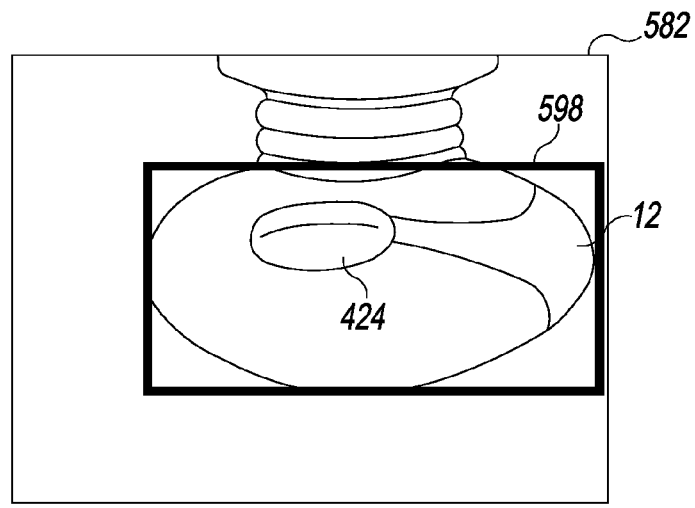
Figure 40:
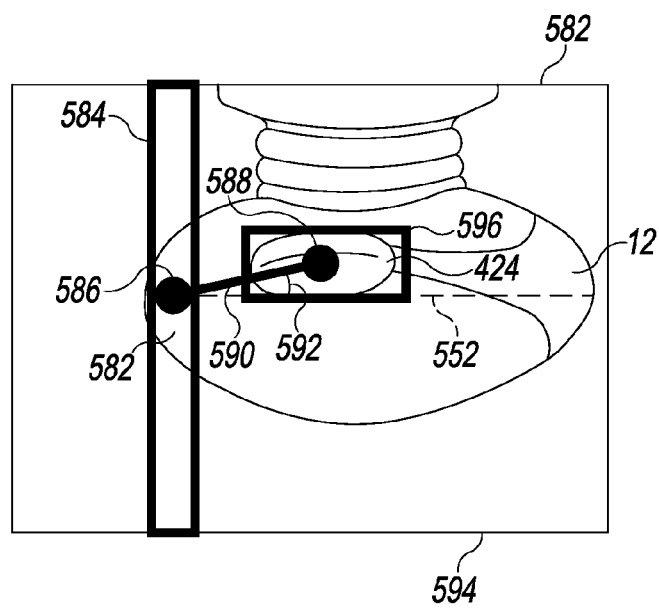

In block 1222, the controller 400 operates the camera 58 to capture another image 580 of the gripped seed 12 from a side elevation (i.e., the field of view of the camera 58), as shown in FIG. 39. The image 580 is analyzed in block 1224 to identify the gripped seed 12 and a location 596 of the hilum 424 of the seed 12 relative to a center of mass or longitudinal axis of the seed 12. In the illustrative embodiment, the controller 400 utilizes blob detection to determine the location 598 of the seed 12 in the captured image 580. Additionally, the controller 400 utilizes a suitable algorithm to determine the location of the hilum 424 on the seed 12 in the capture image 580. For example, the controller 400 may determine the location 596 of the hilum 424 using the reference image 536 of a hilum (see FIG. 32) and/or image feature matching algorithms as described above. The controller 400 identifies a longitudinal end 582 (e.g., either the left or right end) of the seed 12 and a vertical slice 584 of the longitudinal end 582 of the seed 12 in a manner similar to that described above. As shown in FIG. 40, the controller 400 identifies a center of mass 586 of the vertical slice 584 of the seed 12 and a center of mass 588 of the hilum 424 and draws a virtual line 590 between the centers of mass 586, 588. The controller 400 further determines an angle 592 of the line 590 relative to a horizontal axis 594 of the captured image 580 or the longitudinal axis 552 of the seed 12.

Figure 41:
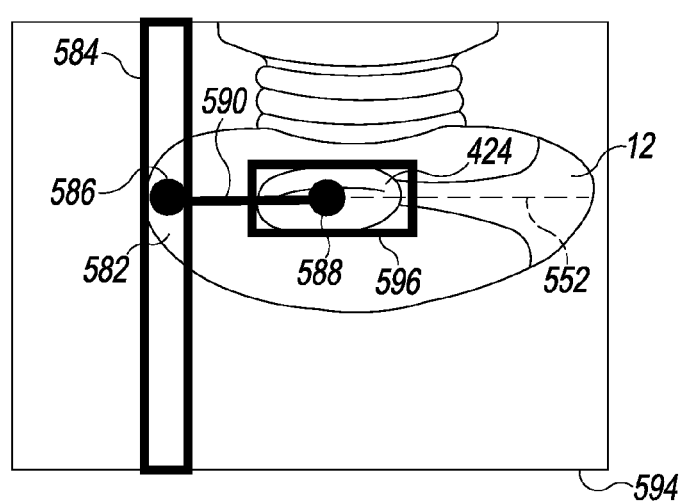
Figure 49:
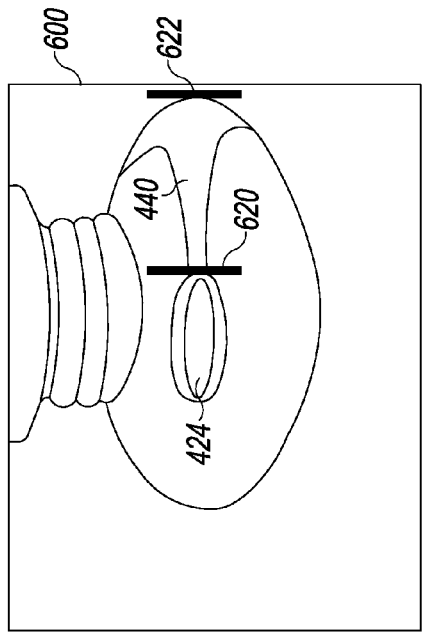
Figure 50:
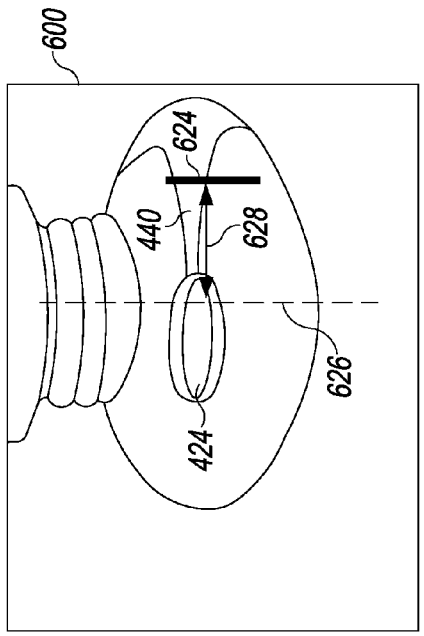

Returning to FIG. 18, the procedure 1200 advances to block 1226 in which the controller 400 operates the robotic arm 16 to orient the seed 12 to align the center of mass 588 of the hilum 424 with the longitudinal axis 552 of the seed 12 as shown in FIG. 41. In particular, the robotic arm 16 rotates the seed 12 toward or away from the camera 58 until the line 590 between the centers of mass 586, 588 is parallel to the horizontal axis 594 of the captured image 580. At that point, the line 590 corresponds to the longitudinal axis 436 of the hilum 424 such that the seed plane 438 defined by the longitudinal axis 436 of the hilum 424 and the longitudinal axis 436 of the seed 12 is aligned with a defined plane of the coordinate system of the robotic arm 16.

Figure 19:
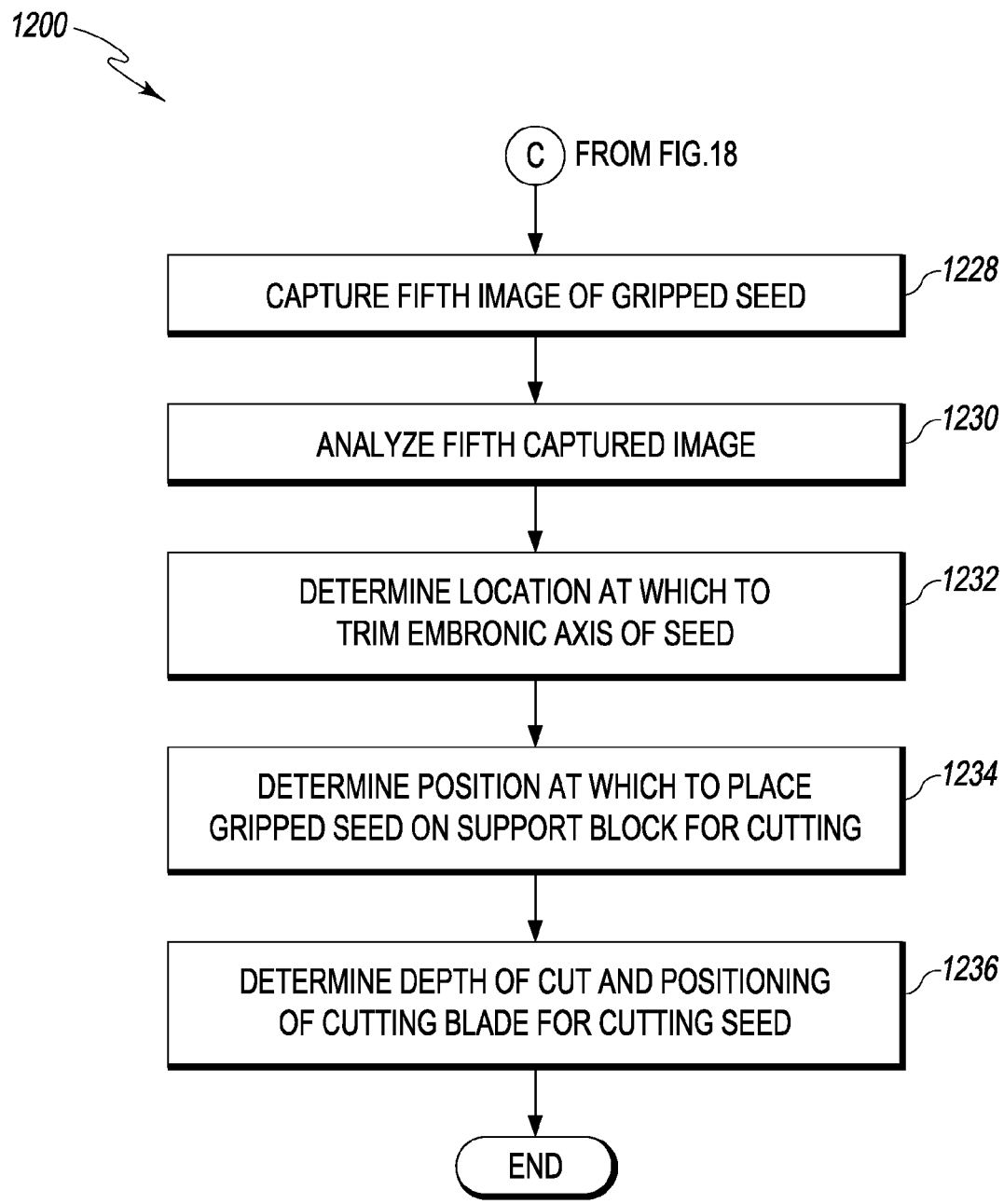

The procedure 1200 may then advance to block 1228 of FIG. 19. In block 1228, the controller 400 operates the camera 58 to capture images of the gripped seed 12 from a side elevation. Such images 600 are shown in FIGS. 43-48. Returning to FIG. 19, in block 1230, the controller 400 analyzes the captured image 600 to determine the location of the embryonic axis 440 of the seed 12. The controller 400 may use any suitable algorithm for doing so.

For example, in the illustrative embodiment, the controller 400 may utilize a reference image 612 of an embryonic axis, as shown in FIG. 42, in conjunction with the geometric object-identifying function and/or correlation model described above to identify the embryonic axis 440. It will be appreciated that the controller 400 has identified a match 602 for the embryonic axis 440 in each of FIGS. 46-48 as shown. However, the controller 400 has failed to identify the embryonic axis 440 in each of FIGS. 43-45, because a significant portion of the embryonic axis 440 is not within the field of view of the camera 58. In those circumstances, the controller 400 operates the robotic arm 16 to rotate the seed 12 until the embryonic axis 440 is within the field of view of the camera 58 and detected by the controller 400.

Figure 51:
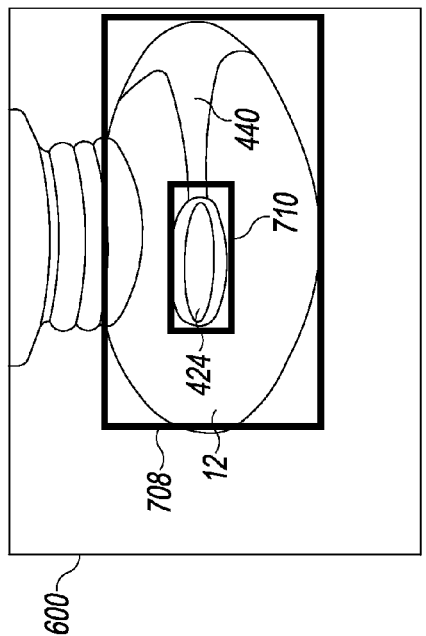

Returning to FIG. 19, the procedure 1200 advances to block 1232 in which the controller 400 determines a location at which to trim the embryonic axis 440 of the seed 12. To do so, the controller 400 determines the location 708 of the seed 12, the location 602 of the embryonic axis 440, and the location 710 of the hilum 424 of the seed 12 in the captured image 600 or a new image captured by the camera 58 as shown in FIGS. 49-52. In particular, the controller 400 identifies an edge 620 of the hilum 424 nearest the embryonic axis 440 and an edge 622 of the seed 12 on the same side as the embryonic axis 440 as shown in FIG. 51. Further, in the illustrative embodiment, the controller 400 determines a vertical cross section 624 halfway between the edges 620, 622. The vertical cross section 624 corresponds with the location at which the system 10 is to trim the embryonic axis 440 of the seed 12. In other embodiments, the controller 400 may identify a point other than the midpoint between the edges 620, 622 (e.g., based on user input).

Figure 52:
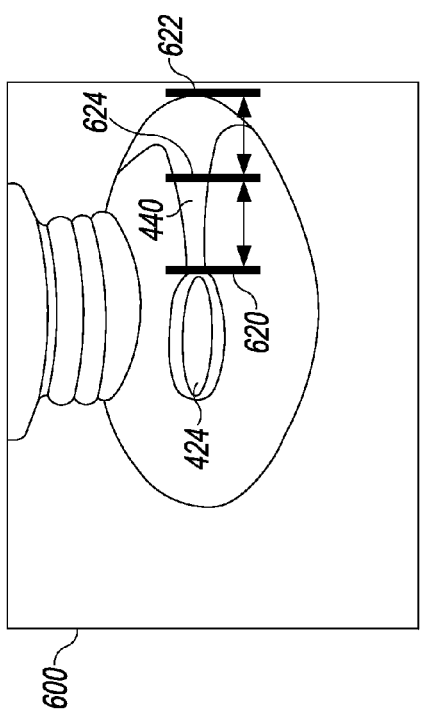

As indicated above, the controller 400 has calibrated the system 10 such that the coordinate system for the robotic arm 16 and the coordinate system of the camera 58 are mapped to one another. Because the coordinate system of the robotic arm 16 is known, the controller 400 knows the location of a center 626 of the grip 18 with respect to the captured image 600. The controller 400 also knows the correspondence between physical distance in the coordinate system of the robotic arm 16 (e.g., in millimeters) and distance in the coordinate system of the camera 58 (e.g., in pixels). That information is used to determine a horizontal distance 628 between the center 626 and the vertical cross section 624 in the captured image 600 as shown in FIG. 52. The controller 400 further calculates a distance of the embryonic trimming cut relative to the center 626 of the grip 18.

Figure 53:
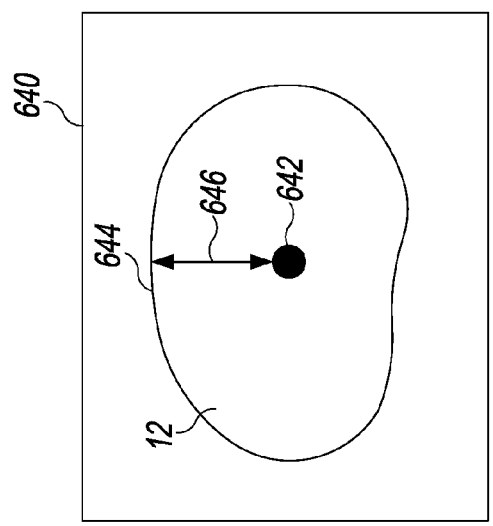

Returning to FIG. 19, in block 1234, the controller 400 determines the position at which to place the gripped seed 12 on the cutting block 116 of the cutting station 30 to be trimmed and bisected by the cutting blade 170. To do so, the controller 400 operates the camera 56 to capture an image 640 of the seed 12 from a bottom perspective. As indicated above, the mapping between the coordinate systems of the robotic arm 16 and the camera 56 is known, so a point 642 projected along the grip axis 358 to the captured image 640 may be determined. The controller 400 further analyzes the captured image 640 to identify a back edge 644 of the seed 12 (i.e., opposite the hilum 424 and the embryonic axis 440) and a distance 646 between the point 642 and the back edge 644 as shown in FIG. 53. Because the controller 400 has the location of the front wall 154 of the cutting block 116 stored in memory, the controller 400 is able to properly position the seed 12 on the cutting block 116. In particular, the controller 400 operates the robotic arm 16 to position the seed 12 on the flange 124 and with the center of the grip 18 defined by the grip axis 358 positioned the determined distance 646 away from the front wall 154.

Figure 54:
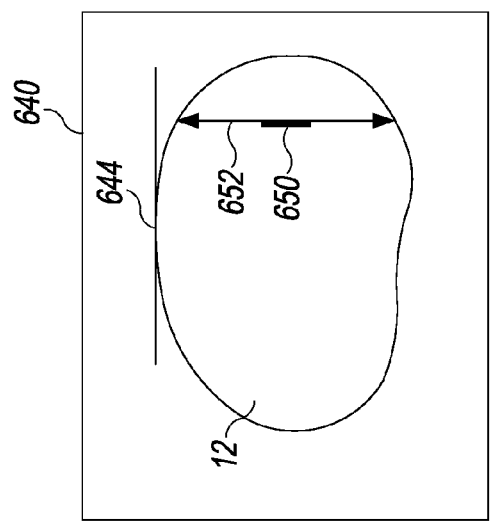

Returning to FIG. 19, in block 1236, the controller 400 determines the depth of the trimming and/or bisection cut and the positioning of the blade 170 for cutting the seed 12. As indicated above, the controller 400 previously determined a point at which to trim the embryonic axis (i.e., the vertical cross section 624 as shown in FIG. 52). In the illustrative embodiment, the controller 400 maps the vertical cross section 624 to a corresponding location 650 on the captured image 640, which was taken from a different perspective, by virtue of the known coordinate systems of each of the cameras 56, 58. Further, the controller 400 determines a width 652 of the seed 12 at the corresponding location 650 as shown in FIG. 54. The controller 400 also identifies the location of a back edge 644 of the seed 12. Based on this information and the desired depth of the trim cut and/or bisection cut (e.g., from user inputs), the controller 400 is able to determine the distance to move the cutting blade 170 toward the front wall 154 when trimming and/or bisecting the embryonic axis 440.

Figure 55:
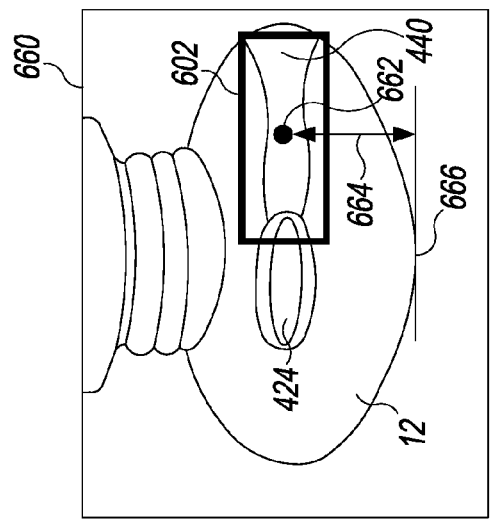

The controller 400 also determines the appropriate positioning of the cutting blade 170 for the bisection of the seed 12. To do so, the controller 400 operates the camera 58 to capture an image 660 of the seed 12 and analyzes the captured image 660 to locate a center of mass 662 of the embryonic axis 440 as shown in FIG. 55. As indicated above, the controller 400 may first determine the location 602 of the embryonic axis 440 in the captured image 660 using, for example, a feature matching algorithm in conjunction with the reference image 612 (see FIG. 42). Further, the controller 400 determines a distance 664 between a bottom edge 666 of the seed 12 and the center of mass 662 of the embryonic axis 440. As indicated above, the controller 400 may convert the pixel distance to a physical distance. Accordingly, the distance 664 is used to determine the distance above the flange 124 at which the horizontal bisection cut is made.

Referring back to FIG. 15, once the controller 400 determines the proper orientations of the seed 12 for trimming and bisection, the procedure 1000 advances to block 1020 of FIG. 16. In block 1020, the controller 400 operates the robotic arm 16 to position the gripped seed 12 on the cutting block 116. As described above, based on structural data stored in memory, the controller 400 is able to determine the distance 646 between the grip axis 358 and the back edge 644 of the gripped seed 12. Accordingly, in the illustrative embodiment, the controller 400 operates the robotic arm 16 to position the seed 12 on the flange 124 at a point in which the grip axis 358 is positioned the determined distance 646 away from the front wall 154 of the cutting block 116. At the distance 646, the seed 12 is positioned for cutting at the proper depth and orientation. In the illustrative embodiment, the seed 12 is positioned such that the back edge 644 of the seed 12 just contacts the front wall 154 of the cutting block 116.

Figure 56:
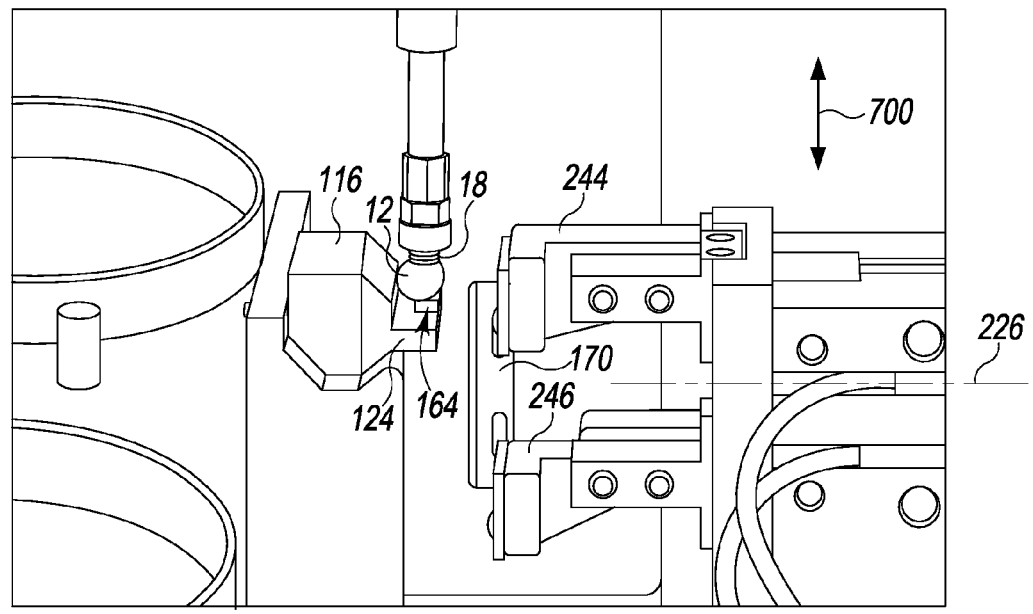
FIGS. 56-59 are illustrations of the system of FIG. 1 cutting a seed to prepare the seed for gene transformation.

In block 1022, the controller 400 operates the cutting device 112 to trim the embryonic axis 440. To do so, the controller 400 activates the compressed air source 230 to cause the shaft 224 (and hence the jaws 244, 246) to rotate about the axis 226. The shaft 224 is rotated to position the cutting blade 170 vertically (i.e., perpendicular to the flange 124 of the cutting block 116). As shown in FIG. 56, the cutting blade 170 is aligned with the slot 164 defined in the flange 124.

Figure 57:
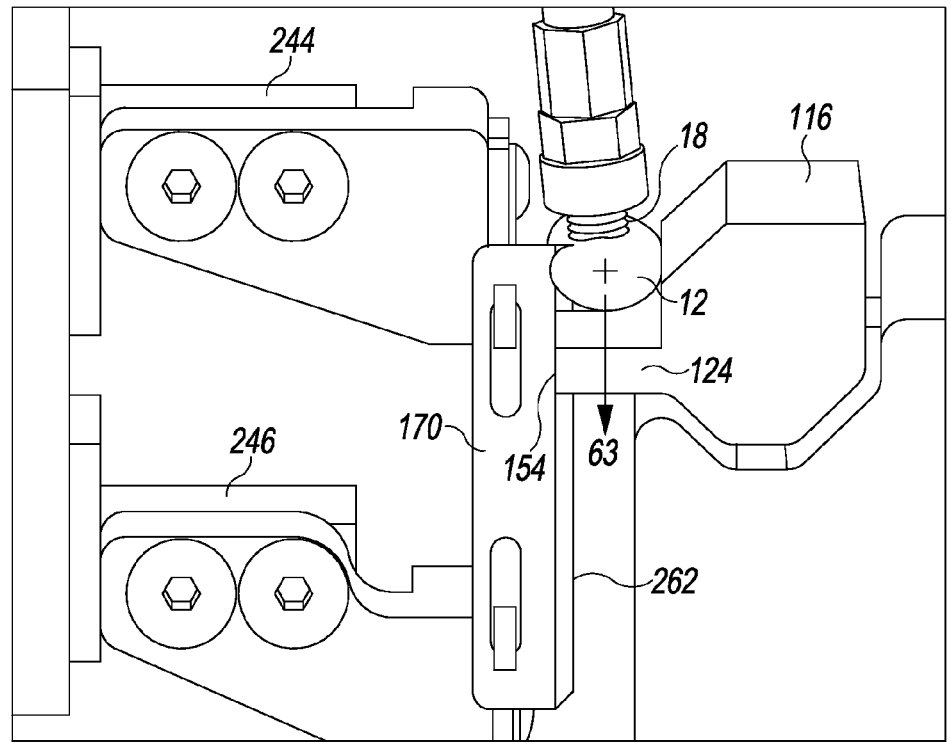
Figure 58:
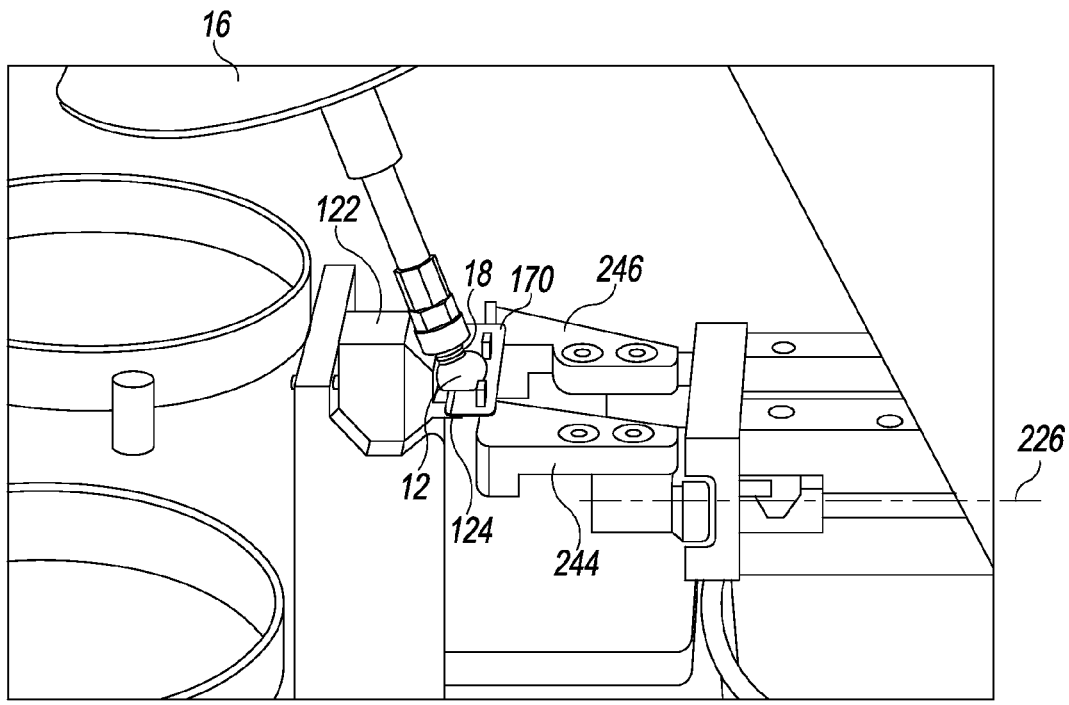

The controller 400 may also operate the intermediate drive stage 210 to raise or lower the cutting blade 170, as indicated by arrows 700 in FIG. 56. To trim the embryonic axis 440, the controller 400 operates the drive stage 194 of the cutting device 112 to advance the cutting blade 170 linearly along the axis 226 toward the seed 12 on the block 116. As shown in FIG. 57, the cutting blade 170 is advanced into the slot 164 and the seed 12 until the cutting blade 170 reaches the previously determined cutting distance (e.g., relative to the front wall 154), thereby trimming the embryonic axis 440.

Figure 63:
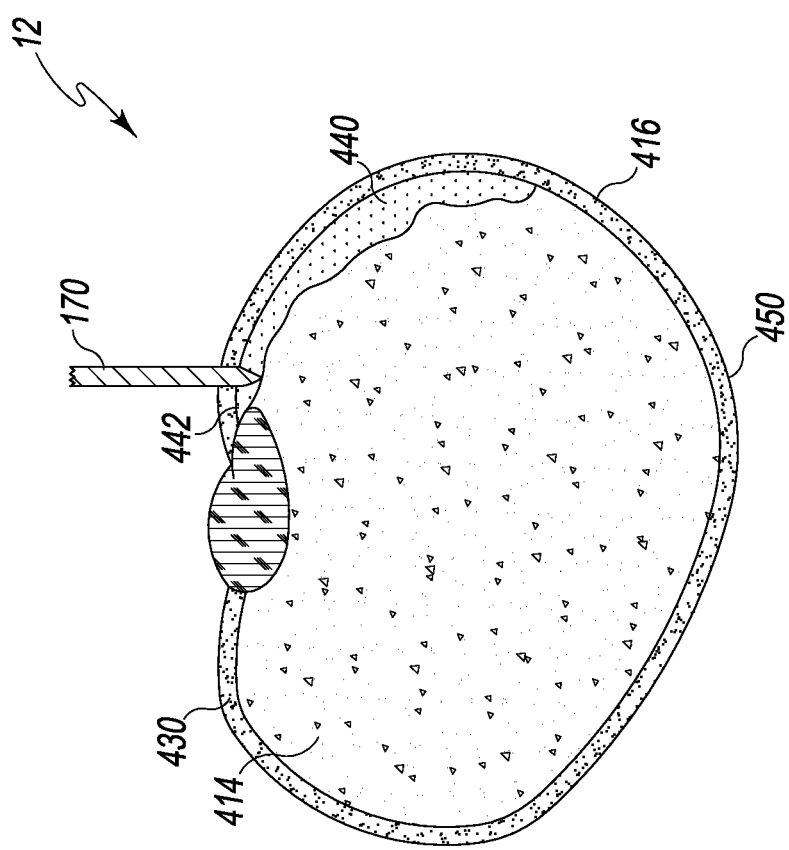
FIG. 63 is a cross-sectional elevation view of the soybean seed taken along the line 63-63 in FIG. 57.

As shown in FIG. 63, the cutting blade 170 is advanced through the embryonic axis 440 to separate the tip 442 of the axis 440 from the rest of the axis 440. As described above, typically, between ⅓ and ½ of the embryonic axis 440 may left attached. In other words, between ½ and ⅔ of the embryonic axis 440 may be trimmed along with the tip 442 from the rest of the embryonic axis 440. In the illustrative embodiment, the cutting blade 170 does not penetrate the cotyledons 412, 414 when the embryonic axis 440 is trimmed. In some embodiments, it may be desirable to wound the cotyledons 412, 414 by advancing the cutting blade 170 further into the seed 10. The controller 400 may then operate the drive stage 194 to move the cutting blade 170 away from the seed 12 and out of the slot 164.

The procedure 1000 may then advance to block 1024 in which the controller 400 operates the cutting device 112 to position the cutting blade 170 horizontally for bisection of the seed 12. To do so, the controller 400 activates the compressed air source 230 to cause the shaft 224 (and hence the jaws 244, 246) to rotate about the axis 226 from the vertical position shown in FIGS. 56-57 to the horizontal position shown in FIG. 58. The controller 400 may also operate the intermediate drive stage 210 to raise or lower the cutting blade 170 to align the cutting blade 170 with the longitudinal axis 418 of the seed 12. As discussed above, the controller 400 may use the distance 664 and other known physical dimensions to determine the distance above the flange 124 at which the cutting blade 170 is to be positioned.

Figure 59:
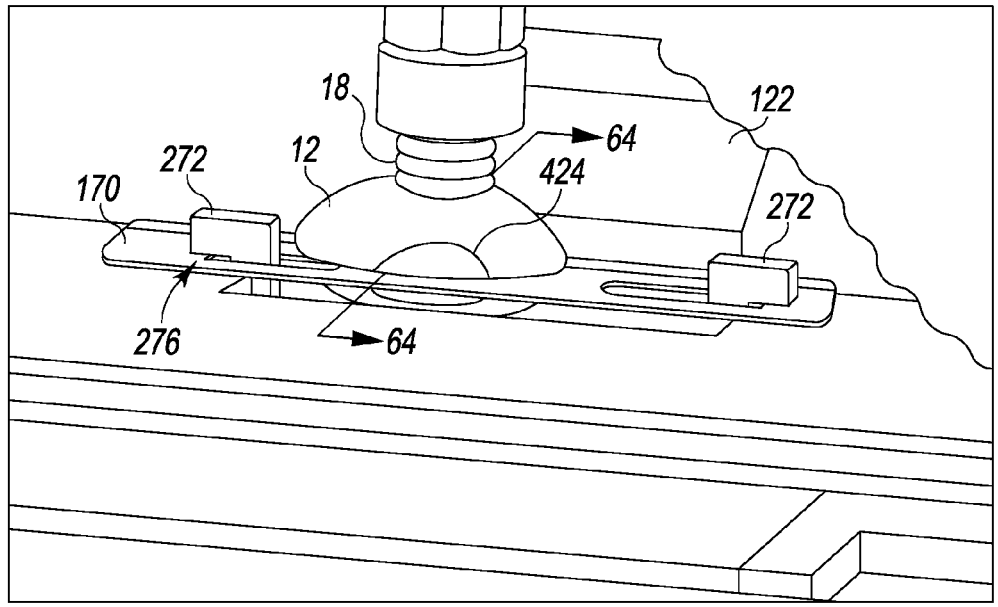

In block 1026 of the procedure 1000, the controller 400 moves cutting blade 170 toward the front wall 154 to bisect the seed 12. To do so, the controller 400 operates the drive stage 194 of the cutting device 112 to advance the cutting blade 170 linearly along the axis 226 toward the seed 12 on the block 116. As shown in FIG. 59, the cutting blade 170 is advanced into the seed 12 until the cutting blade 170 reaches the previously determined bisection distance as described above (e.g., relative to the front wall 154).

Figure 64:
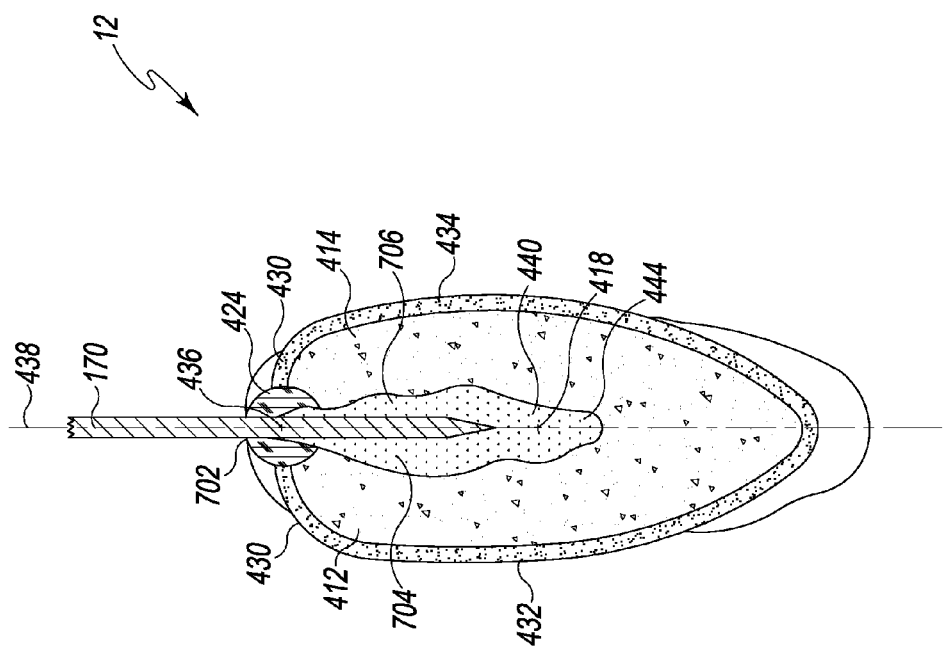
FIG. 64 is a cross-sectional elevation view of the soybean seed taken along the line 64-64 in FIG. 59.

As shown in FIG. 64, the cutting blade 170 is aligned with plane 438 defined by the longitudinal axis 436 of the hilum 424 and the longitudinal axis 418 of the seed 12 and advanced through the seed coat 416 and the hilum 424 along the plane 438, thereby creating an opening 702 in the seed 12. The embryonic axis 440 is sliced into a medial section 704 attached to the cotyledon 412 and a lateral section 706 attached to the cotyledon 414. As shown in FIG. 64, the cutting blade 170 passes through the base 444 of the embryonic axis 440. It will be appreciated that, in the illustrative embodiment, the cutting blade 170 does not completely bisect the seed 12 into two pieces. Rather, after the embryonic trimming and bisection, the seed 12 can still be transported by the grip 18 as a single piece. The controller 400 may then operate the drive stage 194 to move the cutting blade 170 away from the seed 12.

In block 1028 of the procedure 1000, the controller 400 operates the robotic arm 16 to move the bisected seed 12 to the plate 38 located at the corresponding receiving area 26. The controller 400 then deactivates the negative pressure source 356 to drop the bisected seed 12 onto the plate 38. In block 1030, the controller 400 operates the robotic arm 16 to clear any debris from the cutting block 116. In some embodiments, the robotic arm 16 may perform one or more passes of the grip 18 along the upper wall 156 of the flange 124 to clear debris. In other embodiments, the grip assembly 320 includes a pressure source that is electrically coupled to the controller 400 and configured to deliver pressurized fluid (e.g., compressed air) through the passageways 352, 354 to repel light objects such as debris. In such embodiments, the controller 400 may deliver operate the pressure source to deliver pressurized fluid to the cutting block 116 as the grip 18 passes along the flange 124.

In block 1032, the controller 400 may operate the robotic arm 16 and the cutting device 112 to replace periodically the cutting blade 170. Depending on the particular embodiment, the cutting blade 170 may be replaced after a predefined amount of time has lapsed, after a threshold number of seeds 12 have been processed, and/or in response to another condition.

It will be appreciated that the procedure 1000 or portions of the procedure 1000 may be repeated for each seed 12 on the plate 36 in the delivery area 24. Further, the procedure 1000 may be implemented using both robotic arms 16 such that the arms 16 alternate use of the stations 28, 30. Further, it should be appreciated that the procedure may be implemented with one or more robotic arms 16 that each utilize its own dedicated stations 28, 30.

Figure 65:
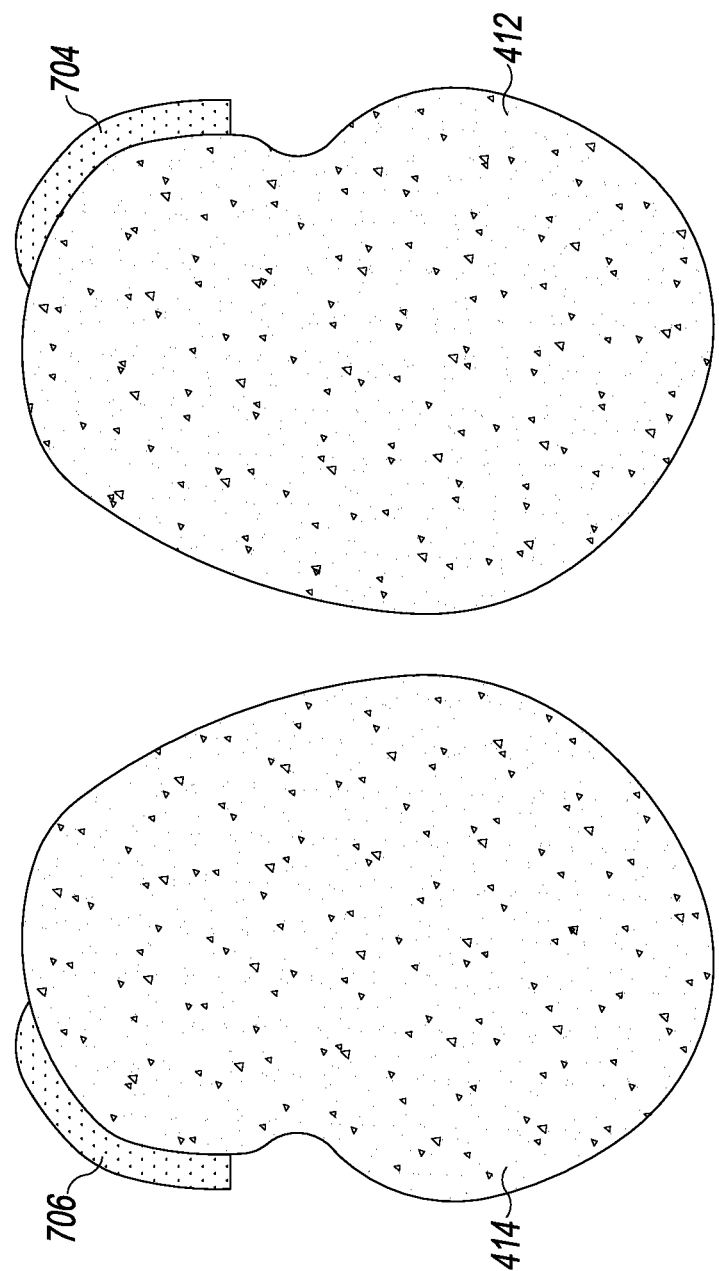
FIG. 65 is a plan view of a pair of cotyledon segments prepared using the system of FIG. 1.

After one or more of the cut seeds 12 have been placed in a receiving area 26, the user may remove the seeds 12 from the system 10 for further processing. Among other things, the user may remove separate the cotyledon from the seed coat, additionally wound the cotyledon, or inoculate the cotyledon with an *Agrobacterium* culture. To separate the seed coat 416 from the cotyledons 412, 414, the user may widen the opening 702 to further expose the cotyledons 412, 414. The cotyledons 412, 414 may be removed from the seed coat 416, and the seed coat 416 discarded. As shown in FIG. 65, each cotyledon, which may be referred to as a split soybean seed or cotyledon segment, includes a section of the embryonic axis. In the illustrative embodiment, the cotyledon segment 412 includes the section 704 of the embryonic axis 440, while the cotyledon segment 414 includes the section 706 of the embryonic axis 440. Each of the cotyledon segments 412, 414 is then ready for further processing, including additional wounding or inoculation with an *Agrobacterium* culture.

An *Agrobacterium* culture is a widely utilized method for introducing an expression vector into plants is based on the natural transformation system of *Agrobacterium*. Horsch et al., *Science* 227:1229 (1985). *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado, C. I., *Crit. Rev. Plant. Sci.* 10:1 (1991). Descriptions of *Agrobacterium* vector systems and methods for *Agrobacterium*-mediated gene transfer are also available, for example, Gruber et al., supra, Miki et al., supra, Moloney et al., *Plant Cell Reports* 8:238 (1989), and U.S. Pat. Nos. 4,940,838 and 5,464,763.

If *Agrobacterium* is used for the transformation, the DNA to be inserted should be cloned into special plasmids, namely either into an intermediate vector or into a binary vector. Intermediate vectors cannot replicate themselves in *Agrobacterium*. The intermediate vector can be transferred into *Agrobacterium tumefaciens* by means of a helper plasmid (conjugation). The Japan Tobacco Superbinary system is an example of such a system (reviewed by Komari et al. (2006) In: Methods in Molecular Biology (K. Wang, ed.) No. 343: *Agrobacterium* Protocols ($2^{nd}$ Edition, Vol. 1) HUMANA PRESS Inc., Totowa, N.J., pp. 15-41; and Komori et al. (2007) Plant Physiol. 145:1155-1160). Binary vectors can replicate themselves both in *E. coli* and in *Agrobacterium*. They comprise a selection marker gene and a linker or polylinker which are framed by the right and left T-DNA border regions. They can be transformed directly into *Agrobacterium* (Holsters, 1978). The *Agrobacterium* used as host cell is to comprise a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the construct and adjacent marker into the plant cell DNA when the cell is infected by the bacteria using a binary T DNA vector (Bevan (1984) *Nuc. Acid Res.* 12:8711-8721) or the co-cultivation procedure (Horsch et al. (1985) *Science* 227:1229-1231). Generally, the *Agrobacterium* transformation system is used to engineer dicotyledonous plants (Bevan et al. (1982) *Ann. Rev. Genet* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Split soybean seeds comprising a portion of an embryonic axis may be typically inoculated with *Agrobacterium* culture containing a suitable genetic construct for about 0.5 to 3.0 hours, more typically for about 0.5 hours, followed by a period of co-cultivation on suitable medium for up to about 5 days. Explants that putatively contain a copy of the transgene arise from the culturing of the transformed split soybean seeds comprising a portion of an embryonic axis. These explants may be identified and isolated for further tissue propagation.

A number of alternative techniques can also be used for inserting DNA into a host plant cell. Those techniques include, but are not limited to, transformation with T-DNA delivered by *Agrobacterium tumefaciens* or *Agrobacterium rhizogenes* as the transformation agent. From example of *Agrobacterium* technology are described in, for example, in U.S. Pat. Nos. 5,177,010, 5,104,310, European Patent Application No. 0131624B1, European Patent Application No. 120516, European Patent Application No. 159418B1, European Patent Application No. 176112, U.S. Pat. Nos. 5,149,645, 5,469,976, 5,464,763, 4,940,838, 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. Nos. 5,231,019, 5,463,174, 4,762,785, 5,004,863, and 5,159,135. The use of T-DNA-containing vectors for the transformation of plant cells has been intensively researched and sufficiently described in European Patent Application 120516; An et al, (1985, EMBO J. 4:277-284), Fraley et al, (1986, Crit. Rev. Plant Sci. 4: 1-46), and Lee and Gelvin (2008, Plant Physiol. 146: 325-332), and is well established in the field.

Another known method of plant transformation is microprojectile-mediated transformation wherein DNA is carried on the surface of microprojectiles. In this method, the expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Alternatively, gene transfer and transformation methods include, but are not limited to, protoplast transformation through calcium chloride precipitation, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505).

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method for automated seed preparation, the method comprising:
    capturing an image of a surface including at least one seed,
    locating the seed on the surface based on a captured image,
    gripping the seed with a robotic arm,
    operating the robotic arm to move the seed from the surface to a separate location,
    capturing a plurality of images of the seed in the separate location, and
    determining a proper orientation of the seed for bisection based on the plurality of captured images,
    orienting the seed on a cutting block for bisection of the seed, and
    bisecting the seed when the seed is oriented on the cutting block.

2. The method of claim 1, wherein the surface is in a tray and locating the seed comprises locating the seed on the tray having a plurality of seeds placed thereon.

3. The method of claim 1, wherein capturing the plurality of images comprises:
    operating a first camera to capture a first image of the seed from a first perspective, and
    operating a second camera to capture a second image of the seed from a second perspective different from the first perspective.

4. The method of claim 1, wherein determining the proper orientation of the seed comprises locating a center of a hilum of the seed and a longitudinal axis of the seed.

5. The method of claim 4, wherein orienting the seed on the cutting block for bisection of the seed comprises aligning the seed with a cutting blade of a cutting device along an imaginary plane defined by the center of the hilum of the seed and the longitudinal axis of the seed.

6. The method of claim 1, further comprising trimming an embryonic axis of the seed when the seed is located on the cutting block.

7. The method of claim 6, wherein:
    determining the proper orientation of the seed for bisection based on the plurality of captured images also includes determining the proper orientation of the seed for trimming the embryonic axis, and
    trimming the embryonic axis of the seed includes positioning a cutting blade perpendicular to a longitudinal axis of the seed.

8. The method of claim 6, wherein bisecting the seed on the cutting block comprises bisecting the seed after trimming the embryonic axis of the seed.

9. The method of claim 1, wherein bisecting the seed on the cutting block comprises cutting through less than an entirety of the seed.

10. The method of claim 1, further comprising moving the bisected seed to an *Agrobacterium tumefaciens* solution.

11. The method of claim 1, further comprising sterilizing a grip of the robotic arm prior to gripping the seed.

12. The method of claim 1, further comprising:
    operating the robotic arm to select a cutting blade, and
    positioning the cutting blade on a cutting device, wherein bisecting the seed when the seed is oriented on the cutting block includes inserting the cutting blade into the seed.

13. The method of claim 1, further comprising:
gripping a cutting blade with the robotic arm after bisecting the seed, and
replacing the cutting blade with a second cutting blade.

14. A seed preparation apparatus comprising:
a first camera configured to capture a first image of a seed placed on a surface,
a robotic arm operable to grip the seed and to move the seed from the surface to a lighted chamber,
a second camera configured to capture a second image of the seed within the lighted chamber, and
a cutting block configured to receive the seed,
wherein the robotic arm is further operable to position the seed on the cutting block in a proper orientation for bisection of the seed.

15. The seed preparation apparatus of claim 14, further comprising a light source to illuminate the seeds on the surface.

16. The seed preparation apparatus of claim 14, wherein the lighted chamber is defined in a lighted dome.

17. The seed preparation apparatus of claim 14, further comprising:
a third camera configured to capture a third image of the seed within the lighted chamber, and
an electronic controller configured to analyze the second image and the third image to determine the proper orientation of the seed.

18. The seed preparation apparatus of claim 17, further comprising a light source configured to light an interior of the lighted chamber.

19. The seed preparation apparatus of claim 17, wherein the electronic controller is further configured to analyze the first image to locate the seed on the surface.

20. A seed preparation apparatus comprising:
a chamber,
a first camera configured to capture a first image of a seed on a surface,
a second camera configured to capture a second image of the seed within the chamber,
a cutting device configured to bisect the seed,
a robotic arm including a gripping device to grip the seed for movement, and
an electronic controller configured to:
locate the seed on the surface based on the first image,
operate the robotic arm to grasp the seed on the surface and move the seed to the cutting device in an orientation based on the second image, and
operate the cutting device to bisect the seed.

21. The seed preparation apparatus of claim 20, wherein the electronic controller is configured to:
operate the robotic arm to move the seed from the surface to the chamber, and
operate the second camera to capture the second image.

22. The seed preparation apparatus of claim 21, wherein the electronic controller is configured to analyze a plurality of images of the seed to determine a proper orientation of the seed for bisection of the seed and trimming an embryonic axis of the seed.

23. The seed preparation apparatus of claim 22, wherein:
the robotic arm is configured to move the seed to the cutting device to position the seed in the proper orientation, and
the cutting device is configured to trim the embryonic axis of the seed while the seed is positioned in the cutting device in the proper orientation.

* * * * *